United States Patent
Jang et al.

(10) Patent No.: US 12,414,984 B2
(45) Date of Patent: Sep. 16, 2025

(54) FUSION PROTEIN COMPRISING ANTI-CD73 ANTIBODY AND IL-2, AND USE THEREOF

(71) Applicant: GI INNOVATION, INC., Seoul (KR)

(72) Inventors: Myung Ho Jang, Seoul (KR); Young Jun Koh, Seoul (KR); Dan Bee Ha, Seoul (KR)

(73) Assignee: GI INNOVATION, INC., Seoul (KR)

( * ) Notice: Subject to any disclaimer, the term of this patent is extended or adjusted under 35 U.S.C. 154(b) by 0 days.

(21) Appl. No.: 18/815,390

(22) Filed: Aug. 26, 2024

(65) Prior Publication Data

US 2024/0408176 A1    Dec. 12, 2024

Related U.S. Application Data

(63) Continuation of application No. PCT/KR2023/008664, filed on Jun. 22, 2023.

(30) Foreign Application Priority Data

Jun. 22, 2022   (KR) .................. 10-2022-0076279

(51) Int. Cl.
| | | |
|---|---|---|
| *C07K 16/46* | (2006.01) | |
| *A61K 38/20* | (2006.01) | |
| *A61K 39/00* | (2006.01) | |
| *A61K 39/395* | (2006.01) | |
| *A61P 35/00* | (2006.01) | |
| *C07K 14/55* | (2006.01) | |
| *C07K 16/28* | (2006.01) | |

(52) U.S. Cl.
CPC .... *A61K 38/2013* (2013.01); *A61K 39/39558* (2013.01); *A61P 35/00* (2018.01); *C07K 14/55* (2013.01); *C07K 16/2896* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 5,229,109 A | * | 7/1993 | Grimm ............... | A61P 37/04 424/85.1 |
| 2003/0124678 A1 | * | 7/2003 | Epstein ............... | A61P 37/00 435/325 |
| 2007/0036752 A1 | * | 2/2007 | Gillies ............... | A61P 35/00 435/325 |
| 2020/0071404 A1 | | 3/2020 | Sato et al. | |
| 2020/0369740 A1 | * | 11/2020 | Jang ................... | A61P 35/00 |
| 2021/0024646 A1 | * | 1/2021 | Yu ...................... | A61K 47/6851 |
| 2022/0125884 A1 | | 4/2022 | Baca et al. | |
| 2022/0380781 A1 | | 12/2022 | Jang | |
| 2022/0389070 A1 | | 12/2022 | Jang | |
| 2023/0104217 A1 | | 4/2023 | Jang | |
| 2024/0352084 A1 | * | 10/2024 | Gonzalez .......... | A61P 35/00 |

FOREIGN PATENT DOCUMENTS

| | | | |
|---|---|---|---|
| KR | 10-2019-0091281 A | 8/2019 | |
| KR | 10-2020-0032009 A | 3/2020 | |
| KR | 10-2021-0008110 A | 1/2021 | |
| KR | 10-2313505 B1 | 10/2021 | |
| WO | WO-2009061853 * | 5/2009 | ............ C07K 14/55 |
| WO | 2021/043229 A1 | 3/2021 | |
| WO | 2022/087149 A2 | 4/2022 | |

OTHER PUBLICATIONS

Silver et al. Engineered antibody fusion proteins for targeted disease therapy. Trends in Pharmacological Sciences, Dec. 2021, 42(12):1064-1081 (Year: 2021).*
Skrombolas and Frelinger. Challenges and developing solutions for increasing the benefits of IL-2 treatment in tumor therapy. Expert Rev Clin Immunol. Feb. 2014;10(2):207-217 (Year: 2014).*
Hu et al. Generation of low-toxicity interleukin-2 fusion proteins devoid of vasopermeability activity. Blood 101, 4853-4861 (2003) (Year: 2003).*
Heaton et al. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53, 2597-602 , 1993 (Year: 1993).*
Heuser et al. Anti-CD30-scFv-Fc-IL-2 antibody-cytokine fusion protein that induces resting NK cells to highly efficient cytolysis of Hodgkin's lymphoma derived tumour cells. Int. J. Cancer: 110, 386-394 (2004) (Year: 2004).*
Shi et al. A recombinant anti-erbB2, scFv-Fc-IL-2 fusion protein retains antigen specificity and cytokine function. Biotechnology Letters 25: 815-819, 2003 (Year: 2003).*
Shanafelt et al. (Nature Biotechnol 18, 1197-1202 (2000)) (Year: 2000).*
International Search Report for International Application No. PCT/KR2023/008664 dated Sep. 21, 2023.
Communication dated Apr. 17, 2025, issued in Korean Application No. 10-2023-0080204.

* cited by examiner

Primary Examiner — Maher M Haddad
(74) Attorney, Agent, or Firm — Sughrue Mion, PLLC

(57) ABSTRACT

A fusion protein in which an anti-CD73 antibody or an antigen-binding fragment thereof and IL-2 are linked to each other, and the use thereof are disclosed. The fusion protein or dimer thereof contains an anti-CD73 antibody or an antigen-binding fragment thereof and IL-2, and is able to inhibit adenosine production by binding to CD73 of cancer cells, thereby blocking the A2AR and A2BR signaling pathways, thus controlling the tumor microenvironment. Furthermore, the fusion protein or dimer thereof is able to activate immune cells (CD8+ T cells and CD4+ T cells) along with less activation of immunosuppressive cells such as regulatory T cells (Tregs). In addition, IL-2 or a variant thereof in the fusion protein is able to activate immune cells. Therefore, the fusion protein and dimer thereof may be useful for preventing or treating cancer.

12 Claims, 16 Drawing Sheets

Specification includes a Sequence Listing.

SEQUENCE LISTING

```
Sequence total quantity: 43
SEQ ID NO: 1            moltype = AA  length = 19
FEATURE                 Location/Qualifiers
REGION                  1..19
                        note = mIgG signal
source                  1..19
                        mol_type = protein
                        organism = synthetic construct
SEQUENCE: 1
MEWSWVFLFF LSVTTGVHS                                                   19

SEQ ID NO: 2            moltype = AA  length = 126
FEATURE                 Location/Qualifiers
REGION                  1..126
                        note = anti-hCD73 sdAb(AHF10235)
source                  1..126
                        mol_type = protein
                        organism = synthetic construct
SEQUENCE: 2
QVQVQESGGG LVQAGDSLRL SCAASGRSIS RYNMGWFRQA PGKEREFVAA ISRSGGVTYY       60
ADSVKGRLTI SRDNAKSAVY LQMNSLKPED TAVYYCAADW RNSDSPSPLI IVYDYWGQGT      120
QVTVSS                                                                 126

SEQ ID NO: 3            moltype = AA  length = 126
FEATURE                 Location/Qualifiers
REGION                  1..126
                        note = anti-hCD73 sdAb(AHF10240)
source                  1..126
                        mol_type = protein
                        organism = synthetic construct
SEQUENCE: 3
EVQLVESGGG VVQTGGSLRL SCAASGRTFT HLAMGWFRQA PGKEREFVAA ISNSGAGTQF       60
ADSVKGRFTI SRDNAKNTVY LQMNSLKPED TAVYYCAADW GTRDSPSKLN AVYDYWGRGT      120
QVTVSS                                                                 126

SEQ ID NO: 4            moltype = AA  length = 126
FEATURE                 Location/Qualifiers
REGION                  1..126
                        note = anti-hCD73 sdAb(AHP04167)
source                  1..126
                        mol_type = protein
                        organism = synthetic construct
SEQUENCE: 4
EVQLVESGGG LVQAGGSLRL SCVVSGRTFS NYHMGWFRQA PGKEREFVAV IGRSGGPTYY       60
ADSVKGRFTI SRDNAKNTVY LQMNSLKPED TAVYYCAGDW RNSDSPSKLK PVYDYWGQGT      120
QVTVSS                                                                 126

SEQ ID NO: 5            moltype = AA  length = 18
FEATURE                 Location/Qualifiers
REGION                  1..18
```

```
                         note = Linker 1
source                   1..18
                         mol_type = protein
                         organism = synthetic construct
SEQUENCE: 5
GGGGSAESKY GPPCPPCP                                                 18

SEQ ID NO: 6             moltype = AA   length = 216
FEATURE                  Location/Qualifiers
REGION                   1..216
                         note = hIgG4 Fc (F01)
source                   1..216
                         mol_type = protein
                         organism = synthetic construct
SEQUENCE: 6
APEAAGGPSV FLFPPKPKDQ LMISRTPEVT CVVVDVSQED PEVQFNWYVD GVEVHNAKTK    60
PREEQFNSTY RVVSVLTVLH QDWLNGKEYK CKVSNKGLPS SIEKTISKAK GQPREPQVYT   120
LPPSQEEMTK NQVSLTCLVK GFYPSDIAVE WESNGQPENN YKTTPPVLDS DGSFFLYSRL   180
TVDKSRWQEG NVFSCSVLHE ALHNHYTQKS LSLSLG                             216

SEQ ID NO: 7             moltype = AA   length = 15
FEATURE                  Location/Qualifiers
REGION                   1..15
                         note = Linker 2
source                   1..15
                         mol_type = protein
                         organism = synthetic construct
SEQUENCE: 7
GGGGSGGGGS GGGGS                                                    15

SEQ ID NO: 8             moltype = AA   length = 133
FEATURE                  Location/Qualifiers
REGION                   1..133
                         note = hIL2v3
source                   1..133
                         mol_type = protein
                         organism = synthetic construct
SEQUENCE: 8
APTSSSTKKT QLQLEHLLLD LQMILNGINN YKNPKLTAML TAKFYMPKKA TELKHLQCLE    60
RELKPLEEVL NLAQSKNFHL RPRDLISNIN VIVLELKGSE TTFMCEYADE TATIVEFLNR   120
WITFCQSIIS TLT                                                     133

SEQ ID NO: 9             moltype = AA   length = 119
FEATURE                  Location/Qualifiers
REGION                   1..119
                         note = Variable heavy chain of anti-hCD73 Ab (CSA0060)
source                   1..119
                         mol_type = protein
                         organism = synthetic construct
SEQUENCE: 9
QVQLVQSGAE VKKPGSSVKV SCKFSGGSFT SYSFSWVRQA PGQGLEWMGR IIPVLTTTDY    60
AQKFRDRVTI TADESTSTAY MELSGLRSED TAVYYCASGL KKNWYFDLWG RGALITVSS    119

SEQ ID NO: 10            moltype = AA   length = 98
FEATURE                  Location/Qualifiers
REGION                   1..98
                         note = Constant heavy chain of anti-hCD73 Ab (CSA0060)
source                   1..98
                         mol_type = protein
                         organism = synthetic construct
SEQUENCE: 10
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRV                            98

SEQ ID NO: 11            moltype = AA   length = 12
FEATURE                  Location/Qualifiers
REGION                   1..12
                         note = Linker 3
source                   1..12
                         mol_type = protein
                         organism = synthetic construct
SEQUENCE: 11
ESKYGPPCPP CP                                                       12

SEQ ID NO: 12            moltype = AA   length = 10
FEATURE                  Location/Qualifiers
REGION                   1..10
                         note = Linker 4
source                   1..10
```

```
                            mol_type = protein
                            organism = synthetic construct
SEQUENCE: 12
GGGGSGGGGS                                                           10

SEQ ID NO: 13               moltype = AA   length = 107
FEATURE                     Location/Qualifiers
REGION                      1..107
                            note = Variable light chain of anti-hCD73 Ab (CSA0060)
source                      1..107
                            mol_type = protein
                            organism = synthetic construct
SEQUENCE: 13
DIQMTQSPSF LSASVGDRVT ITCQASQDIS HYLNWYQQKP GKAPKLLIYD ASSLETGVPS     60
RFSGSGSGTS FTLTISSLQP EDFATYYCQQ YDDFPLTFGG GTKVDIK                  107

SEQ ID NO: 14               moltype = AA   length = 107
FEATURE                     Location/Qualifiers
REGION                      1..107
                            note = Constant light chain of anti-hCD73 Ab (0060, kappa)
source                      1..107
                            mol_type = protein
                            organism = synthetic construct
SEQUENCE: 14
RSVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                  107

SEQ ID NO: 15               moltype = AA   length = 8
FEATURE                     Location/Qualifiers
REGION                      1..8
                            note = CDR1 of anti-hCD73 sdAb (AHF10235)
source                      1..8
                            mol_type = protein
                            organism = synthetic construct
SEQUENCE: 15
GRSISRYN                                                              8

SEQ ID NO: 16               moltype = AA   length = 8
FEATURE                     Location/Qualifiers
REGION                      1..8
                            note = CDR2 of anti-hCD73 sdAb (AHF10235)
source                      1..8
                            mol_type = protein
                            organism = synthetic construct
SEQUENCE: 16
ISRSGGVT                                                              8

SEQ ID NO: 17               moltype = AA   length = 19
FEATURE                     Location/Qualifiers
REGION                      1..19
                            note = CDR3 of anti-hCD73 sdAb (AHF10235)
source                      1..19
                            mol_type = protein
                            organism = synthetic construct
SEQUENCE: 17
AADWRNSDSP SPLIIVYDY                                                 19

SEQ ID NO: 18               moltype = AA   length = 8
FEATURE                     Location/Qualifiers
REGION                      1..8
                            note = CDR1 of anti-hCD73 sdAb (AHF10240)
source                      1..8
                            mol_type = protein
                            organism = synthetic construct
SEQUENCE: 18
GRTFTHLA                                                              8

SEQ ID NO: 19               moltype = AA   length = 8
FEATURE                     Location/Qualifiers
REGION                      1..8
                            note = CDR2 of anti-hCD73 sdAb (AHF10240)
source                      1..8
                            mol_type = protein
                            organism = synthetic construct
SEQUENCE: 19
ISNSGAGT                                                              8

SEQ ID NO: 20               moltype = AA   length = 19
FEATURE                     Location/Qualifiers
```

```
REGION                  1..19
                        note = CDR3 of anti-hCD73 sdAb (AHF10240)
source                  1..19
                        mol_type = protein
                        organism = synthetic construct
SEQUENCE: 20
AADWGTRDSP SKLNAVYDY                                                        19

SEQ ID NO: 21           moltype = AA  length = 8
FEATURE                 Location/Qualifiers
REGION                  1..8
                        note = CDR1 of anti-hCD73 sdAb (AHP04167)
source                  1..8
                        mol_type = protein
                        organism = synthetic construct
SEQUENCE: 21
GRTFSNYH                                                                     8

SEQ ID NO: 22           moltype = AA  length = 8
FEATURE                 Location/Qualifiers
REGION                  1..8
                        note = CDR2 of anti-hCD73 sdAb (AHP04167)
source                  1..8
                        mol_type = protein
                        organism = synthetic construct
SEQUENCE: 22
IGRSGGPT                                                                     8

SEQ ID NO: 23           moltype = AA  length = 19
FEATURE                 Location/Qualifiers
REGION                  1..19
                        note = CDR3 of anti-hCD73 sdAb (AHP04167)
source                  1..19
                        mol_type = protein
                        organism = synthetic construct
SEQUENCE: 23
AGDWRNSDSP SKLKPVYDY                                                        19

SEQ ID NO: 24           moltype = AA  length = 8
FEATURE                 Location/Qualifiers
REGION                  1..8
                        note = VH-HCDR1 of anti-hCD73 Ab (CSA0060)
source                  1..8
                        mol_type = protein
                        organism = synthetic construct
SEQUENCE: 24
GGSFTSYS                                                                     8

SEQ ID NO: 25           moltype = AA  length = 8
FEATURE                 Location/Qualifiers
REGION                  1..8
                        note = VH-HCDR2 of anti-hCD73 sdAb (CSA0060)
source                  1..8
                        mol_type = protein
                        organism = synthetic construct
SEQUENCE: 25
IIPVLTTT                                                                     8

SEQ ID NO: 26           moltype = AA  length = 11
FEATURE                 Location/Qualifiers
REGION                  1..11
                        note = VH-HCDR3 of anti-hCD73 sdAb (CSA0060)
source                  1..11
                        mol_type = protein
                        organism = synthetic construct
SEQUENCE: 26
SGLKKNWYFD L                                                                11

SEQ ID NO: 27           moltype = AA  length = 6
FEATURE                 Location/Qualifiers
REGION                  1..6
                        note = VL-LCDR1 of anti-hCD73 Ab (CSA0060)
source                  1..6
                        mol_type = protein
                        organism = synthetic construct
SEQUENCE: 27
QDISHY                                                                       6

SEQ ID NO: 28           moltype =    length =
```

```
SEQUENCE: 28
000

SEQ ID NO: 29          moltype = AA  length = 8
FEATURE                Location/Qualifiers
REGION                 1..8
                       note = VL-LCDR3 of anti-hCD73 sdAb (CSA0060)
source                 1..8
                       mol_type = protein
                       organism = synthetic construct
SEQUENCE: 29
QYDDFPLT                                                                   8

SEQ ID NO: 30          moltype = DNA  length = 1551
FEATURE                Location/Qualifiers
misc_feature           1..1551
                       note = nucleotides coding for anti-hCD73 sdAb (AHF10235)
                        conjugated withhIL2v3 and signal peptide
source                 1..1551
                       mol_type = other DNA
                       organism = synthetic construct
SEQUENCE: 30
atggaatggt cctgggtgtt cctgttcttc ctgtccgtga ccaccggcgt gcactctcag   60
gtgcaggttc aagaatctgg cggcggattg gtgcaggccg gcgattctct gagactgtct  120
tgtgccgcct ctgccggtc catctctagg tacaacatgg gctggttcag acaggcccct  180
ggcaaagaga gagagttcgt cgccgccatc agcagatctg gcgagtgac ctactacgcc  240
gactccgtga aggccggct gaccatctcc agagacaacg ccaagtctgc cgtgtacctc  300
cagatgaact ccctgaagcc tgaggacacc gccgtgtact actgtgccgc cgattggcgg  360
aactccgact ctccttctcc tctgatcatc gtgtacgact actggggcca gggcacccaa  420
gtgacagttt ctagcggagg cggaggcagt gctgagcta agtatggccc tccttgtcct  480
ccatgtcctg ctccagaagc tgctggcggg ccctccgtgt ttctgttccc tccaaagcct  540
aaggaccagc tgatgatctc tcggacaccc gaagtgacct gcgtggtggt ggatgtgtct  600
caagaggacc ctgaggtgca gttcaattgg tacgtggacg gcgtggaagt gcacaacgcc  660
aagaccaagc ctagagagga acagttcaac tccacctaca gagtggtgtc cgtgctgacc  720
gtgctgcacc aggattggct gaacggcaaa gagtacaagt gcaaggtgtc caacaagggc  780
ctgccttcca gcatcgaaaa gaccatctcc aaggccaagg ccagcctag gaacccccag  840
gtttacaccc tgcctccaag ccaagaggaa atgaccaaga accaggtgtc cctgacctgc  900
ctggtcaagg gcttctaccc ttccgacatt gccgtggaat gggagagcaa tggccagcct  960
gagaacaact acaagaccac acctcctgtg ctggactccg acggctcctt ctttctgtac 1020
tcccgcctga ccgtggacaa gtccagatgg caagagggca acgtgttctc ctgctctgtg 1080
ctgcacgagg ccctgcacaa tcactacacc cagaagtccc tcagcctgtc ccttggcgga 1140
ggcggtggat ccgctcctac ctccagctcc accaagaaaa cccagttgca gctggaacat 1200
ctgctgctgg acctccagat gatcctgaat ggcatcaaca attacaagaa cccaaagctg 1260
accgccatgc tgaccgctaa gttctacatg cccaagaagg ccaccgagct gaagcactc 1320
cagtgcctgg aacgggaact gaagcctctg gaagaggtgc tgaatctggc ccagtccaag 1380
aacttccacc tgaggcctcg ggacctgatc tccaacatca cgtgatcgt gctggaactc 1440
aagggctccg agacaacctt catgtgcgag tacgccgacg agacagctac catcgtggaa 1500
tttctgaatc ggtggatcac cttctgccag tccatcatca gcaccctgac c           1551

SEQ ID NO: 31          moltype = DNA  length = 1494
FEATURE                Location/Qualifiers
misc_feature           1..1494
                       note = nucleotides coding for anti-hCD73 sdAb (AHF10235)
                        conjugated withhIL2v3
source                 1..1494
                       mol_type = other DNA
                       organism = synthetic construct
SEQUENCE: 31
caggtgcagg ttcaagaatc tggcggcgga ttggtgcagg ccggcgattc tctgagactg   60
tcttgtgccg cctctgccgg tccatctct aggtacaaca tgggctggtt cagacaggcc  120
cctggcaaag agagagagtt cgtcgccgcc atcagcagat ctggcggagt gacctactac  180
gccgactccg tgaaaggccg gctgaccatc tccagagaca cgccaagtc tgccgtgtac  240
ctccagatga actccctgaa gcctgaggac accgccgtgt actactgtgc cgccgattgg  300
cggaactccg actctccttc tcctctgatc atcgtgtacg actactgggg ccagggcacc  360
caagtgacag tttctagcgg aggcggaggc agtgctgagc taagtatggc cctccttgt  420
cctccatgtc ctgctccaga agctgctggc gggccctccg tgtttctgtt ccctccaaag  480
cctaaggacc agctgatgat ctctcggaca cccgaagtga cctgcgtggt ggtggatgtg  540
tctcaagagg accctgaggt gcagttcaat tggtacgtgg acggcgtgga agtgcacaac  600
gccaagacca agcctagaga ggaacagttc aactccacct acagagtggt gtccgtgctg  660
accgtgctgc accaggattg gctgaacggc aaagagtaca agtgcaaggt gtccaacaag  720
ggcctgcctt ccagcatcga aaagaccatc tccaaggcca aggccagcc tagggaaccc  780
caggtttaca ccctgcctcc aagccaagag gaaatgacca agaaccaggt gtccctgacc  840
tgcctggtca agggcttcta cccttccgac attgccgtgg aatgggagag caatggccag  900
cctgagaaca actacaagac cacacctcct gtgctggact ccgacggctc cttctttgt  960
tactcccgcc tgaccgtgga caagtccaga tggcaagagg gcaacgtgtt ctcctgctct 1020
gtgctgcacg aggccctgca caatcactac acccagaagt ccctcagcct gtcccttggc 1080
ggaggcggtg gatccgctcc tacctccagc tccaccaaga aacccagtt gcagctggaa 1140
catctgctgc tggacctcca gatgatcctg aatggcatca caattacaa gaaccccaag 1200
ctgaccgcca tgctgaccgc taagttctac atgcccaaga aggccaccga gctgaagcac 1260
```

-continued

```
ctccagtgcc tggaacggga actgaagcct ctggaagagg tgctgaatct ggcccagtcc   1320
aagaacttcc acctgaggcc tcgggacctg atctccaaca tcaacgtgat cgtgctggaa   1380
ctcaagggct ccgagacaac cttcatgtgc gagtacgccg acgagacagc taccatcgtg   1440
gaatttctga atcggtggat caccttctgc cagtccatca tcagcaccct gacc         1494

SEQ ID NO: 32          moltype = DNA   length = 1551
FEATURE                Location/Qualifiers
misc_feature           1..1551
                       note = nucleotides coding for anti-hCD73 sdAb (AHF10240)
                        conjugated withhIL2v3 and signal peptide
source                 1..1551
                       mol_type = other DNA
                       organism = synthetic construct
SEQUENCE: 32
atggaatggt cctgggtgtt cctgttcttc ctgtccgtga ccaccggcgt gcactctgaa    60
gtgcagctgg ttgaatctgg cggcggagtg gttcagacag cgggatctct gagactgtct   120
tgtgccgcct ccggcagaac ctttacacac tggctatgg gctggttccg gcaggctcct    180
ggaaaagaga gagagttcgt cgccgccatc tccaactgtg gcgctggcac acagttcgcc   240
gactctgtga aggcagatt caccatctct cgggacaacg ccaagaacac cgtgtacctc   300
cagatgaact ccctgaagcc tgaggacacc gccgtgtact actgtgctgc tgattggggc   360
accagagaca gcccctctaa gctgaatgcc gtgtacgact actggggcag aggcacccaa   420
gtgacagtgt cctctggagg cggaggcagt gctgagtcta gtatggccc tccttgtcct   480
ccatgtcctg ctccagaagc tgctggcggg ccctccgtgt tcctgttccc tccaaagcct   540
aaggaccagc tgatgatctc tcggacaccc gaagtgacct gcgtggtggt ggatgtgtct   600
caagaggacc ctgaggtgca gttcaattgg tacgtggacg gcgtggaagt gcacaacgcc   660
aagaccaagc ctagagagga acagttcaac tccacctaca gtgtgtcc cgtgctgacc   720
gtgctgcacc aggattggct gaacggcaaa gagtacaagt gcaaggtgtc caacaagggc   780
ctgccttcca gcatcgaaaa gaccatctcc aaggccaagg ccagcctag gaacccccag   840
gtttacaccc tgcctccaag ccaagaggaa atgaccaaga accaggtgtc cctgacctgc   900
ctggtcaagg gcttctaccc ttccgacatt gccgtggaat gggagagcaa tggccagcct   960
gagaacaact acaagaccac acctcctgtg ctggactccg acggctcctt ctttctgtac  1020
tcccgcctga ccgtggacaa gtccagatgg caagagggca acgtgttctc ctgctctgtg  1080
ctgcacgagg ccctgcacaa tcactacacc cagaagtccc tcagcctgtc ccttggcgga  1140
ggcggtggat ccgctcctac ctccagctcc accaagaaaa cccagttgca gctggaacat  1200
ctgctgctgg acctccagat gatcctgaat ggcatcaaca attacaagaa ccccaagctc  1260
accgccatgc tgaccgctaa gttctacatg cccaagaagg ccaccgagct gaagcacctc  1320
cagtgcctga acgggaact gaagcctctg aagaggtgc tgaatctggc ccagtccaag   1380
aacttccacc tgaggcctcg ggacctgatc ccaacatca acgtgatcgt gctggaactc   1440
aagggctccg agacaacctt catgtgcgag tacgccgacg agacagctac catcgtgaa   1500
tttctgaatc ggtggatcac cttctgccag tccatcatca gcaccctgac c            1551

SEQ ID NO: 33          moltype = DNA   length = 1494
FEATURE                Location/Qualifiers
misc_feature           1..1494
                       note = nucleotides coding for anti-hCD73 sdAb (AHF10240)
                        conjugated withhIL2v3
source                 1..1494
                       mol_type = other DNA
                       organism = synthetic construct
SEQUENCE: 33
gaagtgcagc tggttgaatc tggcggcgga gtggttcaga caggcggatc tctgagactg    60
tcttgtgccg cctccggcag aacctttaca cacctggcta tgggctggtt ccggcaggct   120
cctggaaaag agagagagtt cgtcgccgcc atctccaact ctggcgctgg cacacagttc   180
gccgactctg tgaagggcag attcaccatc tctcgggaca cgccaagaa caccgtgtac   240
ctccagatga actccctgaa gcctgaggac accgccgtgt actactgtgc tgctgattgg   300
ggcaccagag acagcccctc taagctgaat gccgtgtacg actactgggg cagaggcacc   360
caagtgacag tgtcctctgg aggcggaggc agtgctgagt ctaagtatgg ccctccttgt   420
cctccatgtc ctgctccaga agctgctggc gggccctccg tgtttctgtt ccctccaaag   480
cctaaggacc agctgatgat ctctcggaca cccgaagtga cctgcgtggt ggtggatgtg   540
tctcaagagg accctgaggt gcagttcaat tggtacgtgg acggcgtgga agtgcacaac   600
gccaagacca gcctagaga ggaacagttc aactccacct acagtgtggt gtccgtgctg   660
accgtgctgc accaggattg gctgaacggc aaagagtaca agtgcaaggt gtccaacaag   720
ggcctgcctt ccagcatcga aaagaccatc tccaaggcca agggccagcc tagggaaccc   780
caggttttaca ccctgcctcc aagccaagag gaaatgacca aggaccaggt gtccctgacc   840
tgcctggtca agggcttcta cccttccgac attgccgtgg aatgggagag caatggccag   900
cctgagaaca actacaagac cacacctcct gtgctggact ccgacggctc cttctttctg   960
tactcccgcc tgaccgtgga caagtccaga tggcaagagg caacgtgtt ctcctgctct  1020
gtgctgcacg aggccctgca caatcactac acccagaagt ccctcagcct gtcccttggc  1080
ggaggcggtg gatccgctcc tacctccagc tccaccaagt aaaacccagt tgcagctgga a  1140
catctgctgc tggacctcca gatgatcctg aatggcatca acaattacaa gaaccccaag  1200
ctgaccgcca tgctgaccgc taagttctac atgcccaaga aggccaccga gctgaagcac  1260
ctccagtgcc tggaacggga actgaagcct ctggaagagg tgctgaatct ggcccagtcc  1320
aagaacttcc acctgaggcc tcgggacctg atctccaaca tcaacgtgat cgtgctggaa  1380
ctcaagggct ccgagacaac cttcatgtgc gagtacgccg acgagacagc taccatcgtg  1440
gaatttctga atcggtggat caccttctgc cagtccatca tcagcaccct gacc         1494

SEQ ID NO: 34          moltype = DNA   length = 1551
FEATURE                Location/Qualifiers
misc_feature           1..1551
```

```
                        note = nucleotides coding for anti-hCD73 sdAb (AHP04167)
                            conjugated withhIL2v3 and signal peptide
            source      1..1551
                        mol_type = other DNA
                        organism = synthetic construct
SEQUENCE: 34
atggaatggt cctgggtgtt cctgttcttc ctgtccgtga ccaccggcgt gcactctgaa    60
gtgcagctgt tgaatctgg cggcggattg gttcaggctg gcggatctct gagactgtcc   120
tgtgtggtgt ccggcagaac cttctccaac taccacatgg gctggttcag acaggcccct   180
ggcaaagaac gcgagttcgt ggctgtgatc ggcagatctc gcggacctac ctactacgcc   240
gactccgtga agggcagatt caccatctcc agagacaacg ccaagaacac cgtgtacctc   300
cagatgaact ccctgaagcc tgaggacacc gccgtgtact actgtgccgg cgattggaga   360
aactccgact ctcccagcaa gctgaagccc gtgtacgatt attggggcca gggcacccaa   420
gtgaccgtgt cctctggagg cggaggcagt gctgagtcta agtatggccc tccttgtcct   480
ccatgtcctg ctccagaagc tgctggcggg ccctccgtgt ttctgttccc tccaaagcct   540
aaggaccagc tgatgatctc tcggacaccc gaagtgacct gcgtggtggt ggatgtgtct   600
caagaggacc ctgaggtgca gttcaattgg tacgtggacg gcgtggaagt gcacaacgcc   660
aagaccaagc ctagaaggaa acagttcaac tccacctaca gagtggtgtc cgtgctgacc   720
gtgctgcacc aggattggct gaacggcaaa gagtacaagt gcaaggtgtc caacaagggc   780
ctgccttcca gcatcgaaaa gaccatctcc aaggccaagg gccagcctag ggaaccccag   840
gtttacaccc tgcctccaag ccaagaggaa atgaccaaga accaggtgtc cctgacctgc   900
ctggtcaagg gcttctaccc ttccgacatt gccgtggaa gggagagcaa tggccagcct   960
gagaacaact acaagaccac acctcctgtg ctggactccg acggctcctt ctttctgtac  1020
tcccgcctga ccgtggacaa gtccagatgg caagagggca cgtgttctc ctgctctgtg  1080
ctgcacgagg ccctgcacaa tcactacacc cagaagtccc tcagcctgtc ccttggcgga  1140
ggcggtggat ccgctcctac ctccagctcc accaagaaa cccagttgca gctggaacat  1200
ctgctgctgg acctcagat gatcctgaat ggcatcaaca attacaagaa ccccaagctg  1260
accgccatgc tgaccgctaa gttctacatg cccaagaagg ccaccgagct gaagcacctc  1320
cagtgcctgg aacgggaact gaagcctctg aagaggtgc tgaatctggc ccagtccaag  1380
aacttccacc tgaggcctcg ggacctgatc tccaacatca acgtgatcgt gctgaactc  1440
aagggctccg agacaacctt catgtgcgag tacgccgacg agacagctac catcgtgaa  1500
tttctgaatc ggtggatcac cttctgccag tccatcatca gcaccctgac c           1551

SEQ ID NO: 35       moltype = DNA  length = 1494
FEATURE             Location/Qualifiers
misc_feature        1..1494
                    note = nucleotides coding for anti-hCD73 sdAb (AHP04167)
                        conjugated withhIL2v3
            source  1..1494
                    mol_type = other DNA
                    organism = synthetic construct
SEQUENCE: 35
gaagtgcagc tggttgaatc tggcggcgga ttggttcagg ctgcggatc tctgagactg    60
tcctgtgtgg tgtccggcag aaccttctcc aactaccaca tgggctggtt cagacaggcc   120
cctggcaaag aacgcgagtt cgtggctgtg atcggcagat ctgcggacc tacctactac   180
gccgactccg tgaagggcag attcaccatc tccagagaca acgccaagaa caccgtgtac   240
ctccagatga actccctgaa gcctgaggac accgccgtgt actactgtgc cggcgattgg   300
agaaactccg actctcccag caagctgaag cccgtgtacg attattgggg ccagggcacc   360
caagtgaccg tgtcctctgg aggcggaggc agtgctgagt ctaagtatgg ccctccttgt   420
cctccatgtc ctgctccaga agctgctggc gggccctccg tgtttctgtt ccctccaaag   480
cctaaggacc agctgatgat ctctcggaca cccgaagtga cctgcgtggt ggtggatgtg   540
tctcaagagg accctgaggt gcagttcaat tggtacgtgg acggcgtgga agtgcacaac   600
gccaagacca gcctagaga ggaacagttc aactccacct acagagtggt gtccgtgctg   660
accgtgctgc accaggattg gctgaacggc aaagagtaca agtgcaaggt gtccaacaag   720
ggcctgcctt ccagcatcga aaagaccatc tccaaggcca agggccagcc tagggaacct   780
caggtttaca ccctgcctcc aagccaagag gaaatgacca agaaccaggt gtccctgacc   840
tgcctggtca agggcttcta cccttccgac attgccgtgg aatgggagag caatggccag   900
cctgagaaca actacaagac cacacctcct gtgctggact ccgacggctc cttctttctg   960
tactcccgcc tgaccgtgga caagtccaga tggcaagagg gcaacgtgtt ctcctgctct  1020
gtgctgcacg aggccctgca caatcactac acccagaagt ccctcagcct gtccttggc  1080
ggaggcggtg atccgctcc tacctccagc tccaccaaga aaccccagtt gcagctggaa  1140
catctgctgc tggacctcca gatgatcctg aatggcatca caattacaa gaaccccaag  1200
ctgaccgcca tgctgaccgc taagttctac atgcccaaga aggccaccga gctgaagcac  1260
ctccagtgcc tggaacggga actgaagcct ctggaagagg tgctgaatct ggcccagtcc  1320
aagaacttcc acctgaggcc tcgggacctg atctccaaca tcaacgtgat cgtgctgaa  1380
ctcaagggct ccgagacaac cttcatgtgc gagtacgccg acgagacagc taccatcgtg  1440
gaatttctga tcggtggat caccttctgc cagtccatca tcagcaccct gacc          1494

SEQ ID NO: 36       moltype = DNA  length = 1806
FEATURE             Location/Qualifiers
misc_feature        1..1806
                    note = nucleotides coding for heavy chain of anti-hCD73
                        (hIgG4Fc)conjugated with hIL2v3 and signal peptide
            source  1..1806
                    mol_type = other DNA
                    organism = synthetic construct
SEQUENCE: 36
atggaatggt cctgggtgtt cctgttcttc ctgtccgtga ccaccggcgt gcactctcag    60
gttcagttgg ttcagtctgg cgccgaagtg aagaaaccg gctcctctgt gaaggtgtcc   120
```

```
tgcaagtttt ccggcggctc ctttacctcc tacagcttct cctgggtccg acaggctcct    180
ggacaaggct tggagtggat gggcagaatc atccccgtgc tgaccaccac cgattacgcc    240
cagaaattcc gggacagagt gaccatcacc gccgacgagt ctacctccac cgcctacatg    300
gaactgtccg gcctgagatc tgaggacacc gccgtgtact actgtgccag cggcctgaag    360
aagaactggt acttcgacct gtggggcaga ggcgctctga tcacagtgtc ctccgcttcc    420
accaagggac ccagcgtgtt ccctctggct ccttgctcca gatccacctc cgagtctaca    480
gctgctctgg gctgtctggt caaggactac ttccctgagc tgtgaccgt gtcttggaac    540
tctggcgctc tgacatctgg cgtgcacacc tttccagctg tgctccagtc ctccggcctg    600
tactctctgt ctagcgtcgt gaccgtgcct cctctagcc tgggcaccaa gacctacacc    660
tgtaatgtgg accacaagcc ttccaacacc aaggtggaca agcgcgtgga atctaagtac    720
ggccctcctt gtcctccatg tcctgctcca gaagctgctg gcggcccttc cgtgtttctg    780
ttccctccaa agcctaagga ccagctgatg atctctcgga cccctgaagt gacctgcgtg    840
gtggtggatg tgtcccaaga ggaccctgag gtgcagttca attggtacgt ggacggcgtg    900
gaagtgcaca acgccaagac caagcctaga gaggaacagt tcaactccac ctacagagtg    960
gtgtccgtgc tgaccgtgct gcaccaggat tggctgaacg gcaaagagta caagtgcaag   1020
gtgtccaaca agggcctgcc ttccagcatc gaaaagacca ctctaaggc taagggcag   1080
cctcgcgagc cccaggttta cacattgcct ccaagccaag aggaaatgac caagaaccag   1140
gtgtccctga cctgcctcgt gaagggcttc tacccttccg acattgccgt ggaatgggag   1200
tccaatggcc agcctgagaa caactacaag acaaccctc tgtgctgga ctccgacggc   1260
tccttctttc tgtattcccg cctgaccgtg acaagtcta ggtggcaaga gggcaacgtg   1320
ttctcctgct ctgtgctgca cgaggccctg cacaatcact acacccagaa gtctctgtct   1380
ctgtccctg gcgaggcgg aggatccgct cctacctcca gctccaccaa gaaaaccag   1440
ttgcagctgg aacatctgct gctggacctc cagatgatcc tgaatggcat caacaattac   1500
aagaacccca gctgaccgc catgctgacc gctaagttct acatgcccaa gaaggccacc   1560
gagctgaagc acctccagtg cctggaacgg aactgaagc ctctgaaga ggtgctgaat   1620
ctggccagt ccaagaactt ccacctgagg cctcgggag cctgatctc aacatcaac   1680
atcgtgctgg aactcaaggg ctccgagaca accttcatgt gcgagtacgc cgacgagaca   1740
gctaccatcg tggaatttct gaatcggtgg atcaccttcg ccagtccat catcagcacc   1800
ctgacc                                                              1806

SEQ ID NO: 37         moltype = DNA   length = 1749
FEATURE               Location/Qualifiers
misc_feature          1..1749
                      note = nucleotides coding for heavy chain of anti-hCD73
                      (hIgG4Fc)conjugated with hIL2v3
source                1..1749
                      mol_type = other DNA
                      organism = synthetic construct
SEQUENCE: 37
caggttcagt tggttcagtc tggcgccgaa gtgaagaaac ccggctcctc tgtgaaggtg     60
tcctgcaagt tttccggcgg ctcctttacc tcctacagct tctcctgggt ccgacaggct    120
cctgacaag gcttggagtg gatgggcaga atcatcccg tgctgaccac caccgattac    180
gcccagaaat tccggggacag agtgaccatc accgccgact gtctacctc caccgcctac    240
atggaactgt ccggcctgag atctgaggac accgccgtgt actactgtgc cagcggcctg    300
aagaagaact ggtacttcga cctgtggggc agaggcgctc tgatcacagt gcctccgct    360
tccaccaagg gacccagcgt gttccctctg gctccttgct ccagatccac ctccgagtct    420
acagctgctc tgggctgtct ggtcaaggac tactcccctg agctgtgac cgtgtcttgg    480
aactctggcg ctctgacatc tggcgtgcac accttccag ctgtgctcca gtcctccggc    540
ctgtactctc tgtctagcgt cgtgaccgtg cctcctcta gctgggcac aagaccac    600
acctgtaatg tggaccacaa gccttccaac accaaggtgg acaagcgcgt ggaatctaag    660
tacggcccct cttgtcctcc atgtcctgct ccagaagctg ctggcggccc ttccgtgttt    720
ctgttccctc caaagcctaa ggaccagctg atgatctctc ggaccctga agtgacctgc    780
gtggtggtgg atgtgtccca agaggaccct gaggtgcagt tcaattggta cgtggacggc    840
gtggaagtgc acaacgccaa gaccaagcct agaggaac agttcaact cacctacaga    900
gtgtgtccg tgctgaccgt gctgcaccag gattggctga cggcaaaga gtacaagtgc    960
aaggtgtcca caagggcct gccttccagc atcgaaaaga ccatctctaa ggctaagggc   1020
cagcctcgcg agccccaggt ttacacattg cctccaagcc aagaggaaat gaccaagaac   1080
caggtgtccc tgacctgcct cgtgaagggc ttctacccctt ccgacattgc cgtggaatgg   1140
gagtccaatg gccagcctga gaacaactac aagacaaccc tcctgtgctg gactccgac    1200
ggctccttct ttctgtattc ccgcctgacc gtgacaagt ctaggtggca gagggcaac   1260
gtgttctcct gctctgtgct gcacgaggcc ctgcacaatc actacaccca gaagtctctg   1320
tctctgtccc ttggcggagg cggaggatcc gctcctacct ccagctccac caagaaaacc   1380
cagttgcagc tggaacatct gctgctggac ctccagatga tcctgaatgg catcaacaat   1440
tacaagaacc ccaagctgac cgccatgctg accgctaagt tctacatgcc caagaaggcc   1500
accgagctga gcacctcca gtgcctggaa cgggaactga gcctctgga gaggtgctg    1560
aatctggcccc agtccaagaa cttccacctg aggcctcggg acctgatctc aacatcaac   1620
gtgatcgtgc tggaactcaa gggctccgag acaaccttca tgtgcgagta cgccgacgag   1680
acagctacca tcgtggaatt tctgaatcgg tggatcaccct tctgccagtc catcatcagc   1740
accctgacc                                                           1749

SEQ ID NO: 38         moltype = DNA   length = 699
FEATURE               Location/Qualifiers
misc_feature          1..699
                      note = nucleotides coding for light chain of anti-hCD73
                      (hIgG4Fc)conjugated with hIL2v3 and signal peptide
source                1..699
                      mol_type = other DNA
                      organism = synthetic construct
SEQUENCE: 38
```

```
atggaatggt cctgggtgtt cctgttcttc ctgtccgtga ccaccggcgt gcactccgac    60
attcagatga cccagtctcc atccttcctg agcgcctctg tgggcgacag agtgaccatt   120
acctgtcagg ccagccagga catctcccac tacctgaact ggtatcagca gaagcccggc   180
aaggccccta agctgctgat ctacgatgcc tcctctctgg aaactggcgt gccctccaga   240
ttctccggct ctggctctgg caccagcttt accctgacca tctctagcct ccagcctgag   300
gacttcgcca cctactactg ccagcagtac gacgacttcc cactgacctt ggcggaggc   360
accaaggtgg acatcaagag atctgtggcc gctccttccg tgttcatctt cccaccttcc   420
gacgagcagc tgaagtccgg cacagcttct gtcgtgtgcc tgctgaacaa cttctaccct   480
cgggaagcca aggtgcagtg gaaagtggat aacgccctcc agtccggcaa ctcccaagag   540
tctgtgaccg agcaggactc caaggacagc acctacagcc tgtcctccac actgaccctg   600
tccaaggccg actacgagaa gcacaaggtg tacgcctgcg aagtgaccca tcagggcctg   660
tctagccctg tgaccaagtc tttcaaccgg ggcgagtgt                          699

SEQ ID NO: 39          moltype = DNA  length = 642
FEATURE                Location/Qualifiers
misc_feature           1..642
                       note = nucleotides coding for light chain of anti-hCD73
                       (hIgG4Fc)conjugated with hIL2v3
source                 1..642
                       mol_type = other DNA
                       organism = synthetic construct
SEQUENCE: 39
gacattcaga tgacccagtc tccatccttc ctgagcgcct ctgtgggcga cagagtgacc    60
attacctgtc aggccagcca ggacatctcc cactacctga actggtatca gcagaagccc   120
ggcaaggccc ctaagctgct gatctacgat gcctcctctc tggaaactgg cgtgccctcc   180
agattctccg gctctggctc tggcaccagc tttaccctga ccatctctag cctccagcct   240
gaggacttcg ccacctacta ctgccagcag tacgacgact cccactgac ctttggcgga   300
ggcaccaagg tggacatcaa gagatctgtg gccgctcctt ccgtgttcat cttcccacct   360
tccgacgagc agctgaagtc cggcacagct tctgtcgtgt gcctgctgaa caacttctac   420
cctcgggaag ccaaggtgca gtggaaagtg gataacgccc tccagtccgg caactcccaa   480
gagtctgtga ccgagcagga ctccaaggac agcacctaca gcctgtcctc cacactgacc   540
ctgtccaagg ccgactacga gaagcacaag gtgtacgcct gcgaagtgac ccatcagggc   600
ctgtctagcc ctgtgaccaa gtctttcaac cggggcgagt gt                      642

SEQ ID NO: 40          moltype = AA  length = 133
FEATURE                Location/Qualifiers
REGION                 1..133
                       note = hIL-2
source                 1..133
                       mol_type = protein
                       organism = synthetic construct
SEQUENCE: 40
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 41          moltype = AA  length = 574
FEATURE                Location/Qualifiers
REGION                 1..574
                       note = hCD73
source                 1..574
                       mol_type = protein
                       organism = synthetic construct
SEQUENCE: 41
MCPRAARAPA TLLLALGAVL WPAAGAWELT ILHTNDVHSR LEQTSEDSSK CVNASRCMGG    60
VARLFTKVQQ IRRAEPNVLL LDAGDQYQGT IWFTVYKGAE VAHFMNALRY DAMALGNHEF   120
DNGVEGLIEP LLKEAKFPIL SANIKAKGPL ASQISGLYLP YKVLPVGDEV VGIVGYTSKE   180
TPFLSNPGTN LVFEDEITAL QPEVDKLKTL NVNKIIALGH SGFEMDKLIA QKVRGVDVVV   240
GGHSNTFLYT GNPPSKEVPA GKYPFIVTSD DGRKVPVVQA YAFGKYLGYL KIEFDERGNV   300
ISSHGNPILL NSSIPEDPSI KADINKWRIK LDNYSTQELG KTIVYLDGSS QSCRFRECNM   360
GNLICDAMIN NNLRHTDEMF WNHVSMCILN GGGIRSPIDE RNNGTITWEN LAAVLPFGGT   420
FDLVQLKGST LKKAFEHSVH RYGQSTGEFL QVGGIHVVYD LSRKPGDRVV KLDVLCTKCR   480
VPSYDPLKMD EVYKVILPNF LANGGDGFQM IKDELLRHDS GDQDINVVST YISKMKVIYP   540
AVEGRIKFST GSHCHGSFSL IFLSLWAVIF VLYQ                               574

SEQ ID NO: 42          moltype = DNA  length = 1392
FEATURE                Location/Qualifiers
misc_feature           1..1392
                       note = nucleotides coding for heavy chain of anti-hCD73
                       (hIgG4Fc)conjugated with signal peptide
source                 1..1392
                       mol_type = other DNA
                       organism = synthetic construct
SEQUENCE: 42
atggaatggt cctgggtgtt cctgttcttc ctgtccgtga ccaccggcgt gcactctcag    60
gttcagttgg ttcagtctgg cgccgaagtg aagaaacccg gctcctctgt gaaggtgtcc   120
tgcaagtttt ccgcgggctc ctttacctcc tacagcttct cctgggtccg acaggctcct   180
ggacaaggct tggagtggat gggcagaatc atccccgtgc tgaccaccac cgattacgcc   240
cagaaattcc gggacagagt gaccatcacc gccgacgagt ctaccaccac cgcctacatg   300
```

```
gaactgtccg gcctgagatc tgaggacacc gccgtgtact actgtgccag cggcctgaag    360
aagaactggt acttcgacct gtggggcaga ggcgctctga tcacagtgtc ctccgcttcc    420
accaagggac ccagcgtgtt ccctctggct ccttgctcca gatccacctc cgagtctaca    480
gctgctctgg gctgtctggt caaggactac ttccctgagc ctgtgaccgt gtcttggaac    540
tctggcgctc tgacatctgg cgtgcacacc tttccagtgc tgctccagtc ctccggcctg    600
tactctctgt ctagcgtcgt gaccgtgcct tcctctagcc tgggcaccaa gacctacacc    660
tgtaatgtgg accacaagcc ttccaacacc aaggtggaca agcgcgtgga atctaagtac    720
ggccctcctt gtcctccatg tcctgctcca gaagctgctg gcggcccttc cgtgtttctg    780
ttccctccaa agcctaagga ccagctgatg atctctcgga ccctgaagt gacctgcgtg    840
gtggtggatg tgtcccaaga ggaccctgag gtgcagttca attggtacgt ggacggcgtg    900
gaagtgcaca acgccaagac caagcctaga gaggaacagt tcaactccac ctacagagtg    960
gtgtccgtgc tgaccgtgct gcaccaggat tggctgaacg gcaaagagta caagtgcaag   1020
gtgtccaaca agggcctgcc ttccagcatc gaaaagacca tctctaaggc taagggccag   1080
cctcgcgagc cccaggttta cacattgcct ccaagccaag aggaaatgac caagaaccag   1140
gtgtccctga cctgcctcgt gaagggcttc taccctccg acattgccgt ggaatgggag   1200
tccaatggcc agcctgagaa caactacaag acaaccctc ctgtgctgga ctccgacggc   1260
tccttctttc tgtattccg cctgaccgtg gacaagtcta ggtggcaaga gggcaacgtg   1320
ttctcctgct ctgtgctgca cgaggccctg cacaatcact acacccagaa gtctctgtct   1380
ctgtcccttg gc                                                        1392

SEQ ID NO: 43          moltype = DNA  length = 1098
FEATURE                Location/Qualifiers
misc_feature           1..1098
                       note = nucleotides coding for light chain of hIgG4Fc
                         conjugated withhIL2v3 and signal peptide
source                 1..1098
                       mol_type = other DNA
                       organism = synthetic construct
SEQUENCE: 43
gaatctaagt acggccctcc ttgtcctcca tgtcctgctc cagaagctgc tggcggccct     60
tccgtgtttc tgttccctcc aaagcctaag gaccagctga tgatctctcg gacccctgaa   120
gtgacctgcg tggtggtgga tgtgtcccaa gaggaccctg aggtgcagtt caattggtac   180
gtggacggcg tggaagtgca caacgccaag accaagccta gaggaacaga gttcaactcc   240
acctacagag tggtgtccgt gctgaccgtg ctgcaccagg attggctgaa cggcaaagag   300
tacaagtgca aggtgtccaa caagggcctg ccttccagca tcgaaaagac catctctaag   360
gctaagggcc agcctcgcga gccccaggtt tacacattgc ctccaagcca agaggaaatg   420
accaagaacc aggtgtccct gacctgcctc gtgaagggct ctacccttc gacattgcc    480
gtggaatggg agtccaatgg ccagcctgag aacaactaca agacaacccc tcctgtgctg   540
gactccgacg gctccttctt tctgtattcc cgcctgaccg tggacaagtc taggtggcaa   600
gagggcaacg tgttctcctg ctctgtgctg cacgaggccc tgcacaatca ctacacccag   660
aagtctctgt ctctgtccct tggcggaggc ggaggatccg ctcctacctc cagctccacc   720
aagaaaaccc agttgcagct ggaacatctg ctgctggacc tccagatgat cctgaatggc   780
atcaacaatt acaagaaccc caagctgacc gccatgctga ccgctaagtt ctacatgccc   840
aagaaggcca ccgagctgaa gcacctccag tgcctggaac gggaactgaa gcctctggaa   900
gaggtgctga atctggccca gtccaagaac ttccacctga ggcctcggga cctgatctcc   960
aacatcaacg tgatcgtgct ggaactcaag ggctccgaga caaccttcat gtgcgagtac  1020
gccgacgaga cagctaccat cgtggaattt ctgaatcggt ggatcacctt ctgccagtcc  1080
atcatcagca ccctgacc                                                1098
```

FUSION PROTEIN COMPRISING ANTI-CD73 ANTIBODY AND IL-2, AND USE THEREOF

CROSS REFERENCE TO RELATED APPLICATIONS

This application is a Bypass Continuation Application of International Application No. PCT/KR2023/008664, filed on Jun. 22, 2023, which claims priority to Korean Patent Application No. 10-2022-0076279, filed on Jun. 22, 2022, the disclosures of which are incorporated by reference herein their entireties.

INCORPORATION BY REFERENCE OF SEQUENCE LISTING

The content of the electronically submitted sequence listing, file name: Q301220_SEQ_LIS_AS_FILED.xml; size: 71.2 KB; and date of creation: Aug. 23, 2024, filed herewith, is incorporated herein by reference in its entirety.

TECHNICAL FIELD

The present invention relates to a fusion protein in which an anti-CD73 antibody or an antigen-binding fragment thereof and IL-2 are linked to each other, and the use thereof.

BACKGROUND ART

Cancer immunotherapy is a method of treating cancer using the body's immune system. It can induce the immune system to attack cancer cells by targeting antigens such as cancer cell surface proteins and can increase the activity of immune cells by controlling the tumor microenvironment that causes immune evasion of cancer cells.

The tumor microenvironment is an environment in which not only cancer cells, but also fibroblasts, blood vessels, lymphatic vessels, immune cells, extracellular matrix, and adipocytes, which exist in cancer tissues, proliferate and evolve. In this regard, studies have reported that the ATP-AMP-adenosine-A2AR/A2BR signaling pathway can regulate the activity of immune cells in the tumor microenvironment (S. Vigano et al., Front Immunol (2019) 10:925). Specifically, when adenosine binds to the A2AR/A2BR receptor on the surface of tumor cells or immune cells, immune suppressor cells such as regulatory T cells or tumor-associated macrophages (TAMs) are activated, and the activity of cytotoxic T cells and NK cells is inhibited. In this regard, studies have been conducted on a method of activating immunity in the tumor microenvironment by inhibiting this signaling pathway by treatment with a substance that target CD39, an ectonucleotidase that converts ATP to AMP, CD73, an ectonucleotidase that converts AMP to adenosine, or A2AR/A2BR receptors that bind to adenosine.

Meanwhile, interleukin 2 (IL-2), also called T-cell growth factor (TCGF), is a globular glycoprotein that plays a central role in the production, survival, and homeostasis of lymphocytes. IL-2 mediates various immune actions by binding to an IL-2 receptor composed of three distinct subunits.

In addition, IL-2 is synthesized mainly by activated T cells, particularly CD4+ helper T cells. IL-2 stimulates the proliferation and differentiation of T cells and induces the production of cytotoxic T lymphocytes (CTLs) and the differentiation of peripheral blood lymphocytes into cytotoxic cells and lymphokine-activated killer cells (LAK cells).

Throughout the present specification, a number of publications and patent documents are referred to and cited. The disclosure of these cited publications and patent documents is incorporated herein by reference in its entirety to more clearly describe the state of the art to which the present invention pertains and the content of the present invention.

DISCLOSURE

Technical Problem

Accordingly, the present inventors have conducted studies to develop a new combination of proteins as a fusion protein that enhances the activity of immune cells by controlling the tumor microenvironment. As a result, they have discovered that a fusion protein dimer comprising an anti-CD73 antibody or an antigen-binding fragment thereof and IL-2 can control the tumor microenvironment and effectively activates immune cells. Based on this finding, the present inventors have demonstrated that the fusion protein dimer is effective as an anticancer agent, thereby completing the present invention.

Technical Solution

To achieve the above object, one aspect of the present invention provides a fusion protein comprising: an antibody or a fragment thereof that specifically binds to CD73; and IL-2.

Another aspect of the present invention provides a fusion protein dimer in which the two fusion proteins are linked to each other.

Still another aspect of the present invention provides a polynucleotide encoding the fusion protein, an expression vector containing the polynucleotide, and a transformed cell into which the expression vector has been introduced.

Yet another aspect of the present invention provides a method for producing a fusion protein dimer comprising: an antibody or an antigen-binding fragment thereof that specifically binds to CD73; and IL-2, the method comprising steps of: i) culturing the transformed cell; and ii) collecting the fusion protein dimer.

Still yet another aspect of the present invention provides a pharmaceutical composition for preventing or treating cancer comprising the fusion protein or the fusion protein dimer as an active ingredient.

A further aspect of the present invention provides a method for preventing or treating cancer, comprising a step of administering the fusion protein or the fusion protein dimer to a subject.

Another further aspect of the present invention provides the use of the fusion protein or the fusion protein dimer for preventing or treating cancer.

Advantageous Effects

The fusion protein or dimer thereof according to the present invention, which comprises an anti-CD73 antibody or an antigen-binding fragment thereof and IL-2, is able to inhibit adenosine production (ATP→AMP→adenosine) by binding to CD73 in cancer cells. This inhibition blocks the A2AR and A2BR signaling pathways, thereby controlling the tumor microenvironment. Furthermore, the fusion protein or dimer thereof is able to activate immune cells (CD8+ T cells and CD4+ T cells) along with less activation of immunosuppressive cells such as regulatory T cells (Tregs). In addition, IL-2 or a variant thereof in the fusion protein of the present invention is able to activate immune cells. Therefore, the fusion protein and dimer thereof of the present invention may be useful for the prevention or treatment of cancer.

BEST MODE

Figure 1:
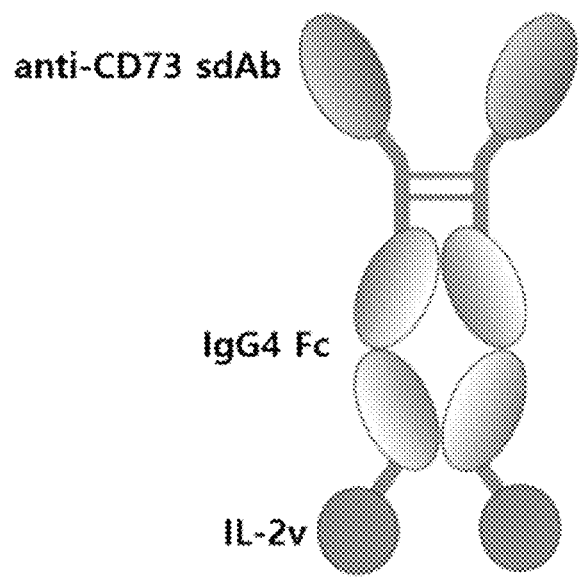
FIG. 1 schematically illustrates the structure of a fusion protein dimer (GI-108A1), which is an example.
Figure 2:
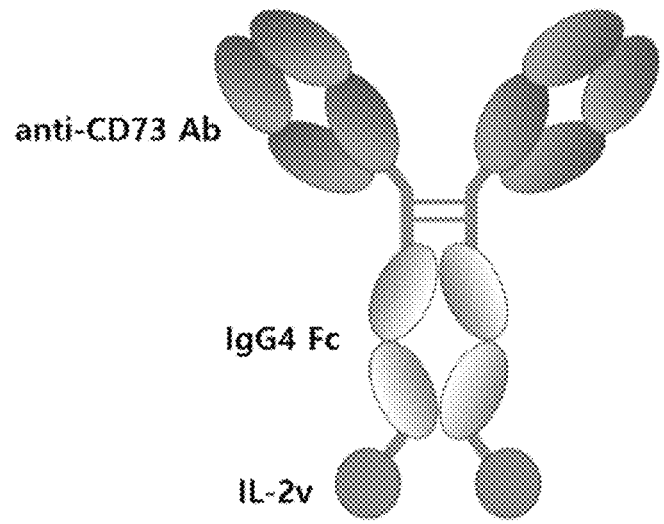
FIG. 2 schematically illustrates the structure of a fusion protein dimer (GI-108B1), which is an example.

Fusion Protein Comprising: Antibody or Antigen-Binding Fragment Thereof that Specifically Binds to CD73; and IL-2

One aspect of the present invention provides a fusion protein comprising: an antibody or an antigen-binding fragment thereof that specifically binds to CD73; and IL-2.

CD73 and Antibody or Antigen-Binding Fragment Thereof that Specifically Binds to CD73

As used in the present specification, the term "CD73 (Cluster of Differentiation 73)" refers to an ectonucleotidase that catalyzes the dephosphorylation of 5' nucleotides, primarily converting adenosine monophosphate (AMP) to adenosine. CD73 forms a homodimer on the cell membrane via a GPI anchor. Each monomer is 65 kDa, with its N-terminal and C-terminal domains connected by a flexible helical linker.

It is known that CD73 is involved in the production of adenosine, is overexpressed in cancer cells, and induces immunosuppression. CD73 is expressed in many tumor cells, including leukemia, bladder cancer, glioma, glioblastoma, ovarian cancer, melanoma, prostate cancer, thyroid cancer, esophageal cancer, and breast cancer. In addition, CD73 is known to be expressed on the surface of immunosuppressive cells (including regulatory T cells (Tregs) and myeloid-derived suppressor cells (MDSCs)). In particular, overexpression of CD73 has been reported to be associated with angiogenesis, invasion, resistance to chemotherapy, tumor metastasis, and short survival time of cancer patients with various tumors, including breast cancer and melanoma.

In the present invention, CD73 may be mammalian CD73, preferably human CD73, without limitation. In addition, in the present invention, the CD73 protein includes, but is not limited to, both native and mutant CD73 proteins. The native CD73 protein generally refers to a polypeptide comprising the amino acid sequence of the native CD73 protein, and the amino acid sequence of the native CD73 protein generally refers to the amino acid sequence found in naturally occurring CD73. Information about CD73 is available from known databases such as GenBank of the National Institutes of Health. For example, CD73 may have the amino acid sequence (SEQ ID NO: 41) corresponding to GenBank accession number NP_002517.1, but it is not limited to this sequence.

As used in the present specification, the term "antigen" refers to a molecule capable of selectively binding to an antibody. The target antigen may be a polypeptide, a carbohydrate, a nucleic acid, a lipid, a hapten, or other naturally occurring or synthetic compound. Specifically, the antigen is a polypeptide and may be a protein present on the cell surface or within the cell.

As used in the present specification, the term "specifically binds" means binding that is measurably different from a non-specific interaction. Specific binding can be determined by competition with a control molecule that is similar to the target that has no binding activity.

The antibody or antigen-binding fragment thereof that specifically binds to CD73 may generally refer to molecules capable of specifically forming an antigen-antibody complex with CD73. In addition, the antibody or antigen-binding fragment thereof may be used in any form as long as it contains an antigen-binding site capable of specifically binding to CD73. The antibody or antigen-binding fragment thereof may include other amino acids that are not directly involved in binding, or amino acids whose effects are blocked by the residues of the antigen-binding site.

As used in the present specification, the term "antibody" refers to molecules containing an antigen-binding site, and immunologically active fragments of immunoglobulin molecules containing an antigen-binding site. The immunoglobulin molecules may be immunoglobulin molecules of IgG, IgE, IgM, IgD, IgA, IgY, or a subclass thereof. The heavy and light chains of immunoglobulins may each include a constant region and a variable region. The light and heavy chain variable regions of immunoglobulins contain three variable regions, called complementarity determining regions (CDRs), and four framework regions (FRs). The CDRs are antigen-binding sites that mainly bind to the epitope of the antigen.

The antibodies or antigen-binding fragments thereof of the present invention may include monoclonal antibodies, polyclonal antibodies, synthetic antibodies, human antibodies, humanized antibodies, non-human antibodies, and any fragments thereof, as well as immunoconjugates.

As used in the present specification, the term "antigen-binding fragment of the antibody" refers to a portion of a polypeptide within the overall structure of an immunoglobulin to which an antigen can bind. Examples of the antigen-binding fragment include, but are not limited to, Fab fragments, Fab' fragments, F(ab')2 fragments, bispecific Fab dimers (Fab2), trispecific Fab trimers (Fab3), Fv, single-chain Fv proteins ("scFv"), bis-scFv (scFv)2, minibodies, diabodies, triabodies, tetrabodies, disulfide stabilized Fv proteins ("dsFv"), single-domain antibodies (sdAb), and portions of full-length antibodies responsible for antigen binding. Regardless of the structure, the fragment of the antibody is able bind to the same antigen recognized by the intact antibody.

The single-domain antibody, also called a nanobody, refers to an antibody fragment consisting of a single monomeric variable antibody domain. The single-domain antibody is able to specifically bind to a specific antigen like a whole antibody. The single-domain antibody has a molecular weight of 12 to 15 kDa, which is smaller than that of common antibodies (150-160 kDa), Fab fragments (about 50 kDa), and scFv (about 25 kDa). The single-domain antibody may be obtained, for example, by monomerizing the dimeric variable domains of human or mouse conventional immunoglobulin G (IgG), and may be VHH derived from the heavy chain antibody of Camelids, or a VNAR fragment obtained from IgNAR of Cartilaginous fishes.

IL-2 or Variant Thereof

As used in the present specification, the term "IL-2" or "interleukin-2" refers to any wild-type IL-2 obtained from any vertebrate source, including mammals such as primates (e.g., humans) and rodents (e.g., mice and rats), unless otherwise stated. IL-2 has a protein size of 15.5 kDa to 16 kDa and consists of 133 amino acids. IL-2 may be obtained from animal cells, but also includes one obtained from recombinant cells capable of producing IL-2. In addition, IL-2 may be wild-type IL-2 or a variant thereof.

In the present specification, IL-2 or a variant thereof may be collectively expressed by the term "IL-2 protein" or "IL-2 polypeptide". IL-2, an IL-2 protein, an IL-2 polypeptide, and an IL-2 variant specifically bind to, for example, an IL-2 receptor. This specific binding may be identified by methods known to those skilled in the art.

IL-2 may also be in a mature form. Specifically, the mature IL-2 may not contain a signal sequence, and may have the amino acid sequence of SEQ ID NO: 40. Here, IL-2 may be used under a concept encompassing a fragment in which a portion of the N-terminus or C-terminus of wild-type IL-2 is truncated.

As used in the present specification, the term "IL-2 variant" refers to a form in which a portion of the amino acids in the full-length IL-2 or the above-described fragment of IL-2 is substituted. That is, an IL-2 variant may have an amino acid sequence different from wild-type IL-2 or a fragment thereof. However, the IL-2 variant may have activity equivalent or similar to the wild-type IL-2. Here, "IL-2 activity" may, for example, refer to specific binding to an IL-2 receptor, in which the specific binding can be measured by methods known to those skilled in the art.

Specifically, the IL-2 variant may be obtained by substitution of a portion of the amino acids in the wild-type IL-2. An embodiment of the IL-2 variant obtained by amino acid substitution may be obtained by substitution of at least one of the $38^{th}$, $42^{nd}$, $45^{th}$, $61^{st}$, and $72^{nd}$ amino acids in the amino acid sequence of SEQ ID NO: 40.

Specifically, the IL-2 variant may be obtained by substituting at least one of the $38^{th}$, $42^{nd}$, $45^{th}$, $61^{st}$, and $72^{nd}$ amino acids in the amino acid sequence of SEQ ID NO: 40 with another amino acid. In addition, when IL-2 is in a form in which a portion of the N-terminus in the amino acid sequence of SEQ ID NO: 40 is truncated, the amino acid at a position complementarily corresponding to that in the amino acid sequence of SEQ ID NO: 40 may be substituted with another amino acid. According to one embodiment, one, two, three, four, five, six, seven, eight, nine, or ten amino acids may be substituted as long as such an IL-2 variant maintains IL-2 activity. According to another embodiment, one to five amino acids may be substituted.

In one embodiment, the IL-2 variant may be in a form in which the amino acids at two positions are substituted. Specifically, the IL-2 variant may be obtained by substitution of the $38^{th}$ and $42^{nd}$ amino acids in the amino acid sequence of SEQ ID NO: 40. In addition, in one embodiment, the IL-2 variant may be obtained by substitution of the $38^{th}$ and $45^{th}$ amino acids in the amino acid sequence of SEQ ID NO: 40. In addition, in one embodiment, the IL-2 variant may be obtained by substitution of the $38^{th}$ and $61^{st}$ amino acids in the amino acid sequence of SEQ ID NO: 40. In addition, in one embodiment, the IL-2 variant may be obtained by substitution of the $38^{th}$ and $72^{nd}$ amino acids in the amino acid sequence of SEQ ID NO: 40. In addition, in one embodiment, the IL-2 variant may be obtained by substitution of the $42^{nd}$ and $45^{th}$ amino acids in the amino acid sequence of SEQ ID NO: 40. In addition, in one embodiment, the IL-2 variant may be obtained by substitution of the $42^{nd}$ and $61^{st}$ amino acids in the amino acid sequence of SEQ ID NO: 40. In addition, in one embodiment, the IL-2 variant may be obtained by substitution of the $42^{nd}$ and $72^{nd}$ amino acids in the amino acid sequence of SEQ ID NO: 40. In addition, in one embodiment, the IL-2 variant may be obtained by substitution of the $45^{th}$ and $61^{st}$ amino acids in the amino acid sequence of SEQ ID NO: 40. In addition, in one embodiment, the IL-2 variant may be obtained by substitution of the $45^{th}$ and $72^{nd}$ amino acids in the amino acid sequence of SEQ ID NO: 40. In addition, in one embodiment, the IL-2 variant may be obtained by substitution of the $61^{st}$ and $72^{nd}$ amino acids in the amino acid sequence of SEQ ID NO: 40.

Furthermore, the IL-2 variant may be in a form in which the amino acids at three positions are substituted. Specifically, the IL-2 variant may be obtained by substitution of the $38^{th}$, $42^{nd}$, and $45^{th}$ amino acids in the amino acid sequence of SEQ ID NO: 40. In addition, in one embodiment, the IL-2 variant may be obtained by substitution of the $38^{th}$, $42^{nd}$, and $61^{st}$ amino acids in the amino acid sequence of SEQ ID NO: 40. In addition, in one embodiment, the IL-2 variant may be obtained by substitution of the $38^{th}$, $42^{nd}$, and $72^{nd}$ amino acids in the amino acid sequence of SEQ ID NO: 40. In addition, in one embodiment, the IL-2 variant may be obtained by substitution of the $38^{th}$, $45^{th}$, and $61^{st}$ amino acids in the amino acid sequence of SEQ ID NO: 40. In addition, in one embodiment, the IL-2 variant may be obtained by substitution of the $38^{th}$, $45^{th}$, and $72^{nd}$ amino acids in the amino acid sequence of SEQ ID NO: 40. In addition, in one embodiment, the IL-2 variant may be obtained by substitution of the $38^{th}$, $61^{st}$, and $72^{nd}$ amino acids in the amino acid sequence of SEQ ID NO: 40. In addition, in one embodiment, the IL-2 variant may be obtained by substitution of the $42^{nd}$, $45^{th}$, and $61^{st}$ amino acids in the amino acid sequence of SEQ ID NO: 40. In addition, in one embodiment, the IL-2 variant may be obtained by substitution of the $42^{nd}$, $45^{th}$, and $72^{nd}$ amino acids in the amino acid sequence of SEQ ID NO: 40. In addition, in one embodiment, the IL-2 variant may be obtained by substitution of the $45^{th}$, $61^{st}$, and $72^{nd}$ amino acids in the amino acid sequence of SEQ ID NO: 40.

Here, the "another amino acid" introduced by substitution may be any one selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine. However, regarding amino acid substitution for the IL-2 variant, in the amino acid sequence of SEQ ID NO: 40, the $38^{th}$ amino acid cannot be substituted with arginine, the $42^{nd}$ amino acid cannot be substituted with phenylalanine, the $45^{th}$ amino acid cannot be substituted with tyrosine, the $61^{st}$ amino acid cannot be substituted with glutamic acid, and the $72^{nd}$ amino acid cannot be substituted with leucine.

Regarding amino acid substitution for the IL-2 variant, in the amino acid sequence of SEQ ID NO: 40, the $38^{th}$ amino acid, arginine, may be substituted with an amino acid other than arginine. Preferably, regarding amino acid substitution for an IL-2 variant, in the amino acid sequence of SEQ ID NO: 40, the $38^{th}$ amino acid, arginine, may be substituted with alanine (R38A).

Regarding amino acid substitution for the IL-2 variant, in the amino acid sequence of SEQ ID NO: 40, the $42^{nd}$ amino acid, phenylalanine, may be substituted with an amino acid other than phenylalanine. Preferably, regarding amino acid substitution for the IL-2 variant, in the amino acid sequence of SEQ ID NO: 40, the $42^{nd}$ amino acid, phenylalanine, may be substituted with alanine (F42A).

Regarding amino acid substitution for the IL-2 variant, in the amino acid sequence of SEQ ID NO: 40, the $45^{th}$ amino acid, tyrosine, may be substituted with an amino acid other than tyrosine. Preferably, regarding amino acid substitution for the IL-2 variant, in the amino acid sequence of SEQ ID NO: 40, the $45^{th}$ amino acid, tyrosine, may be substituted with alanine (Y45A).

Regarding amino acid substitution for the IL-2 variant, in the amino acid sequence of SEQ ID NO: 40, the $61^{st}$ amino acid, glutamic acid, may be substituted with an amino acid other than glutamic acid. Preferably, regarding amino acid substitution for the IL-2 variant, in the amino acid sequence of SEQ ID NO: 40, the 61$^{st}$ amino acid, glutamic acid, may be substituted with arginine (E61R).

Regarding amino acid substitution for an IL-2 variant, in the amino acid sequence of SEQ ID NO: 40, the 72$^{nd}$ amino acid, leucine, may be substituted with an amino acid other than leucine. Preferably, regarding amino acid substitution for an IL-2 variant, in the amino acid sequence of SEQ ID NO: 40, the 72$^{nd}$ amino acid, leucine, may be substituted with glycine (L72G).

Specifically, the IL-2 variant may be obtained by at least one substitution selected from the group consisting of R38A, F42A, Y45A, E61R, and L72G, in the amino acid sequence of SEQ ID NO: 40.

Specifically, the IL-2 variant may be obtained by two or three amino acid substitutions selected from the group consisting of R38A, F42A, Y45A, E61R, and L72G.

In addition, the IL-2 variant may be in a form in which the amino acids at two positions are substituted. Specifically, the IL-2 variant may be obtained by the substitutions R38A and F42A. In addition, in one embodiment, the IL-2 variant may be obtained by the substitutions R38A and Y45A. In addition, in one embodiment, the IL-2 variant may be obtained by the substitutions R38A and E61R. In addition, in one embodiment, the IL-2 variant may be obtained by the substitutions R38A and L72G. In addition, in one embodiment, the IL-2 variant may be obtained by the substitutions F42A and Y45A. In addition, in one embodiment, the IL-2 variant may be obtained by the substitutions F42A and E61R. In addition, in one embodiment, the IL-2 variant may be obtained by the substitutions F42A and L72G. In addition, in one embodiment, the IL-2 variant may be obtained by the substitutions E61R and L72G.

Furthermore, the IL-2 variant may be in a form in which the amino acids at three positions are substituted. Specifically, the IL-2 variant may be obtained by the substitutions R38A, F42A, and Y45A. In addition, in one embodiment, the IL-2 variant may be obtained by the substitutions R38A, F42A, and E61R. In addition, in one embodiment, the IL-2 variant may be obtained by the substitutions R38A, F42A, and L72G. In addition, in one embodiment, the IL-2 variant may be obtained by the substitutions R38A, Y45A, and E61R. In addition, in one embodiment, the IL-2 variant may be obtained by the substitutions R38A, Y45A, and L72G. In addition, in one embodiment, the IL-2 variant may be obtained by the substitutions F42A, Y45A, and E61R. In addition, in one embodiment, the IL-2 variant may be obtained by the substitutions F42A, Y45A, and L72G. In addition, in one embodiment, the IL-2 variant may be obtained by the substitutions F42A, E61R, and L72G. In addition, in one embodiment, the IL-2 variant may be obtained by the substitutions Y45A, E61R, and L72G.

In addition, the IL-2 variant may be in a form in which the amino acids at four positions are substituted. Specifically, the IL-2 variant may be obtained by the substitutions R38A, F42A, Y45A, and E61R. In addition, in one embodiment, the IL-2 variant may be obtained by the substitutions R38A, F42A, Y45A, and L72G. In addition, in one embodiment, the IL-2 variant may be obtained by the substitutions R38A, F42A, E61R, and L72G. In addition, in one embodiment, the IL-2 variant may be obtained by the substitutions R38A, Y45A, E61R, and L72G. In addition, in one embodiment, the IL-2 variant may be obtained by the substitutions F42A, Y45A, E61R, and L72G.

Furthermore, the IL-2 variant may be obtained by the substitutions R38A, F42A, Y45A, E61R, and L72G.

Preferably, the IL-2 variant of the present invention may be obtained by at least one substitution selected from the group consisting of R38A, F42A, and E61R in the amino acid sequence of SEQ ID NO: 40. More preferably, the IL-2 variant of the present invention may be obtained by the substitutions R38A, F42A, and E61R in the amino acid sequence of SEQ ID NO: 40. Specifically, the IL-2 variant of the present invention may have the amino acid sequence of SEQ ID NO: 8.

In addition, the IL-2 variant may be characterized by having low in vivo toxicity. Here, the low in vivo toxicity may be a side effect caused by binding of IL-2 to the IL-2 receptor alpha chain (IL-2Rα). IL-2 variants described in the present application have a low binding affinity for the IL-2 receptor alpha chain (IL-2Rα) and thus have lower in vivo toxicity than the wild-type IL-2.

Structure of Fusion Protein Comprising: Antibody or Antigen-Binding Fragment Thereof that Specifically Binds to CD73; and IL-2 or Variant Thereof The fusion protein of the present invention may comprise: a single-domain antibody that specifically binds to CD73; an Fc region; and IL-2 or a variant thereof. Here, the Fc region and the IL-2 or variant thereof may be linked by a linker.

Specifically, the fusion protein may comprise the following structural formula (I):

N'—X-[linker (1)]o-Fc region fragment or variant thereof-[linker (2)]p-Y—C'  (I)

in structural formula (I) above,
N' is the N-terminus,
C' is the C-terminus,
X is the antibody or antigen-binding fragment thereof that specifically binds to CD73,
Y is IL-2,
linker (1) and linker (2) are peptide linkers, and
o and p are each independently 0 or 1.

Here, the antibody or fragment thereof that specifically binds to CD73 is as described above, and IL-2 is as described above.

In one embodiment, the antigen-binding fragment may comprise a single-domain antibody. In this case, the antibody or antigen-binding fragment thereof, specifically the single-domain antibody, may comprise: a CDR1 region comprising an amino acid sequence selected from the group consisting of SEQ ID NOs: 15, 18, and 21; a CDR2 region comprising an amino acid sequence selected from the group consisting of SEQ ID NOs: 16, 19, and 22; and a CDR3 region comprising an amino acid sequence selected from the group consisting of SEQ ID NOs: 17, 20, and 23.

Specifically, the antigen-binding fragment may comprise: a CDR1 comprising the amino acid sequence of SEQ ID NO: 15, a CDR2 comprising the amino acid sequence of SEQ ID NO: 16, and a CDR3 comprising the amino acid sequence of SEQ ID NO: 17; or a CDR1 comprising the amino acid sequence of SEQ ID NO: 18, a CDR2 comprising the amino acid sequence of SEQ ID NO: 19, and a CDR3 comprising the amino acid sequence of SEQ ID NO: 20; or a CDR1 comprising the amino acid sequence of SEQ ID NO: 21, a CDR2 comprising the amino acid sequence of SEQ ID NO: 22, and a CDR3 comprising the amino acid sequence of SEQ ID NO: 23.

In one embodiment, the antigen-binding fragment may comprise any one amino acid sequence selected from the group consisting of SEQ ID NOs: 2, 3, and 4.

The peptide linker (1) may consist of 1 to 50 contiguous amino acids, or 3 to 30 contiguous amino acids, or 5 to 15 amino acids. In one embodiment, the peptide linker (1) may consist of 12 amino acids. In addition, the peptide linker 1 may contain at least one cysteine. Specifically, the peptide linker (1) may contain one, two, or three cysteines. In addition, the peptide linker (1) may be derived from the hinge of an immunoglobulin. For example, the hinge may be selected from the hinge regions of various IgG subclass antibodies. In addition, the hinge may be a form in which one or more of the amino acids in the hinge region derived from an immunoglobulin are substituted with other amino acid(s), or may be a sequence obtained by adding one or more amino acids to the hinge region. In one embodiment, the peptide linker (1) may be a peptide linker consisting of the amino acid sequence of SEQ ID NO: 5.

The peptide linker (2) may consist of 1 to 30 contiguous amino acids, or 2 to 20 contiguous amino acids, or 2 to 10 amino acids. In one embodiment, the peptide linker (2) may be (G4S)n (where n is an integer ranging from 1 to 10). In (G4S)n, n may be 1, 2, 3, 4, 5, 6, 7, 8, 9, or 10. In one embodiment, the peptide linker (2) may be a peptide linker consisting of the amino acid sequence of SEQ ID NO: 7.

The immunoglobulin Fc region refers to a protein that comprises immunoglobulin heavy chain constant region 2 (CH2) and heavy chain constant region 3 (CH3), but does not comprise immunoglobulin heavy and light chain variable regions and light chain constant region (CL). The immunoglobulin Fc region may be derived from IgG, IgA, IgE, IgD, or IgM. Specifically, the immunoglobulin Fc region may be derived from IgG1, IgG2, IgG3, or IgG4, which is a subclass of IgG. Preferably, the immunoglobulin Fc region may be derived from IgG4.

In addition, the immunoglobulin Fc region may be an Fc region variant as well as a wild-type Fc region. In addition, as used in the present specification, the term "Fc region variant" may refer to a form which is different from the wild-type Fc region in terms of glycosylation pattern, or has a high glycosylation compared to the wild-type Fc region, or has a low glycosylation compared to the wild-type Fc region, or is deglycosylated. In addition, an aglycosylated Fc region is also included. The Fc region or a variant thereof may be adapted to have an adjusted number of sialic acids, fucosylations, or glycosylations, through culture conditions or genetic manipulation of a host.

In addition, glycosylation of the immunoglobulin Fc region may be modified by conventional methods such as chemical methods, enzymatic methods, and genetic engineering methods using microorganisms. In addition, the Fc region variant may be in a mixed form of respective Fc regions of immunoglobulins, IgG, IgA, IgE, IgD, and IgM. In addition, the Fc region variant may be in a form in which some amino acids of the Fc region are substituted with other amino acids. In one embodiment, the Fc region may comprise the amino acid sequence of SEQ ID NO: 6.

In addition, the fusion protein of the present invention may be a polypeptide comprising the heavy chain variable region (VH) and heavy chain constant region 1 (CH1) of an anti-CD73 antibody, an Fc region, and IL-2 or a variant thereof. Here, the Fc region and the IL-2 or variant thereof may be linked by a linker.

In addition, the fusion protein may comprise the following structural formulas (II) and (III):

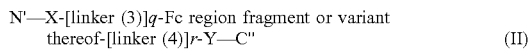

(II)

and

(III)

in structural formulas (II) and (III) above,

N' is the N-terminus,

C' is the C-terminus,

X is an antibody or an antigen-binding fragment thereof that specifically binds to CD73, and comprises a heavy chain variable region (VH) and a heavy chain constant region 1 (CH1), X' is an antibody or an antigen-binding fragment thereof that specifically binds to CD73, and comprises a light chain variable region (VL) and a light chain constant region (CL), Y is IL-2, linker (3) and linker (4) are peptide linkers, and q and r are each independently 0 or 1.

In one embodiment, the antibody or antigen-binding fragment thereof may comprise: a heavy chain variable region comprising an HCDR1 comprising the amino acid sequence of SEQ ID NO: 24, an HCDR2 comprising the amino acid sequence of SEQ ID NO: 25, and an HCDR3 comprising the amino acid sequence of SEQ ID NO: 26; and a light chain variable region comprising an LCDR1 comprising the amino acid sequence of SEQ ID NO: 27, an LCDR2 comprising the amino acid sequence (Asp-Ala-Ser (DAS)) of SEQ ID NO: 28, and an LCDR3 comprising the amino acid sequence of SEQ ID NO: 29.

In one embodiment, the heavy chain variable region may comprise the amino acid sequence of SEQ ID NO: 9. In one embodiment, the light chain variable region may comprise the amino acid sequence of SEQ ID NO: 13.

The peptide linker (3) may consist of 1 to 50 contiguous amino acids, or 3 to 30 contiguous amino acids, or 5 to 15 amino acids. In one embodiment, the peptide linker 3 may consist of 12 amino acids. In addition, the peptide linker (3) may contain at least one cysteine. Specifically, it may contain one, two, or three cysteines. In addition, the peptide linker (3) may be derived from the hinge of an immunoglobulin. For example, the hinge may be selected from the hinge regions of various IgG subclass antibodies. In addition, the hinge may be a form in which one or more of the amino acids in the hinge region derived from an immunoglobulin are substituted with other amino acid(s), or may be a sequence obtained by adding one or more amino acids to the hinge region. In one embodiment, the peptide linker (3) may be a peptide linker consisting of the amino acid sequence of SEQ ID NO: 11.

The peptide linker (4) may consist of 1 to 30 contiguous amino acids, or 2 to 20 contiguous amino acids, or 2 to 10 amino acids. In one embodiment, the peptide linker (4) may be (G4S) n (where n is an integer ranging from 1 to 10). In (G4S) n, n may be 1, 2, 3, 4, 5, 6, 7, 8, 9, or 10. In one embodiment, the peptide linker (4) may be a peptide linker consisting of the amino acid sequence of SEQ ID NO: 12.

The "Fc region fragment or variant thereof" used in this embodiment is as described above.

Fusion Protein Dimer

Another aspect of the present invention provides a dimer obtained by linking two fusion proteins, each comprising: an antibody or an antigen-binding fragment thereof that specifically binds to CD73; and IL-2 or a variant thereof. The antibody or antigen-binding fragment thereof that specifically binds to CD73 is as described above, and IL-2 is also as described above. Here, the linkage between the fusion proteins constituting the dimer may be achieved by a disulfide bond formed by cysteines present in the linker, without being limited thereto. The fusion proteins constituting the dimer may be the same proteins, resulting in a homodimer.

Specifically, in one embodiment, the dimer may be a dimer in which two fusion proteins, each comprising a single-domain antibody that specifically binds to CD73, an Fc region, and IL-2 or a variant thereof, are linked to each other by a disulfide bond formed by cysteines. In addition, in one embodiment, the dimer may be a dimer in which two fusion proteins, each comprising a polypeptide comprising the heavy chain variable region (VH) and heavy chain constant region 1 (CH1) of an anti-CD73 antibody, an Fc region, and IL-2 or a variant thereof, and a polypeptide comprising the light chain variable region (VL) and light chain constant region (CL) of the anti-CD73 antibody, are linked to each other by a disulfide bond formed by cysteines.

Polynucleotide Encoding Fusion Protein

Another aspect of the present invention provides a polynucleotide encoding a fusion protein comprising: an antibody or an antigen-binding fragment thereof that specifically binds to CD73; and IL-2 or a variant thereof. The antibody or antigen-binding fragment thereof that specifically binds to CD73 is as described above, and the IL-2 or variant thereof is also as described above.

Specifically, the polynucleotide encoding the fusion protein comprising the single-domain antibody that specifically binds to CD73, the Fc region, and the IL-2 or variant thereof may comprise any one nucleotide sequence selected from the group consisting of SEQ ID NO: 31, SEQ ID NO: 33, and SEQ ID NO: 35.

In addition, the polypeptide comprising the heavy chain variable region (VH) and heavy chain constant region 1 (CH1) of the anti-CD73 antibody, the Fc region, and the IL-2 or variant thereof, and the polypeptide comprising the light chain variable region (VL) and light chain constant region (CL) of the anti-CD73 antibody may be encoded by the nucleotide sequence of SEQ ID NO: 37 and the nucleotide sequence of SEQ ID NO: 39, respectively.

In addition, if the polynucleotide encodes the same polypeptide, one or more nucleotides may be altered by substitution, deletion, insertion, or a combination thereof. When a polynucleotide sequence is produced by chemical synthesis, synthetic methods well known in the art may be used, such as those described in Engels and Uhlmann, Angew Chem Int Ed Eng., 37:73-127, 1988. Such methods include, for example, triester, phosphite, phosphoramidite and H-phosphate methods, PCR and other autoprimer methods, oligonucleotide syntheses on solid supports, and the like.

According to one embodiment, the polynucleotide may comprise a nucleotide sequence having an identity of at least about 70%, at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or at least about 100% to the nucleotide sequence of each of SEQ ID NO: 31, SEQ ID NO: 33, SEQ ID NO: 35, SEQ ID NO: 37, and SEQ ID NO: 39.

The polynucleotide may further comprise a signal sequence or a leader sequence. As used herein, the term "signal sequence" refers to a nucleic acid encoding a signal peptide that directs secretion of a target protein. The signal peptide is translated and then cleaved in a host cell. Specifically, the signal sequence of the present invention is a polynucleotide encoding an amino acid sequence that initiates migration of a protein across the endoplasmic reticulum (ER) membrane.

Signal sequences are well known in the art for their characteristics. Such signal sequences typically comprise 16 to 30 amino acid residues, but may comprise more or fewer amino acid residues than such amino acid residues. A typical signal peptide is composed of three regions, that is, a basic N-terminal region, a central hydrophobic region, and a more polar C-terminal region. The central hydrophobic region comprises 4 to 12 hydrophobic residues that cause the signal sequence to be immobilized during migration of an immature polypeptide through the membrane lipid bilayer.

After initiation, signal sequences are cleaved in the lumen of ER by cellular enzymes, commonly known as signal peptidases. Here, the signal sequence may be a secretory signal sequence of tPa (tissue plasminogen activator), HSV gDs (signal sequence of Herpes simplex virus glycoprotein D), an IgG signal sequence, or a growth hormone. Preferably, a secretory signal sequence used in higher eukaryotic cells including mammals and the like may be used. Signal sequences useful in the present invention include antibody light chain signal sequences, e.g., antibody 14.18 (Gillies et al., *J. Immunol. Meth.* 125:191-202 (1989)), antibody heavy chain signal sequences, e.g., the MOPC141 antibody heavy chain signal sequence (Sakano et al., *Nature* 286:676-683), and other signal sequences known in the art (see, e.g., Watson et al., *Nucleic Acid Research*, 1984. 12:5145-5164). In one embodiment, the signal sequence may comprise the amino acid sequence of SEQ ID NO: 1.

Vector Containing Polynucleotide

Another aspect of the present invention provides an expression vector containing a polynucleotide encoding a fusion protein comprising: an antibody or an antigen-binding fragment thereof that specifically binds to CD73; and IL-2 or a variant thereof. Here, the antibody or antigen-binding fragment thereof that specifically binds to CD73, the antigen-binding site, and the IL-2 and variant thereof are as described above.

Specifically, the polynucleotide encoding the fusion protein comprising the anti-CD73 single-domain antibody and the IL-2 or variant thereof may comprise any one nucleotide sequence selected from the group consisting of SEQ ID NO: 30, SEQ ID NO: 32, and SEQ ID NO: 34.

In addition, the polynucleotide encoding the fusion protein comprising the anti-CD73 antibody and the IL-2 or variant thereof may comprise the nucleotide sequence of SEQ ID NO: 37, which encodes the heavy chain region of the anti-CD73 antibody, and the nucleotide sequence of SEQ ID NO: 39, which encodes the light chain region of the anti-CD73 antibody. In addition, in one embodiment, when each of the nucleotide sequences contains a signal sequence, the sequence encoding the heavy chain region may be the nucleotide sequence of SEQ ID NO: 36, and the sequence encoding the light chain region may be the nucleotide sequence of SEQ ID NO: 38. In this case, the polynucleotide may be inserted into an expression vector, and as an example, it may be inserted into a bicistronic expression vector.

As used in the present specification, the term "vector" refers to a vector that may be introduced into a host cell and recombined and inserted into the genome of the host cell. Alternatively, the vector is understood as a nucleic acid vehicle containing a nucleotide sequence that is capable of self-replication as an episome. Examples of the vector include linear nucleic acids, plasmids, phagemids, cosmids, RNA vectors, viral vectors, mini-chromosomes, and analogs thereof. Examples of the viral vector include, but are not limited to, retroviruses, adenoviruses, and adeno-associated viruses.

Specifically, the vector may include plasmid DNA, phage DNA, or the like, and examples thereof include commercially developed plasmids (pUC18, pBAD, pIDTSAMRT-AMP, and the like), *E. coli*-derived plasmids (pYG601BR322, pBR325, pUC118, pUC119, and the like), *Bacillus subtilis*-derived plasmids (pUB110, pTP5, and the like), yeast-derived plasmids (YEp13, YEp24, YCp50, and the like), phage DNA (Charon4A, Charon21A, EMBL3, EMBL4, λ gt10, λ gt11, A ZAP, and the like), animal viral vectors (retroviruses, adenoviruses, vaccinia viruses, and the like), insect viral vectors (baculoviruses and the like). Since the vector exhibits different expression levels and modification of a protein depending on a host cell, it is preferred to select and use a host cell which is most suitable for the purpose.

In addition, the plasmid may contain a selection marker such as an antibiotic resistance gene, and host cells maintaining the plasmid may be cultured under selective conditions.

As used in the present specification, the term "gene expression" or "expression" of a target protein is understood to mean transcription of DNA sequences, translation of mRNA transcripts, and secretion of fusion protein products or fragments thereof. A useful expression vector may be RcCMV (Invitrogen, Carlsbad) or a variant thereof. The expression vector may contain a human cytomegalovirus (CMV) promoter for promoting continuous transcription of a target gene in mammalian cells, and a bovine growth hormone polyadenylation signal sequence for increasing the stability level of RNA after transcription.

Transformed Cell

Another aspect of the present invention provides a transformed cell into which an expression vector containing a polynucleotide encoding a fusion protein comprising: an antibody or an antigen-binding fragment thereof that specifically binds to CD73; and IL-2 or a variant thereof, has been introduced. Here, the expression vector containing the polynucleotide is as described above.

As used in the present specification, the term "transformed cell" refers to prokaryotic cells and eukaryotic cells into which a recombinant expression vector has been introduced. The transformed cell may be produced by transforming a host cell by introduction of the vector. In addition, the fusion protein of the present invention may be produced by expressing the polynucleotide contained in the vector.

The transformation may be performed by various methods. The transformation method is not particularly limited as long as it can produce the fusion protein of the present invention. Specifically, examples of the transformation method include CaCl$_2$) precipitation, Hanahan method whose efficiency has been increased by using a reducing agent such as dimethyl sulfoxide (DMSO) in CaCl$_2$) precipitation, electroporation, calcium phosphate precipitation, protoplast fusion, agitation using silicon carbide fiber, *Agrobacterium*-mediated transformation, transformation using PEG, dextran sulfate-, lipofectamine-, and desiccation/inhibition transformation, and the like. In addition, the target can be delivered into cells using virus particles by means of infection. In addition, the vector may be introduced into the host cell by gene bombardment or the like.

In addition, the host cell used to produce the transformed cell is also not particularly limited as long as it can produce the antibody of the present invention. Specifically, examples of the host cell include, but are not limited to, prokaryotic cells, eukaryotic cells, and cells of mammalian, plant, insect, fungal, or bacterial origin. As an example of the prokaryotic cells, *E. coli* may be used. In addition, as an example of the eukaryotic cells, yeast may be used. In addition, as the mammalian cells, CHO cells, F2N cells, COS cells, BHK cells, Bowes melanoma cells, HeLa cells, 911 cells, AT1080 cells, A549 cells, SP2/0 cells, human lymphoblastoids, NSO cells, HT-1080 cells, PERC.6 cells, HEK 293 cells, HEK293T cells, or the like may be used, without being limited thereto. In addition, any cells which are known to those skilled in the art to be usable as mammalian host cells may be used.

In addition, for optimization of properties of an antibody as a therapeutic agent or for any other purpose, glycosylation pattern of the antibody (for example, sialic acids, fucosylations, glycosylations) may be adjusted by manipulating, through methods known to those skilled in the art, glycosylation-related genes possessed by host cells.

Method for Producing Fusion Protein Dimer

Another aspect of the present invention provides a method for producing a fusion protein dimer comprising: an antibody or an antigen-binding fragment thereof that specifically binds to CD73; and IL-2 or a variant thereof. Here, the fusion protein and the fusion protein dimer are as described above.

Specifically, the method for producing the fusion protein dimer may comprise steps of: i) culturing the transformed cell; and ii) collecting the fusion protein dimer.

As used in the present specification, the term "culturing" refers to a method of growing microorganisms under appropriately artificially controlled environmental conditions.

Culturing the transformed cell may be carried out using methods well known in the art. Specifically, the culturing method is not particularly limited as long as it can express and produce the antibody of the present invention. Specifically, the culturing may be carried out in a batch process, or carried out continuously in a fed batch or repeated fed batch process.

In addition, the step of collecting the antibody from the culture may be performed by methods known in the art. Specifically, the collecting method is not particularly limited as long as the produced fusion protein of the present invention may be collected. Preferably, the collecting method may be a method such as centrifugation, filtration, extraction, spraying, drying, evaporation, precipitation, crystallization, electrophoresis, fractional dissolution (e.g., ammonium sulfate precipitation), chromatography (e.g., ion exchange, affinity, hydrophobicity, and size exclusion), or the like.

Use of Fusion Protein (Dimer)

Another aspect of the present invention provides a pharmaceutical composition for preventing or treating cancer containing, as an active ingredient, a fusion protein or fusion protein dimer comprising: an antibody or an antigen-binding fragment thereof that specifically binds to CD73; and IL-2 or a variant thereof. The fusion protein and the fusion protein dimer are as described above.

Specifically, the present invention provides a pharmaceutical composition for preventing or treating cancer containing, as an active ingredient, a fusion protein comprising an anti-CD73 single-domain antibody and IL-2 or a variant thereof, or a dimer of the fusion proteins.

The present invention also provides a pharmaceutical composition for preventing or treating cancer containing, as an active ingredient, a fusion protein comprising an anti-CD73 antibody and IL-2 or a variant thereof, or a dimer of the fusion proteins.

As used in the present specification, the term "cancer" is classified as a disease in which normal tissue cells proliferate indefinitely for some reason and continue to grow rapidly regardless of the living phenomenon of the living organism or the surrounding tissue condition. The cancer in the present invention may be, but is not limited to, any one cancer selected from the group consisting of various human cancers, for example, gastric cancer, liver cancer, lung cancer, colorectal cancer, breast cancer, prostate cancer, ovarian cancer, pancreatic cancer, cervical cancer, thyroid cancer, laryngeal cancer, acute myeloid leukemia, brain tumor, neuroblastoma, retinoblastoma, head and neck cancer, salivary gland cancer, and lymphoma.

Although a preferred dose of the pharmaceutical composition varies depending on the patient's condition and body weight, the disease's severity, the form of drug, and the route and duration of administration, it may be appropriately selected by those skilled in the art. In the pharmaceutical composition for treating or preventing cancer according to the present invention, the fusion protein may be contained in any amount (effective amount) depending on the application, dosage form, and blending purpose thereof, as long as the fusion protein can exhibit anticancer activity or, in particular, a therapeutic effect on cancer. A conventional effective amount of the fusion protein will be determined within a range of 0.001 wt % to 20.0 wt % based on the total weight of the composition. As used herein, the "effective amount" refers to an amount of an active ingredient that can induce the effect of alleviating or treating the condition of a disease, in particular the effect of alleviating or treating the condition of cancer. Such an effective amount can be experimentally determined within the scope of common knowledge of those skilled in the art.

As used herein, the term "treatment" may be used to mean both therapeutic treatment and prophylactic treatment, and covers any application or administration for treating a disease in a mammal, including a human. In addition, the term includes inhibiting or slowing progression of the disease; partially or fully relieving the disease by restoring or repairing a lost, missing, or defective function; stimulating an inefficient process; or alleviating a serious disease. The "prevention" may be used to mean alleviating or reducing the pathological condition or disease of an individual.

Pharmacokinetic parameters such as bioavailability and underlying parameters such as clearance rate may also impact efficacy. Thus, an "enhanced efficacy" (e.g., an improvement in efficacy) may be due to improved pharmacokinetic parameters as well as improved potency, and may be measured by comparing clearance rates in test animals or in human subjects, as well as parameters such as cancer disease treatment or alleviation.

Meanwhile, the pharmaceutical composition of the present invention is administered in a "therapeutically effective amount".

As used in the present specification, the term "administration" means introducing a given substance into a subject by any suitable method. The composition may be administered through any general routes as long as it can reach the target tissue. The composition may be administered intraperitoneally, intravenously, intramuscularly, subcutaneously, intradermally, orally, topically, intranasally, intrapulmonary, or intrarectally, without being limited thereto.

As used in the present specification, the term "therapeutically effective amount" or "pharmaceutically effective amount" refers to an amount of a compound or composition effective to prevent or treat the disease in question, which is sufficient to treat the disease at a reasonable benefit/risk ratio applicable to medical treatment and does not cause adverse effects. A level of the effective amount may be determined depending on factors including the patient's health condition, the type and severity of disease, the activity of drug, sensitivity to drug, the mode of administration, the time of administration, the route of administration, excretion rate, the duration of treatment, formulation or drugs used in combination with the composition, and other factors well known in the medical field. In one embodiment, the therapeutically effective amount means an amount of drug effective to treat cancer.

Here, the pharmaceutical composition may further contain a pharmaceutically acceptable carrier. The pharmaceutically acceptable carrier may be any carrier that is a non-toxic substance suitable for delivery to a patient. Distilled water, alcohol, fat, wax, and inert solid may be contained as the carrier. A pharmaceutically acceptable adjuvant (buffer, dispersant) may also be contained in the pharmaceutical composition.

Specifically, by containing a pharmaceutically acceptable carrier, the pharmaceutical composition may be prepared into a parenteral formulation depending on its route of administration using conventional methods known in the art. Here, the term "pharmaceutically acceptable" means that the carrier does not have more toxicity than the subject to whom/which the pharmaceutical composition is to be applied (prescribed) can adapt while not inhibiting activity of the active ingredient.

When the pharmaceutical composition is prepared into a parenteral formulation, it may be made into preparations in the form of injections, transdermal patches, nasal inhalants, or suppositories with suitable carriers according to methods known in the art. For formulation into injectable formulations, sterile water, ethanol, polyol such as glycerol or propylene glycol, or a mixture thereof may be used as a suitable carrier; and an isotonic solution, such as Ringer's solution, phosphate buffered saline (PBS) containing triethanol amine, sterile water for injection, or 5% dextrose may preferably be used. Formulation of pharmaceutical compositions is known in the art, and reference may specifically be made to Remington's Pharmaceutical Sciences (19$^{th}$ ed., 1995), and the like. This document is considered part of the present specification.

A preferred dose of the pharmaceutical composition may range from 0.0001 μg/kg to 100 g/kg per day, depending on the patient's condition, body weight, sex, age, severity of the patient, and route of administration. The dose may be administered once or several times a day. Such a dose should not be construed as limiting the scope of the present invention in any way.

Subjects to whom/which the pharmaceutical composition may be applied (prescribed) are mammals and humans, with humans being particularly preferred. The pharmaceutical composition of the present invention may further contain any compound or natural extract known to have a cancer therapeutic effect.

Another aspect of the present invention provides the use of a fusion protein or fusion protein dimer comprising: an antibody or an antigen-binding fragment thereof that specifically binds to CD73; and IL-2 or a variant thereof, for manufacture of a medicament for preventing or treating cancer.

Another aspect of the present invention provides a method for preventing or treating cancer, comprising a step of administering to a subject a fusion protein or fusion protein dimer comprising: an antibody or an antigen-binding fragment thereof that specifically binds to CD73; and IL-2 or a variant thereof. The subject may be a mammal, preferably a human. In addition, the subject may be a patient suffering from cancer, or a subject who is highly likely to suffer from cancer.

The route of administration, dose, and frequency of administration of the fusion protein may vary depending on the patient's condition and the presence or absence of side effects, and the fusion protein may be administered to the subject in various ways and amounts. The optimal administration method, dosage, and frequency of administration of the fusion protein may be selected within appropriate ranges by a person skilled in the art. A preferred dose of the fusion protein comprising: the antigen binding site that specifically binds to CD73; and IL-2 or a variant thereof, may range from 0.0001 μg/kg to 100 g/kg per day depending on the patient's condition, weight, sex, age, severity of the patient, and the route of administration. The dose may be administered once or several times a day. Such a dose should not be construed as limiting the scope of the present invention in any way.

MODE FOR INVENTION

Hereinafter, the present invention will be described in more detail by way of examples. These examples are only for illustrating the present invention in more detail, and it will be apparent to those skilled in the art that the scope of the present invention according to the subject matter of the present invention is not limited by these examples.

I. Production of Fusion Proteins and Dimers Thereof

Example 1. Production of GI-108A1: Anti-CD73 sdAb-hIgG4 Fc-hIL2v3

To produce a fusion protein comprising: an anti-CD73 single domain antibody (AHF10235, AHF10240, or AHP04167) that specifically binds to CD73; and an IL-2 variant, a polynucleotide (SEQ ID NO: 30, 32 or 34) encoding a signal peptide (SEQ ID NO: 1), an anti-CD73 single domain antibody (SEQ ID NO: 2, 3 or 4), linker (1) (SEQ ID NO: 5), an IgG4 Fc region (SEQ ID NO: 6), linker (2) (SEQ ID NO: 7), and an IL-2 variant (SEQ ID NO: 8) with three amino acid substitutions was cloned into a pCGS3 vector (Sigma-Aldrich®) using a Bioxp™ 3250 SYSTEM (Tables 1 to 3).

TABLE 1

| | Amino acid sequence | SEQ ID NO. |
|---|---|---|
| mIgG signal | MEWSWVFLFFLSVTTGVHS | 1 |
| Anti-hCD73 sdAb (AHF10235) | QVQVQESGGGLVQAGDSLRLSCAASGRSISRYNMGWFRQA PGKEREFVAAISRSGGVTYYADSVKGRLTISRDNAKSAVYL QMNSLKPEDTAVYYCAADWRNSDSPSPLIIVYDYWGQGTQ VTVSS | 2 |
| Linker (1) | GGGGS AESKYGPPCPPCP | 5 |
| hIgG4 Fc (F01) | APEAAGGPSVFLFPPKPKDQLMISRTPEVTCVVVDVSQEDPE VQFNWYVDGVEVHNAKTKPREEQFNSTYRVVSVLTVLHQD WLNGKEYKCKVSNKGLPSSIEKTISKAKGQPREPQVYTLPPS QEEMTKNQVSLTCLVKGFYPSDIAVEWESNGQPENNYKTTP PVLDSDGSFFLYSRLTVDKSRWQEGNVFSCSVLHEALHNHY TQKSLSLSLG | 6 |
| Linker (2) | GGGGSGGGGSGGGGS | 7 |
| hIL2v3 | APTSSSTKKTQLQLEHLLLDLQMILNGINNYKNPKLTAMLT AKFYMPKKATELKHLQCLERELKPLEEVLNLAQSKNFHLRP RDLISNINVIVLELKGSETTFMCEYADETATIVEFLNRWITFC QSIISTLT | 8 |

TABLE 2

| | Amino acid sequence | SEQ ID NO. |
|---|---|---|
| mIgG signal | MEWSWVFLFFLSVTTGVHS | 1 |
| Anti-hCD73 sdAb (AHF10240) | EVQLVESGGGVVQTGGSLRLSCAASGRTFTHLAMGWFRQ APGKEREFVAAISNSGAGTQFADSVKGRFTISRDNAKNTVY LQMNSLKPEDTAVYYCAADWGTRDSPSKLNAVYDYWGR GTQVTVSS | 3 |
| Linker (1) | GGGGS AESKYGPPCPPCP | 5 |
| hIgG4 Fc (F01) | APEAAGGPSVFLFPPKPKDQLMISRTPEVTCVVVDVSQEDP EVQFNWYVDGVEVHNAKTKPREEQFNSTYRVVSVLTVLH QDWLNGKEYKCKVSNKGLPSSIEKTISKAKGQPREPQVYTL PPSQEEMTKNQVSLTCLVKGFYPSDIAVEWESNGQPENNY KTTPPVLDSDGSFFLYSRLTVDKSRWQEGNVFSCSVLHEAL HNHYTQKSLSLSLG | 6 |
| Linker (2) | GGGGSGGGGSGGGGS | 7 |
| hIL2v3 | APTSSSTKKTQLQLEHLLLDLQMILNGINNYKNPKLTAMLT AKFYMPKKATELKHLQCLERELKPLEEVLNLAQSKNFHLR PRDLISNINVIVLELKGSETTFMCEYADETATIVEFLNRWITF CQSIISTLT | 8 |

TABLE 3

| | Amino acid sequence | SEQ ID NO. |
|---|---|---|
| mIgG signal | MEWSWVFLFFLSVTTGVHS | 1 |
| Anti-hCD73 sdAb (AHP04167) | EVQLVESGGGLVQAGGSLRLSCVVSGRTFSNYHMGWFRQ APGKEREFVAVIGRSGGPTYYADSVKGRFTISRDNAKNTV YLQMNSLKPEDTAVYYCAGDWRNSDSPSKLKPVYDYWG QGTQVTVSS | 4 |
| Linker (1) | GGGGS AESKYGPPCPPCP | 5 |
| hIgG4 Fc (F01) | APEAAGGPSVFLFPPKPKDQLMISRTPEVTCVVVDVSQEDP EVQFNWYVDGVEVHNAKTKPREEQFNSTYRVVSVLTVLH QDWLNGKEYKCKVSNKGLPSSIEKTISKAKGQPREPQVYT LPPSQEEMTKNQVSLTCLVKGFYPSDIAVEWESNGQPENN YKTTPPVLDSDGSFFLYSRLTVDKSRWQEGNVFSCSVLHEA LHNHYTQKSLSLSLG | 6 |
| Linker (2) | GGGGSGGGGSGGGGS | 7 |
| hIL2v3 | APTSSSTKKTQLQLEHLLLDLQMILNGINNYKNPKLTAMLT AKFYMPKKATELKHLQCLERELKPLEEVLNLAQSKNFHLR PRDLISNINVIVLELKGSETTFMCEYADETATIVEFLNRWITF CQSIISTLT | 8 |

In addition, each of the vectors was introduced into CHO cells (Expi-CHO™, Thermo Fisher Scientific) to express the fusion proteins. After introducing the vectors, the cells were cultured under the conditions of 37° C., 125 rpm, and 8% $CO_2$. Thereafter, the cultures were harvested and the fusion protein dimers were purified therefrom. The three purified fusion protein dimers were named "GI-108A1 (AHF10235)", "GI-108A1 (AHF10240)", and "GI-108A1 (AHP04167)", respectively. Specifically, each of the three fusion protein dimers was purified using chromatography with Protein A resin. After filtering the harvested cultures, each of the filtered cultures was loaded onto a column and flowed through the column. Next, the fusion protein dimers were collected using 50 mM glycine (pH 3.4).

A buffer containing each of the three collected fusion protein dimers (GI-108A1 (AHF10235), GI-108A1 (AHF10240), and GI-108A1 (AHP04167)) was exchanged with PBS (phosphate buffered saline, pH 7.4) through dialysis. Using a NanoDrop system (Thermo Fisher Scientific), it was identified that the fusion protein dimers were contained at concentrations of 3.86 mg/mL, 4.12 mg/mL, and 12.86 mg/mL, respectively. In addition, as a result of analyzing the purities through size exclusion chromatography (SEC) analysis, the purities of the three purified fusion protein dimers were 71.81%, 75.36%, and 93.87%, respectively (Table 4 and Table 5).

TABLE 4

| | Peak Name | RT | Area | % Area | Height |
|---|---|---|---|---|---|
| GI-108A1 (AHF10235) | | | | | |
| 1 | Peak 1 | 12.067 | 24947 | 0.90 | 762 |
| 2 | Peak 2 | 14.015 | 124244 | 4.50 | 2122 |
| 3 | Peak 3 | 14.980 | 377981 | 13.68 | 6230 |
| 4 | Monomer | 17.022 | 1983970 | 71.81 | 48598 |
| GI-108A1 (AHF10240) | | | | | |
| 1 | Peak 1 | 11.962 | 198392 | 6.85 | 7601 |
| 2 | Peak 2 | 13.697 | 138199 | 4.77 | 2536 |
| 3 | Peak 3 | 14.694 | 351133 | 12.12 | 6847 |
| 4 | Monomer | 16.739 | 2183777 | 75.36 | 60301 |
| GI-108A1 (AHP04167) | | | | | |
| 1 | Peak 1 | 12.111 | 21365 | 0.41 | 331 |
| 2 | Peak 2 | 14.769 | 295396 | 5.72 | 5156 |
| 3 | Monomer | 16.682 | 4849570 | 93.87 | 140556 |

TABLE 5

| ID | Concentration after formulation (mg/mL) | Final protein (mg) | Purification yield* (μg/mL) | Final purity | Aggregation |
|---|---|---|---|---|---|
| GI-108A1 (AHF10235) | 3.86 | 14.66 | 146.57 | 71.81 | X |
| GI-108A1 (AHF10240) | 4.12 | 38.76 | 387.56 | 75.36 | X |
| GI-108A1 (AHP04167) | 12.86 | 41.14 | 411.39 | 93.87 | X |

*Purification Yield: Purification μg/culture mL, 100 mL Scale

Example 2. Production of GI-108B1: Anti-CD73 Ab-hIgG4 Fc-hIL2v3

To produce a fusion protein dimer comprising: an anti-CD73 antibody that specifically binds to CD73; and an IL-2 variant, a polynucleotide (SEQ ID NO: 36) encoding a signal peptide (SEQ ID NO: 1), an anti-CD73 antibody heavy-chain variable region (SEQ ID NO: 9) and constant region (SEQ ID NO: 10), linker (1) (SEQ ID NO: 11), an IgG4 Fc region (SEQ ID NO: 6), linker (2) (SEQ ID NO: 12), and an IL-2 variant (SEQ ID NO: 8) with three amino acid substitutions, and a polynucleotide (SEQ ID NO: 38) encoding a signal peptide (SEQ ID NO: 1) and an anti-CD73 antibody light-chain variable region (SEQ ID NO: 13) and constant region (SEQ ID NO: 14) were cloned into a pCGS3 vector (SIGMA-ALDRICH®) using a BIOXP™ 3250 SYSTEM (Table 6).

In addition, the vector was introduced into CHO cells (EXPI-CHO™, Thermo Fisher Scientific) to express the fusion protein dimer. After introducing the vector, the cells were cultured under the conditions of 37° C., 125 rpm, and 8% $CO_2$. Thereafter, the culture was harvested and the fusion protein dimer was purified therefrom. The purified fusion protein dimer was named "GI-108B1".

TABLE 6

| | | Amino acid sequence | SEQ ID NO. |
|---|---|---|---|
| Anti-hCD73 HC-hIgG4Fc-hIL2v3 | mIgG signal | MEWSWVFLFFLSVTTGVHS | 1 |
| | Anti-hCD73 VH (CSA0060) | QVQLVQSGAEVKKPGSSVKVSCKFSGGSFTSY SFSWVRQAPGQGLEWMGRIIPVLTTTDYAQKF RDRVTITADESTSTAYMELSGLRSEDTAVYYC ASGLKKNWYFDLWGRGALITVSS | 9 |
| | Anti-hCD73 CH1 (CSA0060) | ASTKGPSVFPLAPCSRSTSESTAALGCLVKDYF PEPVTVSWNSGALTSGVHTFPAVLQSSGLYSLS SVVTVPSSSLGTKTYTCNVDHKPSNTKVDKRV | 10 |
| | Linker (1) | ESKYGPPCPPCP | 11 |
| | hIgG4 Fc (F01) | APEAAGGPSVFLFPPKPKDQLMISRTPEVTCVV VDVSQEDPEVQFNWYVDGVEVHNAKTKPREE QFNSTYRVVSVLTVLHQDWLNGKEYKCKVSN KGLPSSIEKTISKAKGQPREPQVYTLPPSQEEMT KNQVSLTCLVKGFYPSDIAVEWESNGQPENNY KTTPPVLDSDGSFFLYSRLTVDKSRWQEGNVFS CSVLHEALHNHYTQKSLSLSLG | 6 |
| | Linker (2) | GGGGSGGGGS | 12 |
| | hIL2v3 | APTSSSTKKTQLQLEHLLLDLQMILNGINNYKN PKLTAMLTAKFYMPKKATELKHLQCLERELKP LEEVLNLAQSKNFHLRPRDLISNINVIVLELKGS ETTFMCEYADETATIVEFLNRWITFCQSIISTLT | 8 |
| Anti-hCD73 LC (kappa) | mIgG signal | MEWSWVFLFFLSVTTGVHS | 1 |
| | Anti-hCD73 VL (CSA0060) | DIQMTQSPSFLSASVGDRVTITCQASQDISHYLN WYQQKPGKAPKLLIYDASSLETGVPSRFSGSGS GTSFTLTISSLQPEDFATYYCQQYDDFPLTFGG GTKVDIK | 13 |
| | Anti-hCD73 kappa CL (CSA0060) | RSVAAPSVFIFPPSDEQLKSGTASVVCLLNNFYP REAKVQWKVDNALQSGNSQESVTEQDSKDST YSLSSTLTLSKADYEKHKVYACEVTHQGLSSP VTKSFNRGEC | 14 |
| | Anti-hCD73 VL-LCDR2 (CSA0060) | DAS | 28 |

Specifically, the GI-108B1 was purified using chromatography with Protein A resin. After filtering the harvested culture, the filtered culture was loaded onto a column and flowed through the column. Next, the fusion protein dimer was collected using 50 mM glycine (pH 3.4).

A buffer containing the collected fusion protein dimer was exchanged with PBS (pH 7.4) through dialysis. Using a NanoDrop system (Thermo Fisher Scientific), it was identified that the fusion protein dimer was contained at a concentration of 4.55 mg/mL. In addition, as a result of analyzing the purity through size exclusion chromatography (SEC) analysis, it was confirmed that the purity of the purified fusion protein dimer was and 83.63% (Table 7 and Table 8).

TABLE 7

| GI-108B1 | Peak Name | RT | Area | % Area | Height |
|---|---|---|---|---|---|
| 1 | Peak 1 | 11.969 | 340915 | 11.45 | 6998 |
| 2 | Peak 2 | 13.806 | 121831 | 4.09 | 1863 |
| 3 | Monomer | 15.656 | 2489084 | 83.63 | 57175 |
| 4 | Peak 3 | 17.726 | 24509 | 0.82 | 547 |

TABLE 8

| ID | Concentration after formulation (mg/mL) | Final protein (mg) | Purification yield* (μg/mL) | Final purity | Aggregation |
|---|---|---|---|---|---|
| GI-108B1 | 4.55 | 27.28 | 272.82 | 83.63 | X |

*Purification Yield: Purification μg/culture mL, 100 mL Scale

Example 3. Production of Anti-CD73 Antibody: GI-αCD73

To produce an anti-CD73 antibody, a polynucleotide (SEQ ID NO: 42) encoding a signal peptide (SEQ ID NO: 1), an anti-CD73 antibody heavy chain variable region (SEQ ID NO: 9) and constant region (SEQ ID NO: 10), linker (1) (SEQ ID NO: 11), and an IgG4 Fc region (SEQ ID NO: 6), and a polynucleotide (SEQ ID NO: 38) encoding a signal peptide (SEQ ID NO: 1), and an anti-CD73 antibody light chain variable region (SEQ ID NO: 13) and constant region (SEQ ID NO: 14) were cloned into a pCGS3 vector (SIGMA-ALDRICH®) using a BIOXP™ 3250 SYSTEM.

In addition, the vector was introduced into CHO cells (EXPI-CHO™, Thermo Fisher Scientific) to express the control antibody anti-CD73 antibody. After introducing the vector, the cells were cultured under conditions of 37° C., 125 rpm, and 8% $CO_2$. The culture was harvested and the control anti-CD73 antibody was purified therefrom. Purification was performed in the same manner as in Example 1.

Example 4. Production of IgG4 Fc-IL-2v

A polynucleotide (SEQ ID NO: 43) encoding a signal peptide (SEQ ID NO: 1), linker (1) (SEQ ID NO: 11), an IgG4 Fc region (SEQ ID NO: 6), linker (2) (SEQ ID NO: 12), and an IL-2 variant (SEQ ID NO: 8) with three amino acid substitutions was cloned into a pCGS3 vector (SIGMA-ALDRICH®) using a BIOXP™ 3250 SYSTEM.

In addition, the vector was introduced into CHO cells (EXPI-CHO™, Thermo Fisher Scientific) to express the fusion protein. After introducing the vector, the cells were cultured for 7 days under conditions of 37° C., 125 rpm, 5%

$CO_2$, and 80% humidity. The culture was then harvested and the IgG4 Fc-IL-2v fusion protein was purified therefrom.

II. Characterization of Fusion Protein Dimers

Example 5. Measurement of Binding Affinity of Each Fragment of GI-108 to Target Protein To quantitatively analyze the binding affinities to CD73 and IL-2 receptors of GI-108A1 (AHF04167), GI-108A1 (AHP10240) and GI-108B1, in which the anti-CD73 antibody that specifically binds to CD73 was linked to the IL-2 variant, and Aldesleukin (trade name: PROLEUKIN®, Novartis), the binding affinities were measured using SPR (surface plasmon resonance). Using a BIACORE™ T200 instrument (Cytiva), the binding affinities of GI-108A1 (AHF10240), GI-108A1 (AHP04167) and GI-108B1 to hCD73, cyCD73, mCD73, hIL-2Rα, hIL-2Rβ, and hIL-2Rβγ were analyzed. Oleclumab (Astrazeneca), produced on order from Ybiologics, Inc., was used as a control.

Specifically, to analyze the binding affinities to hCD73, cyCD73, and mCD73, each of GI-108A1 (AHF10240), GI-108A1 (AHP04167), GI-108B1, and Oleclumab was diluted in HBS-EP+ buffer (Cytiva, USA) and reversibly immobilized on Sensor Chip CM5 (Cytiva, USA) using a human antibody capture kit (Cytiva, USA). CD73 was diluted in HBS-EP+ buffer and then analyzed for association and dissociation at a flow rate of 30 μL/min for 5 minutes each.

To analyze the binding affinity to hIL-2Rα, hIL-2Ra was irreversibly immobilized on Sensor Chip CM5 using a His capture kit (Cytiva, USA). Each of GI-108A1 (AHF10240), GI-108A1 (AHP04167), GI-108B1 and PROLEUKIN®, diluted in HBS-EP+ buffer, was then applied for 1 minute, followed by analysis of association and dissociation. In addition, the binding affinities to hIL-2RB and hIL-2Rβγ were measured by a three-step analysis method including treating Sensor Chip SA (Cytiva, USA) with biotinylated CD73, and then binding each of GI-108A1 (AHF10240), GI-108A1 (AHP04167), GI-108B1 and PROLEUKIN® to CD73, followed by treatment with each of hIL-2RB and hIL-2Rβγ diluted in HBS-P+ buffer (Cytiva, USA). For hIL-2Rβ, association was performed for 1 minute and dissociation for 1 minute, and for hIL-2Rβγ, association was performed for 5 minutes and dissociation for 2 hours at each concentration, in a single cycle kinetics analysis. Each sensorgram was normalized and subtracted compared to a blank cell to calculate affinity.

Table 9 below shows the results of measuring the binding affinities of GI-108A1 (AHF10240), GI-108A1 (AHP04167) and GI-108B1 to CD73 and IL-2 receptors using the BIACORE™ T200 instrument (Cytiva).

ment was conducted using HEK-BLUE™ IL-2 reporter cells (InvivoGen Inc.) expressing IL-2Rβγ. HEK-BLUE™ IL-2 reporter cells are induced to produce the reporter protein SEAP (secreted embryonic alkaline phosphatase) protein when the JAK-STAT pathway is activated by IL-2. In this experiment, the JAK-STAT pathway activation by IL-2 was evaluated by detecting the SEAP protein.

HEK-Blue™ IL-2 reporter cells were cultured in a DMEM medium (GIBCO™) containing 10% FBS (GIBCO™), 100 U/mL penicillin (Welgene Inc.), 100 μg/mL streptomycin (Welgene Inc.), and 100 μg/mL NORMOCIN™ (cat. ant-nr-1, InvivoGen Inc.). The HEK-BLUE™ IL-2 reporter cells were stabilized by subculture, and then harvested using trypsin (GIBCO™). Next, dead cells were removed by washing with PBS. The separated cells were suspended in a culture medium at about $2.8 \times 10^5$ cells/mL.

GI-108A1 (AHF10240), GI-108A1 (AHP04167), GI-108B1, and PROLEUKIN® as a control group were each diluted with PBS and dispensed into a 96-well plate (cat. 30096, SPL) at 20 μL per well. 180 μL of the prepared cell suspension was added to each well of the treated 96-well plate at a density of about $3 \times 10^4$ cells/well, and the cells were cultured in an incubator at 37° C. under 5% $CO_2$ for 24 hours.

After 24 hours, the 96-well plate was taken out of the incubator and centrifuged at 300×g for 5 minutes. Then, 20 μL of the supernatant was transferred to each well of a fresh 96-well plate. 180 μL of QUANTI-BLUE™ solution (cat. Rep-qbs, InvivoGen Inc.) dissolved at room temperature was dispensed into each well containing the supernatant. Each well was then incubated in an incubator for 30 minutes at 37° C. under 5% $CO_2$. After incubation, the absorbance was measured at a wavelength of 630 nm using a spectrophotometer (VERSAMAX™ Absorbance Microplate Reader). Data were analyzed using Graphpad prism 8.0 software.

Figure 3:
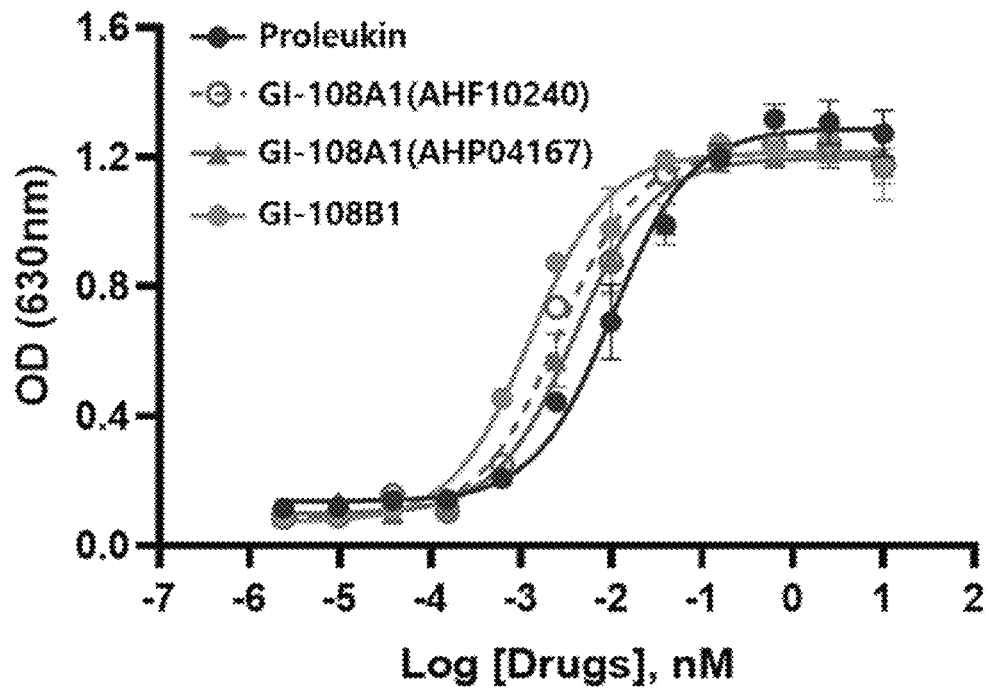
FIG. 3 is a graph showing the results of measuring the activity of the JAK-STAT signaling pathway after treating HEK-BLUE™ IL-2 reporter cells with two types of GI-108A1, GI-108B1, and PROLEUKIN®.

As a result, the absorbance was increased by each of GI-108A1 (AHF10240), GI-108A1 (AHP04167), GI-108B1, and PROLEUKIN® in a concentration-dependent manner. Thereby, it was confirmed that the JAK-STAT signaling pathway was activated by the IL-2 variant region of both types of GI-108A1 and GI-108B1 (FIG. 3). The $EC_{50}$ values of GI-108A1 (AHF10240) and GI-108A1 (AHP04167) were 2.63 pM and 3.94 pM, respectively, and the $EC_{50}$ value of GI-108B1 was 1.28 pM. The $EC_{50}$ value of the positive control PROLEUKIN® was 10.3 pM.

Example 7. Evaluation of Cell Proliferation Induced by IL-2 Variant of GI-108

The biological activity of the IL-2 variant of each of GI-108A1 and GI-108B was evaluated through a proliferation experiment using CTLL-2 cells expressing hIL-2Rαβγ.

TABLE 9

| $K_D$ (M) | hCD73 | cyCD73 | mCD73 | hIL-2Rα | hIL-2Rβ | hIL-2Rβγ |
|---|---|---|---|---|---|---|
| GI108B1 | 8.941E−11 | 1.13E−10 | N.B. | N.B. | 2.29E−06 | 2.00E−10 |
| GI108 A1 (AHF10240) | 5.02E−11 | 8.41E−11 | 2.62E−09 | N.B. | 2.50E−06 | 4.17E−10 |
| GI108 A1 AHP04167) | 8.80E−11 | 7.08E−11 | 3.45E−09 | N.B. | 2.07E−06 | 3.27E−10 |
| Oleclumab | 1.01E−10 | 3.49E−10 | N/A | N/A | N/A | N/A |
| PROLEUKIN ® | N/A | N/A | N/A | 4.96E−08 | 2.08E−06 | 1.00E−11 |

N.B.: not binding, N/A: not applicable

Example 6. Evaluation of the Ability of IL-2 Variant of GI-108 to Induce JAK-STAT Pathway Activation This experiment was conducted to evaluate the activity of the IL-2 variant region of GI-108. Specifically, the experi- CTLL-2 cells were cultured in complete RPMI 1640 medium (Thermo Fisher Scientific) supplemented with 0.2 mM L-glutamine, T-STIM™ culture supplement with ConA (concanavalin-A), 0.2 mM sodium pyruvate, and 10% FBS.

GI-108A1 (AHF10240), GI-108A1 (AHP04167), GI-108B1, and the control group PROLEUKIN® were each diluted with PBS and dispensed in a 96-well plate (cat. 30096, SPL) at 50 µL per well. The prepared CTLL-2 cells were added to each well of the drug-treated 96-well plate at a density of $1.2 \times 10^5$ cells per well. To analyze cell proliferation, 10 µL of WST-1 was added to each well which was then incubated at 37° C. for 4 hours, followed by measurement of the absorbance.

The absorbances were measured at wavelengths of 450 nm and 690 nm (reference) using a spectrophotometer (VERSAMAX™ Absorbance Microplate Reader). CTLL-2 cell proliferation data were analyzed by subtracting the absorbance value at 690 nm from the absorbance value at 450 nm.

Figure 4:
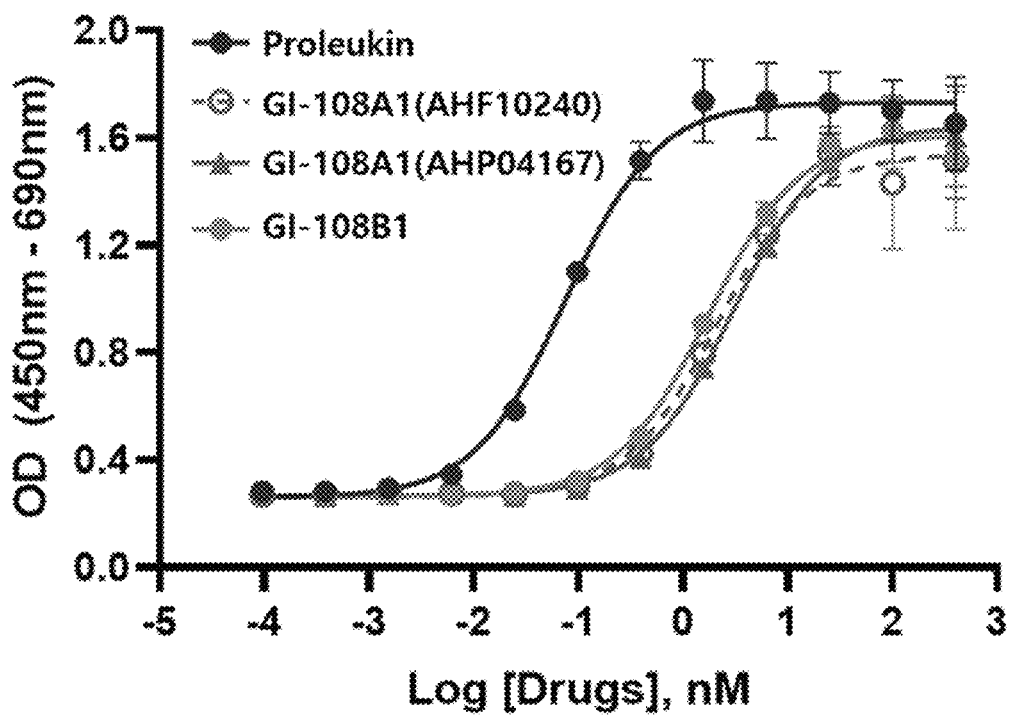
FIG. 4 is a graph showing the results of evaluating the degree of proliferation of CTLL-2 cells after treating the cells with two types of GI-108A1, GI-108B1, and PROLEUKIN®.

As a result, the absorbance was increased by each of GI-108A1 (AHF10240), GI-108A1 (AHP04167), GI-108B1, and PROLEUKIN® in a concentration-dependent manner. Thereby, it was confirmed that the proliferation of CTLL-2 cells was induced by the IL-2 variant region of both types of GI-108A1 and GI-108B1 (FIG. 4). The $EC_{50}$ values of GI-108A1 (AHF10240) and GI-108A1 (AHP04167) were 2.02 nM and 3.93 nM, respectively, and the $EC_{50}$ value of GI-108B1 was 1.70 nM. The $EC_{50}$ value of the positive control PROLEUKIN® was 0.08 nM.

The reason why the $EC_{50}$ value of PROLEUKIN® was lower than those of GI-108A1 and GI-108B1 was that the CTLL-2 cells expressed hIL-2Rαβγ. It was confirmed that as each of GI-108A1 and GI-108B1 do not bind to IL-2Rα, the $EC_{50}$ value thereof was at least 20 times higher than that of PROLEUKIN®.

Example 8. Evaluation of the Inhibitory Ability of GI-108 to Inhibit Membrane-Bound CD73 Enzyme Activity $1 \times 10^4$ MDA-MB-231 cells (human breast cancer cells) were dispensed into each well of 96-well plates, and each of GI-108A1 (AHF10240), GI-108A1 (AHP04167), GI-108B1 and the control Oleclumab was diluted from 300 µg/mL to a final concentration of 0.002 µg/mL and added to the 96-well plates at 50 µL per each well. Next, 100 µL of 200 µM AMP (SIGMA-ALDRICH®) was added to each well which was then incubated at 37° C. for 6 hours.

The 96-well plates were centrifuged, and the supernatants were transferred to new 96-well plates. Thereafter, the adenosine concentration of each of the supernatants was measured using an Adenosine Assay kit (Cell Biolabs, Inc) according to the manufacturer's protocol. $IC_{50}$ values were calculated using GraphPad Prism software.

Figure 5:
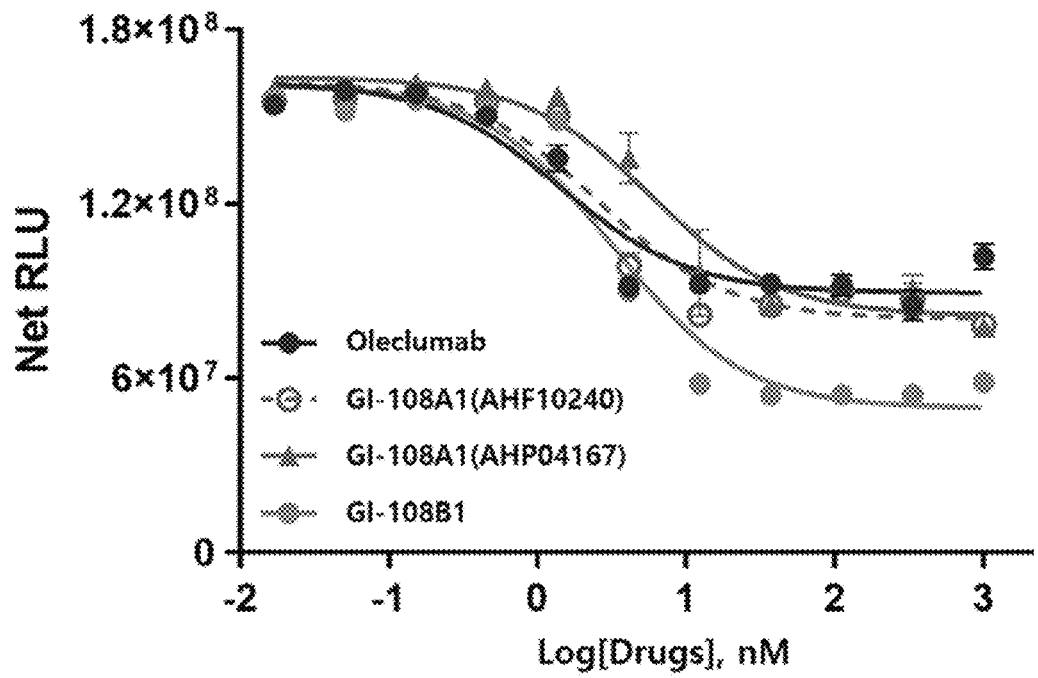
FIG. 5 is a graph showing the results of evaluating the ability of two types of GI-108A1, GI-108B1, and oleclumab to inhibit the enzymatic activity of membrane-bound human CD73 in human TNBC cell line (MDA-MB-231).

As a result, the degree of luminescence was reduced by each of GI-108A1 (AHF10240), GI-108A1 (AHP04167), GI-108B1, and Oleclumab in a concentration-dependent manner. Thereby, it was confirmed that both types of GI-108A1 and GI-108B1 inhibited membrane-bound CD73 enzyme activity (FIG. 5). The $IC_{50}$ values of GI-108A1 (AHF10240) and GI-108A1 (AHP04167) were 2.75 nM and 5.58 nM, respectively, and the $IC_{50}$ value of GI-108B1 was 3.37 nM. The $IC_{50}$ value of the control Oleclumab was 1.47 nM. Although the $IC_{50}$ value of GI-108B1 was higher than those of GI-108A1 (AHF10240) and Oleclumab, GI-108B1 showed the highest potential in enzyme inhibition efficacy.

Example 9. Evaluation of the Ability of GI-108 to Inhibit Soluble CD73 Enzyme Activity To evaluate the ability of GI-108 to inhibit soluble CD73 enzyme activity, an experiment was conducted using the AMP-Glo™ assay kit (Promega, V5012) according to the manufacturer's manual. Specifically, each of GI-108A1 (AHF10240), GI-108A1 (AHP04167), GI-108B1 and the control Oleclumab was diluted to 0.05 ng/ml and added to each well of 96-well plates at 2.5 µL per well, and 12.5 µL of 10 µM AMP was added to each well. Next, 2.5 ng/ml of recombinant human CD73 protein was added at 10 µL per well, followed by incubation at room temperature for 10 minutes.

The reaction was terminated by treating each well with 25 µL of AMP-Glo™ Reagent (Promega), and each well was shaken for 2 minutes and then incubated at room temperature for 1 hour. Each well was treated with AMP detection solution, shaken for 2 minutes, and then incubated at room temperature for 1 hour. The degree of luminescence was measured using the GLOMAX®-Multi Detection System (Promega), and $IC_{50}$ values were calculated using GraphPad Prism 8.0 software.

Figure 6:
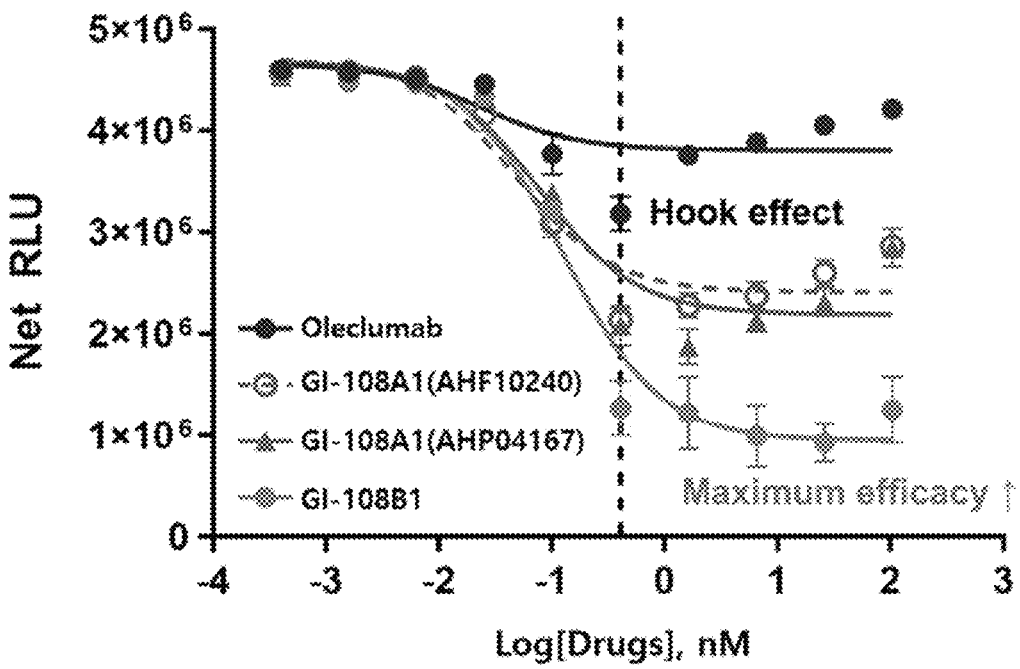
FIG. 6 is a graph showing the results of evaluating the ability of two types of GI-108A1, GI-108B1, and oleclumab to inhibit the enzymatic activity of soluble CD73.

As a result, the degree of luminescence was reduced by each of GI-108A1 (AHF10240), GI-108A1 (AHP04167), and GI-108B1 in a concentration-dependent manner. Thereby, it was confirmed that both types of GI-108A1 and GI-108B1 inhibited soluble CD73 enzyme activity (FIG. 6). Meanwhile, a hook effect appeared, indicating that the higher the treatment concentration of Oleclumab, the lower the enzyme inhibition efficacy. The $IC_{50}$ values of GI-108A1 (AHF10240) and GI-108A1 (AHP04167) were 0.060 nM and 0.102 nM, respectively, and the $IC_{50}$ values of GI-108B1 and Oleclumab were 0.126 nM and 0.03 nM, respectively. Although the $IC_{50}$ value of GI-108B1 was higher than those of both types of GI-108A1 and Oleclumab, GI-108B1 showed the highest potential in enzyme inhibition efficacy.

Example 10. Evaluation of Reinvitoration of T Cells Inhibited by CD73-Adenosine with GI-108B1

To evaluate whether GI-108B1 reinvigorates CD8+ T cell activity suppressed by CD73-adenosine, human PBMCs were cultured in TEXMACS™ medium (Miltenyi Biotec) containing 5% human serum (SIGMA-ALDRICH®), 1% penicillin/streptomycin and 5 mM β-mercaptoethanol (Thermo Fisher Scientific) under humidified conditions of 37° C. and 5% $CO_2$ overnight. The next day, the cells were labeled with CTV and seeded in each well of 96-well plates at $1 \times 10^6$ cells/ml. The cells were stimulated using αCD3/CD28 dynabeads (1:1 ratio).

The cells were treated with vehicle (hIgG4), PROLEUKIN®, GI-108B1, anti-CD73 antibody (GI-αCD73), IgG4 Fc-IL-2v and Oleclumab alone, a combination of anti-CD73 antibody (GI-αCD73) and IgG4 Fc-IL-2v, or a combination of Oleclumab and IgG4 Fc-IL-2v. Each of the drugs was added to each well to a final concentration of 50 nM. Then, 500 µM of AMP was added to each well, and the cells were cultured for 3 days under humidified conditions of 37° C. and 5% $CO_2$.

To evaluate the functional activation of T cells, the cells were re-stimulated with αCD3/CD28 dynabeads (1:1 ratio) and 50 nM or 500 µM AMP in the presence of Brefeldin A under humidified conditions of 37° C. and 5% $CO_2$ for 4 hours. For FACS analysis of Teff cell proliferation, surface markers of the cells were stained using the following antibodies: anti-CD3-PerCP-Cy5.5 (Clone: UCHT1, BD Biosciences), anti-CD8-Alexa Fluor700 (Clone: RPA-T8, Biolegend Inc.), and Fixable Viability Dye eFluor 780 (Invitrogen Inc.). To stain intracellular IFN-γ, the cells were treated with fixation/permeabilization buffer and then stained with anti-IFNγ-APC antibody (Clone: 4S.B3, Biolegend Inc.). Data on the stained cells were obtained using a Symphony A3 instrument and analyzed using FlowJo software.

Figure 7:
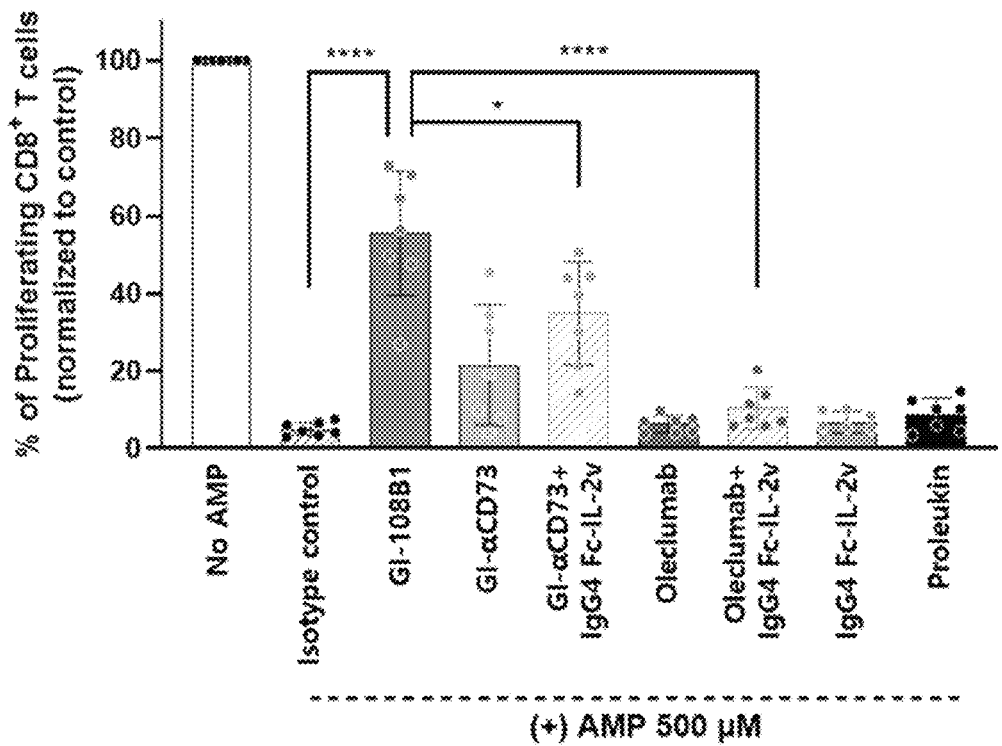
FIG. 7 is a graph showing the proliferation of CD8+ T cells after treating CD8+ T cells, the activity of which was inhibited by CD73-adenosine, with vehicle (hIgG4), GI-108B1 alone, PROLEUKIN® alone, IgG4 Fc-IL-2v alone, anti-CD73 antibody (GI-aCD73) alone, a combination of anti-CD73 antibody (GI-aCD73) and IgG4 Fc-IL-2v, oleclumab alone, or a combination of oleclumab and IgG4 Fc-IL-2v.
Figure 8:
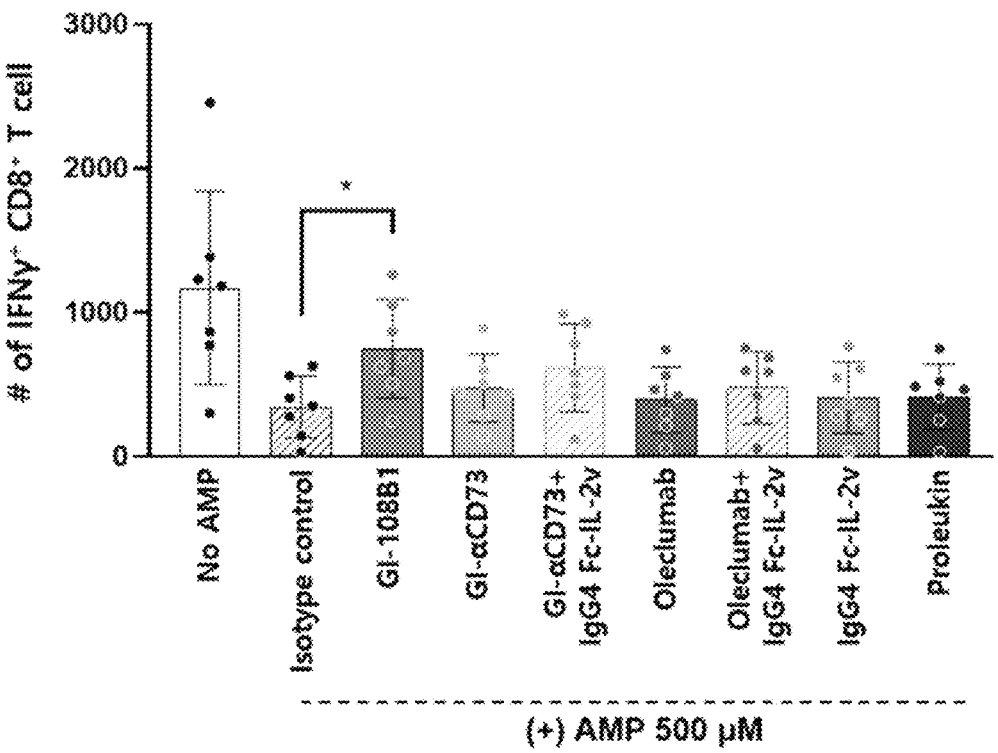
FIG. 8 is a graph showing the number of IFN-γ+CD8+ T cells after treating CD8+ T cells, the activity of which was inhibited by CD73-adenosine, with vehicle (hIgG4), GI-108B1 alone, PROLEUKIN® alone, IgG4 Fc-IL-2v alone, anti-CD73 antibody (GI-aCD73) alone, a combination of anti-CD73 antibody (GI-aCD73) and IgG4 Fc-IL-2v, oleclumab alone, or a combination of oleclumab and IgG4 Fc-IL-2v.

As a result, when treated with AMP and vehicle (hIgG4), the proliferation of CD8+ T cells was reduced. On the other hand, when treated with GI-108B1, the proliferation of CD8+ T cells significantly increased. In addition, it was confirmed that the proliferation of CD8+ T cells increased even when treated with anti-CD73 antibody alone or with a combination of anti-CD73 antibody and IgG4 Fc-IL-2v. Meanwhile, when treated with PROLEUKIN®, Oleclumab or IgG4 Fc-IL-2v alone or when treated with a combination of Oleclumab and IgG4 Fc-IL-2v, the proliferation of CD8+ T cells did not tend to increase (FIG. 7). In addition, when treated with AMP and vehicle (hIgG4), the production of IFN-γ by CD8+ T cells was reduced. On the other hand, when treated with GI-108B1, the production of IFN-γ by CD8+ T cells significantly increased (FIG. 8).

Figure 9:
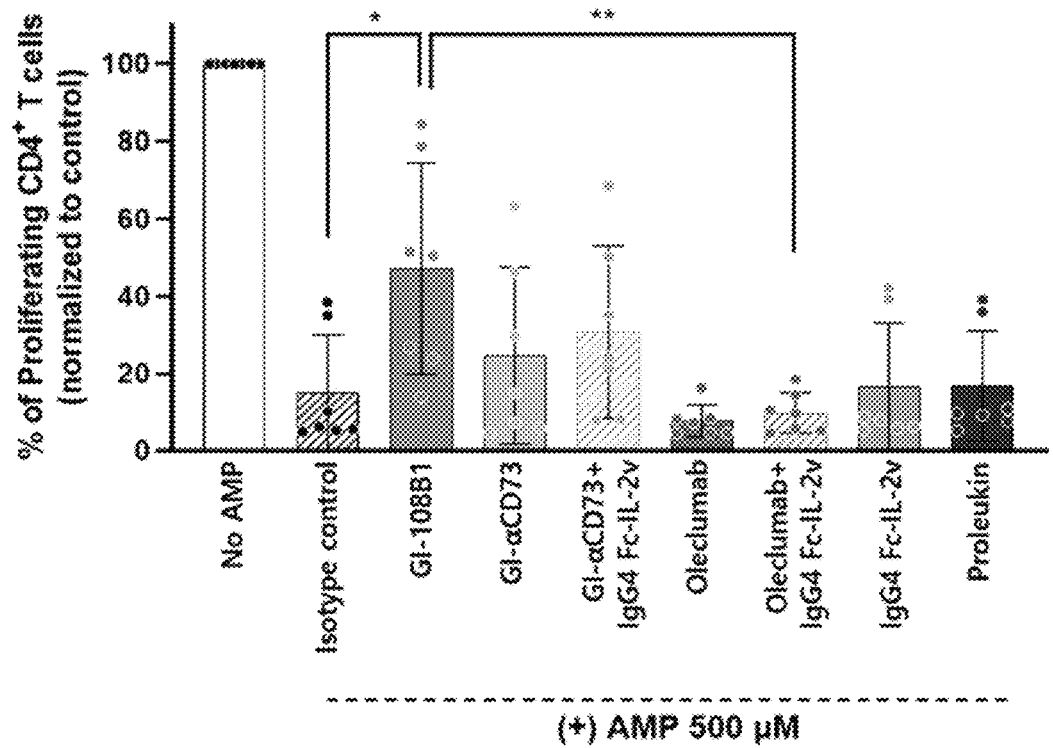
FIG. 9 is a graph showing the proliferation of CD4+ T cells after treating CD4+ T cells, the activity of which was inhibited by CD73-adenosine, with vehicle (hIgG4), GI-108B1 alone, PROLEUKIN® alone, IgG4 Fc-IL-2v alone, anti-CD73 antibody (GI-αCD73) alone, a combination of anti-CD73 antibody (GI-αCD73) and IgG4 Fc-IL-2v, oleclumab alone, or a combination of oleclumab and IgG4 Fc-IL-2v.
Figure 10:
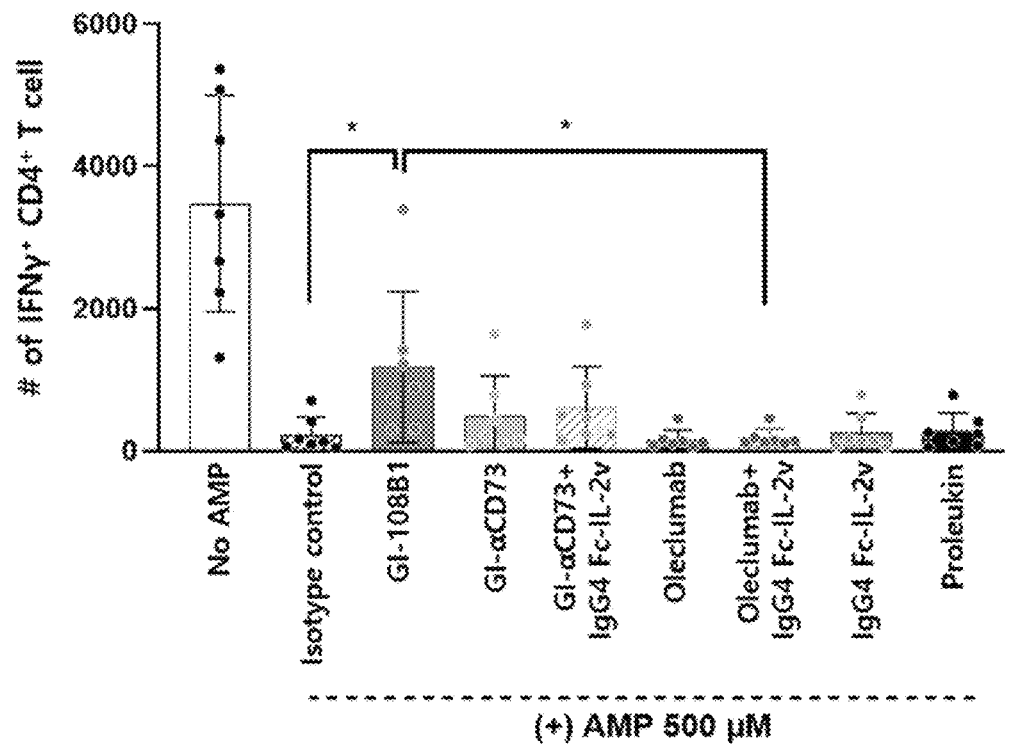
FIG. 10 is a graph showing the number of IFN-γ+CD4+ T cells after treating CD4+ T cells, the activity of which was inhibited by CD73-adenosine, with vehicle (hIgG4), GI-108B1 alone, PROLEUKIN® alone, IgG4 Fc-IL-2v alone, anti-CD73 antibody (GI-αCD73) alone, a combination of anti-CD73 antibody (GI-αCD73) and IgG4 Fc-IL-2v, oleclumab alone, or a combination of oleclumab and IgG4 Fc-IL-2v.

Furthermore, when treated with AMP and vehicle (hIgG4), the proliferation of CD4+ T cells was reduced. On the other hand, when treated with GI-108B1, the proliferation of CD4+ T cells significantly increased. In addition, the proliferation of CD4+ T cells increased even when treated with anti-CD73 antibody alone or with a combination of anti-CD73 antibody and IgG4 Fc-IL-2v. Meanwhile, when treated with PROLEUKIN®, Oleclumab or IgG4 Fc-IL-2v alone or when treated with a combination of Oleclumab and IgG4 Fc-IL-2v, the proliferation of CD4+ T cells did not tend to increase (FIG. 9). In addition, when treated with AMP and vehicle (hIgG4), the production of IFN-γ by CD4+ T cells was reduced. On the other hand, it was confirmed that when treated with GI-108B1, the production of IFN-γ by CD4+ T cells significantly increased (FIG. 10). Thereby, it was confirmed that GI-108B1 reinvigorated CD8+ T cell and CD4+ T cell activities suppressed by CD73-adenosine.

Example 11. Evaluation of GI-108B1 Activity Using pSTAT5 Analysis

To evaluate the activity of GI-108B1, healthy human PBMCs were treated with PROLEUKIN®, GI-108B1, IgG4 Fc-IL-2v and anti-CD73 antibody (GI-αCD73) alone, or a combination of anti-CD73 antibody (GI-αCD73) and IgG4 Fc-IL-2v, and pSTAT5 in T cell populations (CD8+ T cells and Treg cells) in the PBMCs was measured. Specifically, human PBMCs were treated with various concentrations of PROLEUKIN®, GI-108B1, IgG4 Fc-IL-2v, and anti-CD73 antibody alone, or with a combination of anti-CD73 antibody and IgG4 Fc-IL-2v, and incubated at 37° C. for 20 minutes. For cell surface staining, cells were stained with the following antibodies: anti-CD3-BV510 (Clone SP34-2, BD Biosciences), anti-CD4-PE-Cy7 (Clone OKT-4, Biolegend Inc.), anti-CD8-AF700 (Clone RPA-T8, Biolegend Inc.), anti-CD25-BV421 (Clone M-A251, BD Biosciences), anti-CD56-BV605 (Clone NCAM16.2, BD Biosciences), anti-CD127-BV650 (Clone A019DS, Biolegend Inc.), and Fixable Viability Dye eFluor 780 (Invitrogen Inc.).

For intracellular staining, the cells were fixed for 12 minutes by treatment with TFP Fix/Perm buffer (BD Biosciences), and incubated with Perm buffer III (BD Biosciences) for 30 minutes. The cells were then stained with anti-pSTAT5-AF647 (Clone 47/Stat5, BD Biosciences). Data on the stained cells were measured using Cytek Aurora (Cytek Biosciences) and analyzed using FlowJo software (BD Biosciences).

Figure 11:
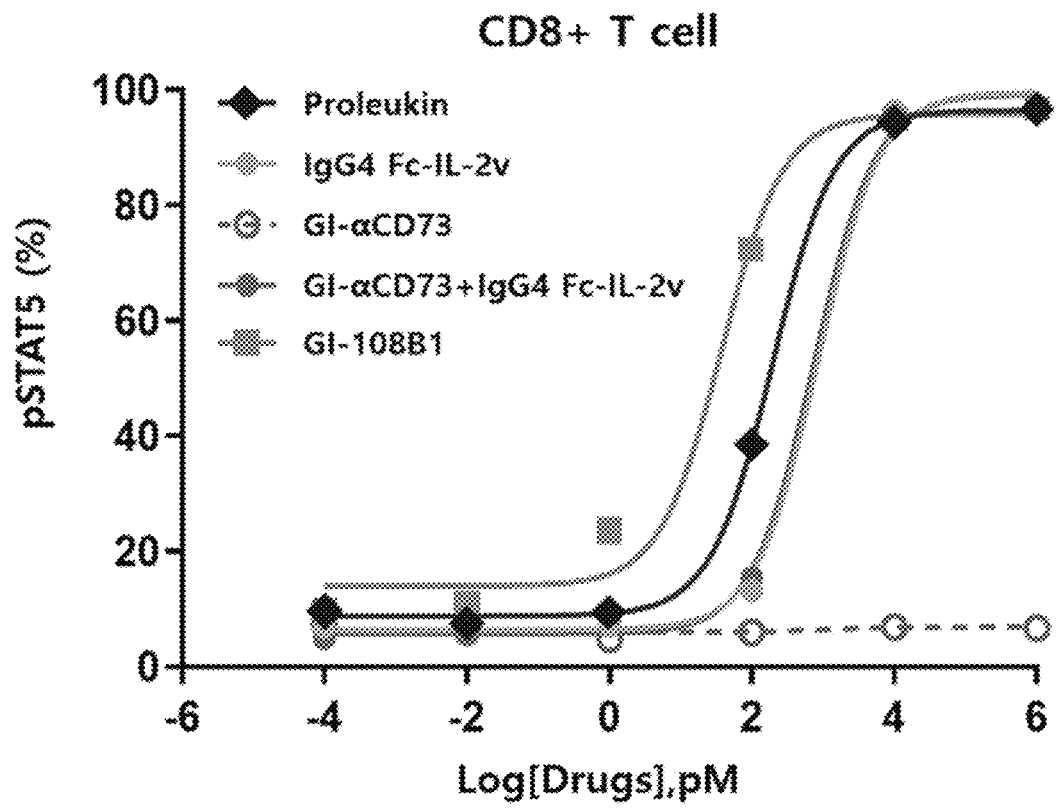
FIG. 11 is a graph showing the results of measuring pSTAT5 in the CD8+ T cell population after treating human PBMCs with various concentrations of PROLEUKIN®, GI-108B1, anti-CD73 antibody (GI-αCD73) or IgG4 Fc-IL-2v alone, or a combination of anti-CD73 antibody (GI-αCD73) and IgG4 Fc-IL-2v.
Figure 12:
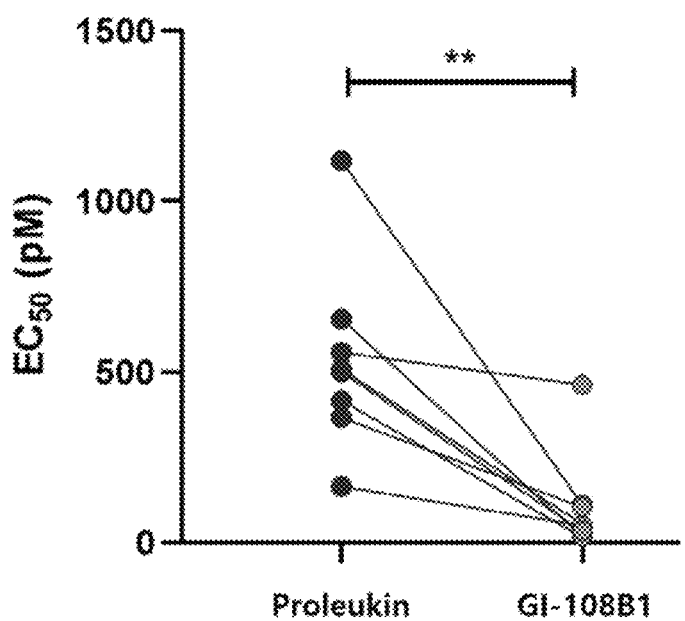
FIG. 12 is a graph showing the $EC_{50}$ values obtained by measuring pSTAT5 in the CD8+ T cell population after treating human PBMCs with various concentrations of PROLEUKIN® or GI-108B1.

As a result, it was confirmed that the $EC_{50}$ value of GI-108B1 against pSTAT5 in CD8+ T cells was significantly lower than that in the group treated with PROLEUKIN®, IgG4 Fc-IL-2v or anti-CD73 antibody alone or with a combination of anti-CD73 antibody and IgG4 Fc-IL-2v. Thereby, it was confirmed that GI-108B1 exhibited a better effect against STAT5 activation in CD8+ T cells than PROLEUKIN® (FIGS. 11 and 12).

Figure 13:
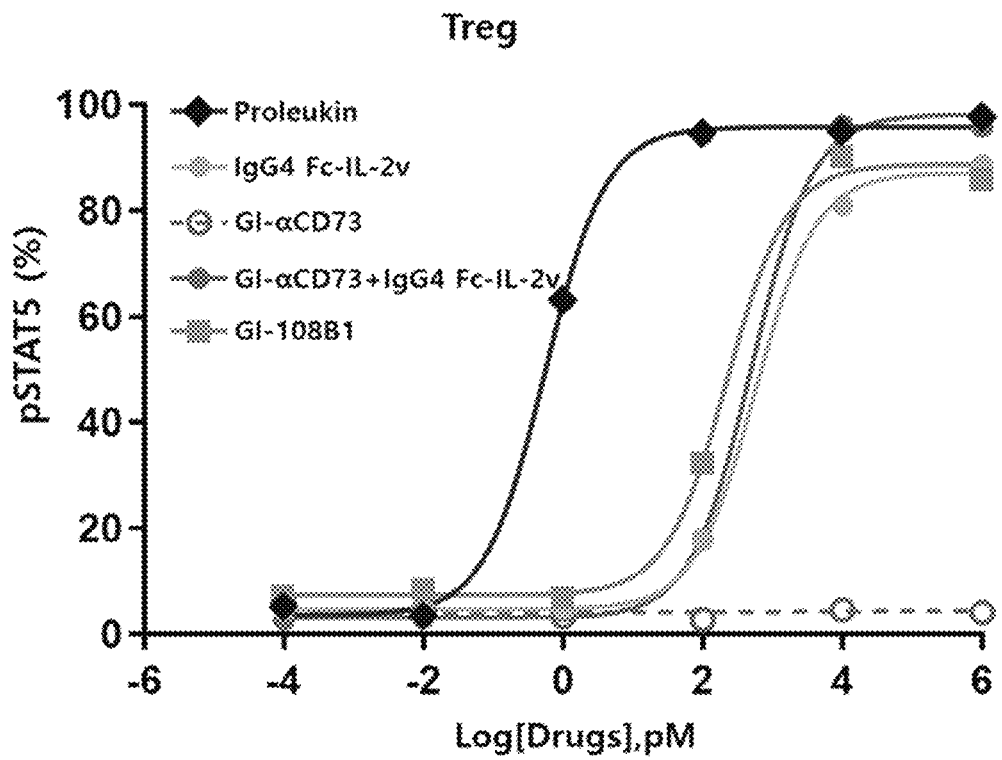
FIG. 13 is a graph showing the results of measuring pSTAT5 in the Treg cell population after treating human PBMCs with various concentrations of PROLEUKIN®, GI-108B1, anti-CD73 antibody (GI-αCD73) or IgG4 Fc-IL-2v alone, or a combination of anti-CD73 antibody (GI-αCD73) and IgG4 Fc-IL-2v.
Figure 14:
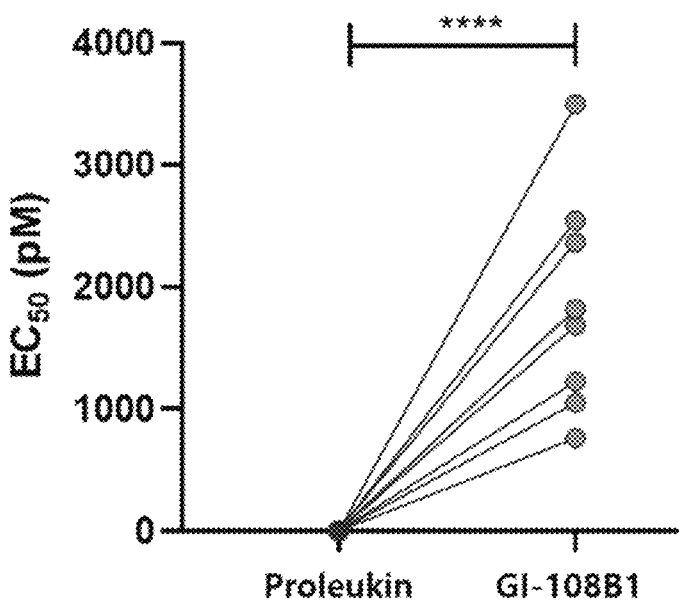
FIG. 14 is a graph showing the $EC_{50}$ values obtained by measuring pSTAT5 in the Treg cell population after treating human PBMCs with various concentrations of PROLEUKIN® or GI-108B1.

In addition, it was confirmed that the $EC_{50}$ value of GI-108B1 against pSTAT5 in Treg cells was slightly higher than that in the group treated with IgG4 Fc-IL-2v or anti-CD73 antibody alone or with a combination of anti-CD73 antibody and IgG4 Fc-IL-2v, and was significantly higher than that in the group treated with PROLEUKIN®. Thereby, it was confirmed that GI-108B1 was much less effective in activating STAT5 in Treg cells compared to PROLEUKIN® (FIGS. 13 and 14).

Example 12. Evaluation of T-Cell Proliferation Ability of GI-108B1

Human PBMCs were suspended in 4Cell® Nutri-T GMP medium (Sartorius), and the cells were dispensed in a 96-well plate at a density of $5 \times 10^5$ cells per well. Then, the cells were treated with GI-108B1 or PROLEUKIN® at a final concentration of 10 nM in the presence of αCD3/CD28 dynabeads (1:1 ratio, Thermo Fisher Scientific). Every 2 to 3 days, the medium was replaced with a fresh medium containing each drug. The cells were counted on days 3, 5, 7, 10, and 12 using the ADAM™-MC2 Cell Counter (Nanoentek). On day 12, $2 \times 10^6$ cells of each group were stained with the following antibodies: anti-CD3-BV510 (Clone SP34-2, BD Biosciences), anti-CD4 (Clone OKT-4, Biolegend Inc.), anti-CD8-AF700 (Clone RPA-T8, Biolegend Inc.), anti-CD25-BV421 (Clone M-A251, BD Biosciences), anti-CD45-APC (Clone HI30, eBioscience), and Fixable Viability Dye eFluor 780 (Invitrogen Inc.). For intracellular staining, the cells were treated with fixation/permeabilization buffer (BD Biosciences) and stained with anti-Foxp3-PE antibody (Clone PCH101, Invitrogen Inc.). Data on the stained cells were measured using the Cytek Aurora instrument and analyzed using FlowJo software.

Figure 15:
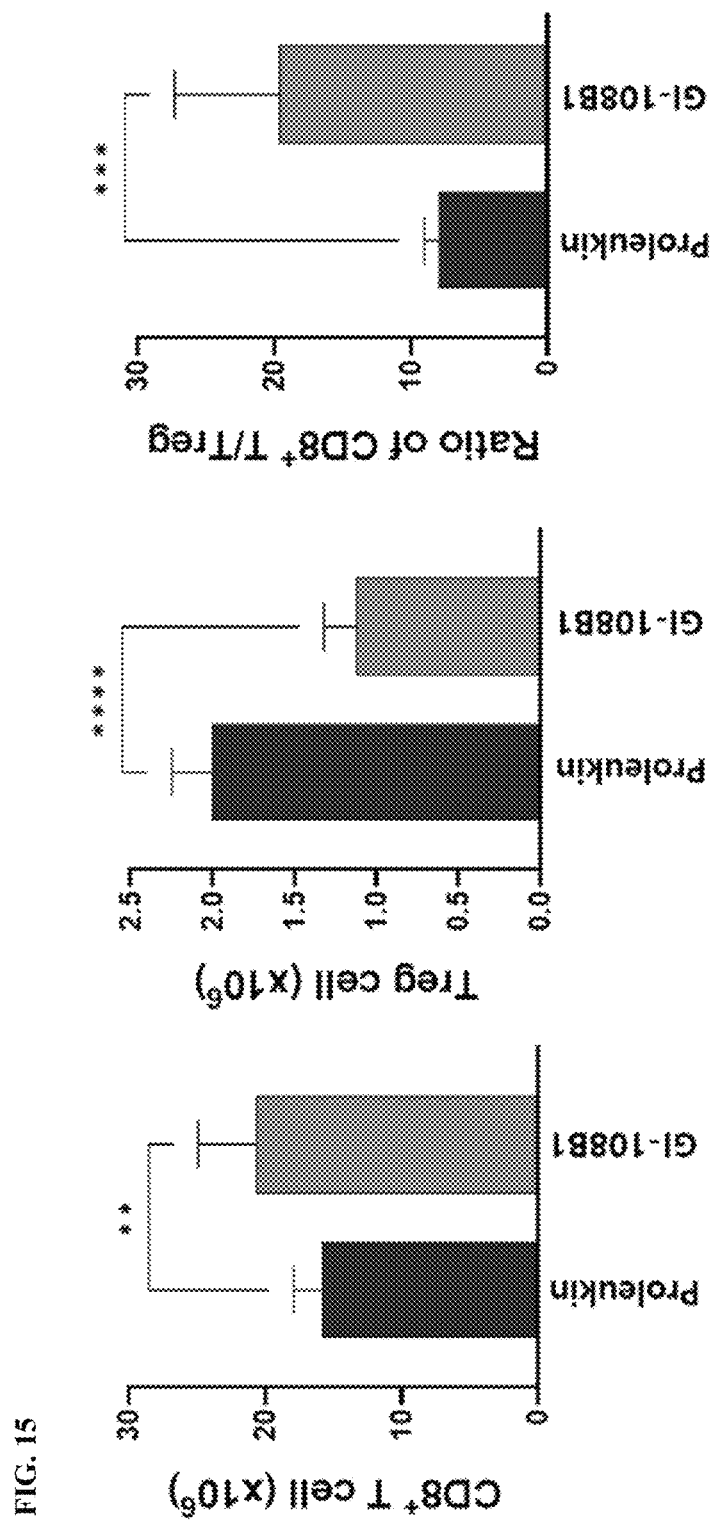
FIG. 15 shows the results of measuring the number of CD8+ T cells, the number of Treg cells, and the CD8+ T/Treg ratio after 12 days of culture of human PBMCs treated with PROLEUKIN® or GI-108B1.

As a result, the number of CD8+ T cells in the group treated with GI-108B1 was higher than in the group treated with PROLEUKIN®, and the number of Treg cells was about 2-fold higher in the group treated with PROLEUKIN® than in the group treated with GI-108B1. As a result of calculating the ratio of the number of CD8+ T cells to the number of Treg cells (CD8+T/Treg), it was confirmed that the CD8+T/Treg in the group treated with GI-108B1 was about 2.46-fold higher than that in the group treated with PROLEUKIN®. Thereby, it was confirmed that GI-108B1 exhibited a superior effect on CD8+ T cell proliferation over Treg cell proliferation compared to PROLEUKIN® (FIG. 15).

Example 13. Cis-Binding Analysis of GI-108B1 in CD8+ T Cells

Figure 16:
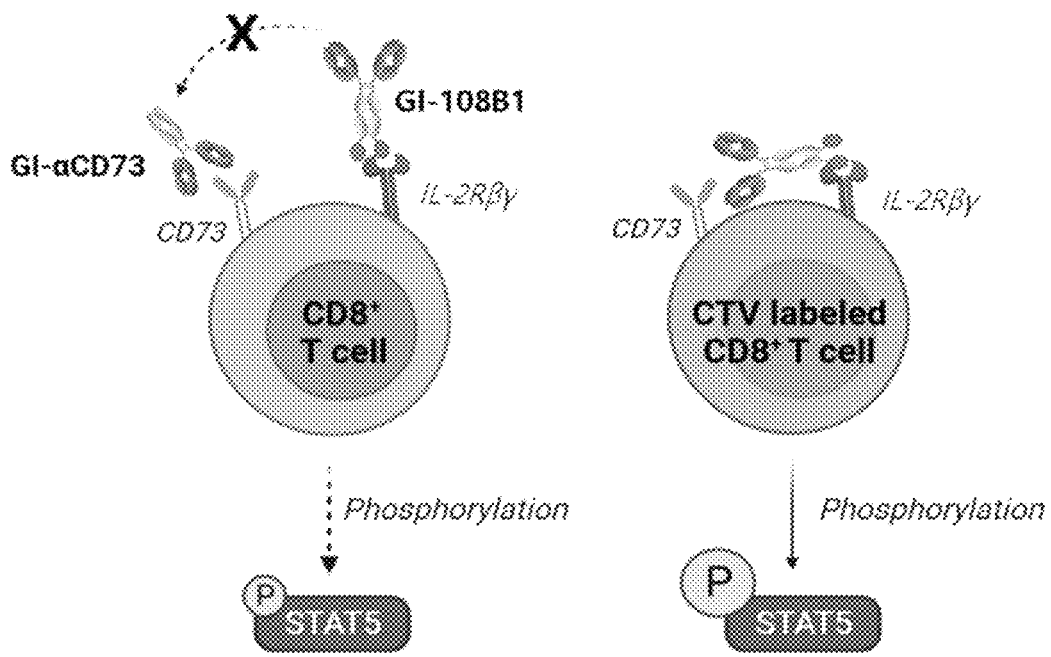
FIG. 16 schematically illustrates that STAT5 phosphorylation is induced when GI-108B1 cis-binds to CD73 and IL-2 receptors in the CD8+ T cells and CTV+CD8+ T cells pretreated with anti-CD73 antibody.

CD8+ T cells express both CD73 and the IL-2 receptor complex, so signaling induced by the binding of GI-108B1 to CD73 and IL-2βγ on the same CD8+ T cells can exhibit a synergistic effect on the activation of CD8+ T cells. Accordingly, to examine whether GI-108B1 cis-binds to CD73 and IL-2βγ on the same CD8+ T cells, cis-binding analysis was performed using CTV-CD8+ T cells (anti-CD73 antibody-treated/untreated group) and CTV+CD8+ T cells (FIG. 16). Specifically, CD8+ T cells were isolated from human PBMCs using the EASYSEP™ Human CD8+

T Cell Isolation Kit (STEMCELL technologies). Half of the isolated CD8+ T cells were labeled with 0.5 μM CTV (Cell Trace™ Violet, Thermo Fisher Scientific). The CTV-unlabeled cells were divided into two groups, and one group was pre-treated with a saturating concentration (1,000 nM) of anti-CD73 antibody at 4° C. for 2 hours to block all CD73 on the cell surface. Then, unbound anti-CD73 antibody was washed out.

Then, the CTV-unlabeled cells, pre-treated or untreated with anti-CD73 antibody were co-cultured with CTV-labeled cells at a 1:1 ratio. The co-cultured cells were treated with 0.5 nM GI-108B1 and incubated at 37° C. for 20 minutes. Thereafter, the cells were fixed with Cytofix fixation buffer (BD Biosciences) for 12 minutes, and then treated with Phosflow Perm buffer III (BD Biosciences) and incubated for 30 minutes. The cells were then stained with anti-pSTAT5-AF647 (Clone 47/Stat5, BD Biosciences). Data for the stained cells were measured using Cytek Aurora and analyzed using FlowJo software.

Figure 17:
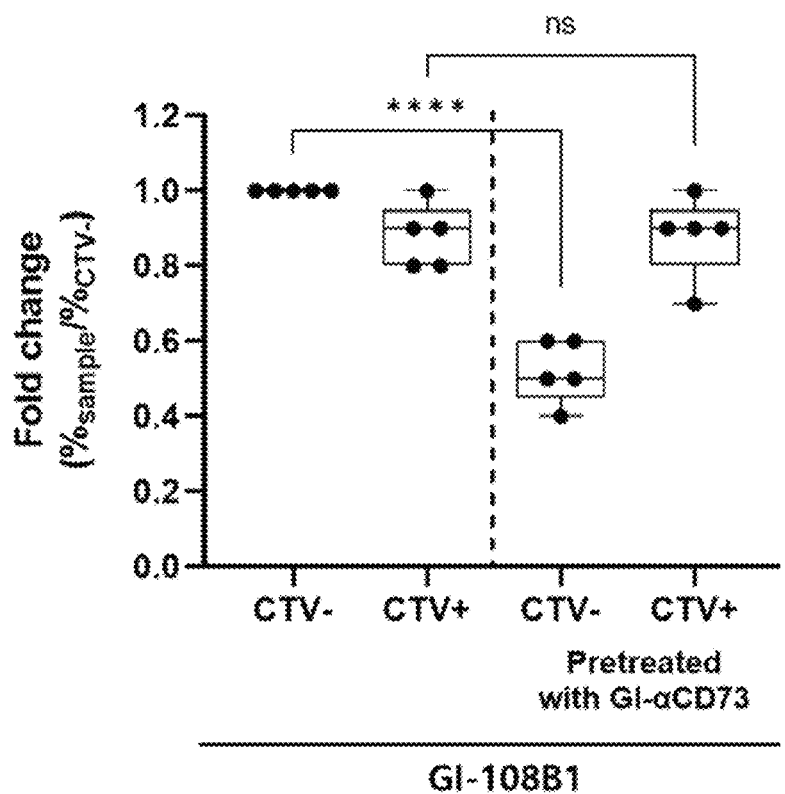
FIG. 17 is a graph showing the results of measuring pSTAT5+(CTV+/−)CD8+ T cells in a co-culture sample of CTV+CD8+ T cells and CD8+ T cells pretreated with anti-CD73 antibody and a co-culture sample of CTV+CD8+ T cells and CD8+ T cells after treating each of the samples with GI-108B1.
Figure 18:
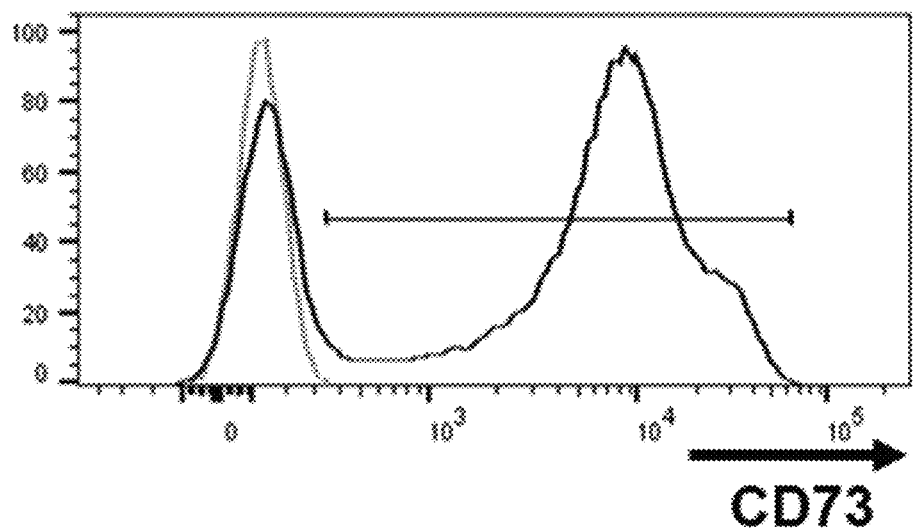
FIG. 18 is a graph showing the results of flow cytometry analysis of hCD73+CD8+ T cells in purified CD8+ T cells from human PBMCs.

As a result, it was confirmed that, in the case of CTV+ CD8+ T cells co-cultured with CTV-CD8+ T cells that were not pre-treated with anti-CD73 antibody, CTV-CD8+ T cells and CTV+CD8+ T cells showed similar levels of STAT5 phosphorylation, but in the case of CTV+CD8+ T cells co-cultured with CTV-CD8+ T cells pretreated with anti-CD73 antibody, the STAT5 phosphorylation level in CTV-CD8+ T cells was reduced by 40 to 60%, and the STAT5 phosphorylation level in CTV+CD8+ T cells remained the same (FIG. 17). From the fact that the proportion of hCD73+ CD8+ T cells expressing hCD73 in purified CD8+ T cells from PBMCs was about 70% (FIG. 18) and from the above results, it was confirmed that GI-108B1 preferentially cis-binds to CD73 in CD8+ T cells expressing CD73.

III. Evaluation of Anticancer Effect of Fusion Protein Dimer

Example 14. Evaluation of Immune Cell-Mediated Tumor Killing Ability of GI-108B1

To evaluate the immune cell-mediated tumor killing ability of GI-108B1, the anticancer effect of GI-108B1 was evaluated using a co-culture system of MDA-MB-231 cells and healthy human PBMC in the presence of anti-CD3/CD28 dynabeads and/or AMP. Specifically, the cytotoxicity of PBMCs against MDA-MB-231 wild-type cells was evaluated using flow cytometry-based Annexin V/7-AAD assay. PBMCs were purchased from Zen-bio Inc. or STEMCELL Technologies.

PBMCs were treated with hIgG4 (5 nM) alone, a combination of anti-CD73 antibody (GI-αCD73, 5 nM) and IgG4 Fc-IL-2v (5 nM), or GI-108B1 (5 nM) alone, and also treated with αCD3/CD28 dynabeads (1:1 ratio) or 500 UM of AMP and cultured for 2 days before co-culture with target cells (MDA-MB-231 wild-type cells). Target cells were labeled with CTV and dispensed into a 24-well plate at a density of 1×10⁵ cells per well. After overnight culture, pre-stimulated PBMCs were added to the target cells at a ratio of effector cells to target cells of 10:1, followed by co-culture for 24 hours at 37° C. under 5% $CO_2$. The cells were stained with Annexin V and 7-AAD (Biolegend Inc.), and the death rate of the CTV-labeled target cells was measured using the Symphony A3 instrument and analyzed using FlowJo software.

As a result, it was confirmed that the cell death rate was higher in the group (isotype control group (−AMP)) in which PBMCs treated only with anti-CD3/CD28 dynabeads and hIgG4 were co-cultured with target cells than in the group (isotype control group (+AMP)) in which PBMCs treated with anti-CD3/CD28 dynabeads, AMP, and hIgG4 were co-cultured with target cells. Thereby, it was confirmed that the activity (cell killing ability) of immune cells was inhibited by treatment with AMP under adenosine-rich conditions.

Figure 19:
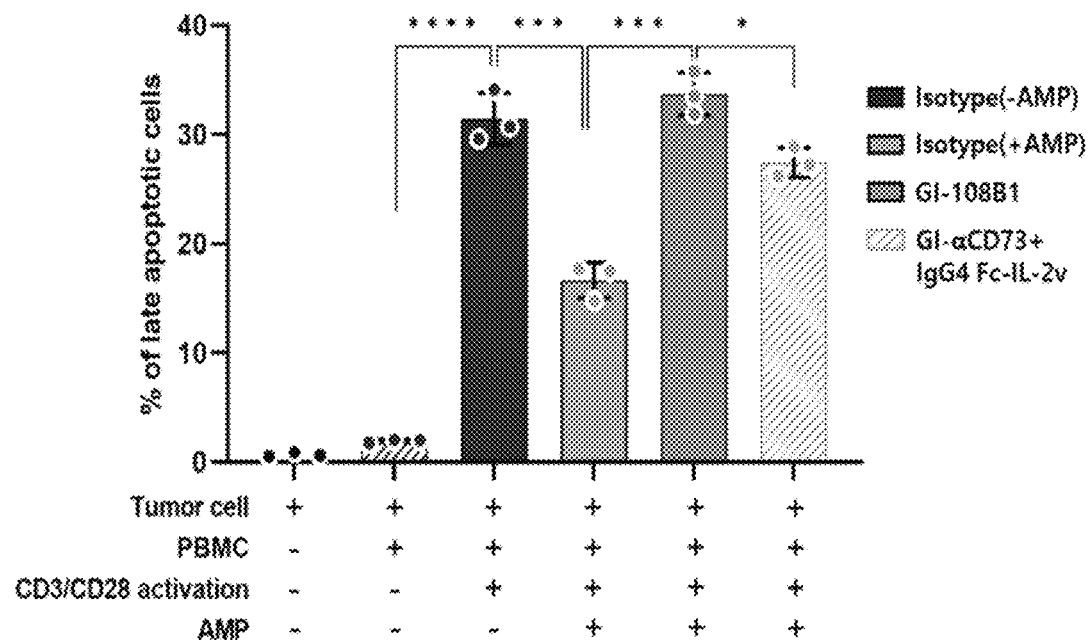
FIG. 19 is a graph showing the results of measuring the cell death rate after co-culture of MDA-MB-231 cells and PBMCs, treated with hIgG4 or GI-108B1 alone or a combination of anti-CD73 antibody (GI-αCD73) and IgG4 Fc-IL-2v, in the presence of anti-CD3/CD28 dynabeads and/or AMP.

Meanwhile, even though treated with AMP, the group in which PBMCs treated with anti-CD3/CD28 dynabeads, AMP and GI-108B1 were co-cultured with target cells and the group in which PBMCs treated with anti-CD3/CD28 dynabeads, AMP, and a combination of anti-CD73 antibody (GI-αCD73) and IgG4 Fc-IL-2v were co-cultured with target cells all showed higher cell death rates than the isotype control group (+AMP). In particular, the group in which PBMCs treated with anti-CD3/CD28 dynabeads, AMP and GI-108B1 were co-cultured with target cells showed a significantly higher target-cell death rate than the group in which PBMCs treated with anti-CD3/CD28 dynabeads, AMP and a combination of anti-CD73 antibody (GI-αCD73) and IgG4 Fc-IL-2v were co-cultured with target cells, indicating the highest cell death rate (FIG. 19).

Example 15. Evaluation of Anticancer Effect of GI-108B1 Administration in Mice Transplanted with Murine Colon Cancer Cells After the test substance GI-108B1 was administered to a tumor model transplanted with the MC38 cell line (MC38-hCD73), a C57BL/6 murine colon cancer cell line in which the mouse CD73 gene was replaced with the human CD73 gene, the tumor growth inhibitory effect was evaluated. First, to produce a mouse model transplanted with a cancer cell line, a suspension of MC38-hCD73 cells (SMOC, China) was administered subcutaneously to the right back of each of C57BL/6J-hCD73 female mice (6-8 weeks old, SMOC, China) at 1×10⁶ cells/100 μL.

After MC38-hCD73 cells were transplanted, morbidity and mortality were checked daily, tumor volumes were measured for mice with no abnormalities in health, and 16 mice were randomly selected when the average tumor volume was 90 to 120 mm³. The animals were selected considering their physiological state, weight change, and tumor growth rate. The selected animals were divided into groups (n=8) as evenly as possible based on the tumor volume and body weight. Test groups were formed as shown in Table 10 below, and the test substance was administered thereto.

TABLE 10

| Group | Substance administered | Route of administration | Dosing cycle | Dose | Animal number (n) |
|---|---|---|---|---|---|
| G1 | Vehicle (PBS) | i.v | QW (three times/3 weeks) | — | 8 |
| G2 | GI-108B1 | i.v. | QW (three times/3 weeks) | 6 mg/kg | 8 |

During the test period, changes in tumor, body weight, and diet were observed regularly, and changes in body weight and external appearance (hair/black eye) were checked twice a week. For tumor volume measurement, the maximum length (L) and perpendicular width (W) of the tumor were measured twice a week during the observation period using a digital caliper (Mitutoyo, Japan). Tumor volume (TV) and tumor growth inhibition (TGI) were measured by substituting the measured values into Equation I below.

$$TV(\text{mm}^3) = (W^2 \times L)/2 \qquad < \text{Equation I} >$$

$$TGI = (1-(Ti-T0)/(Vi-V0)) \times 100$$

Figure 20:
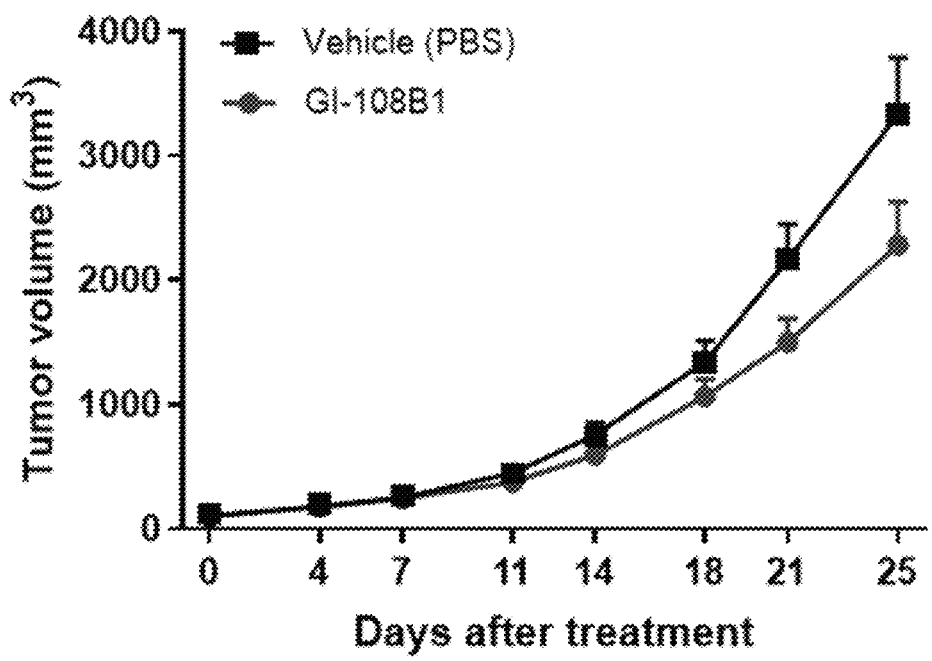
FIG. 20 is a graph showing the results of measuring the tumor volume after administering vehicle (PBS) or GI-108B1 to mice transplanted with murine colon cancer cells (MC38).
Figure 21:
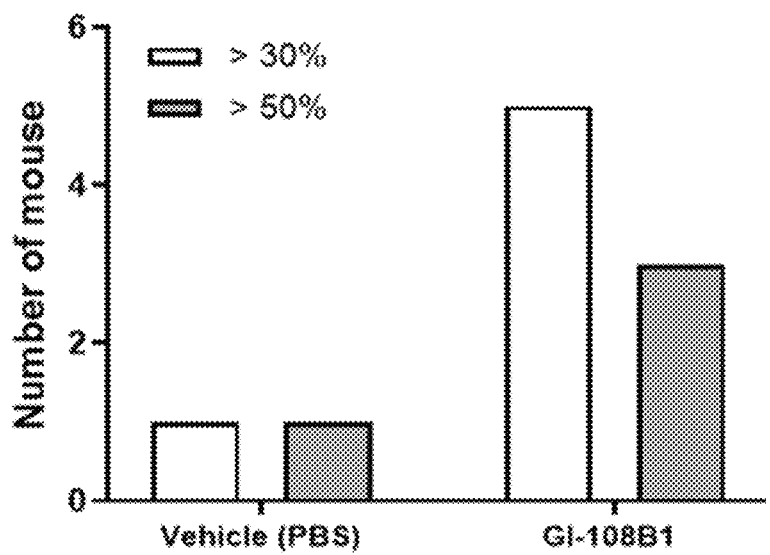
FIG. 21 is a graph showing the tumor growth inhibition rate after administering vehicle (PBS) or GI-108B1 to mice transplanted with murine colon cancer cells (MC38).
Figure 22:
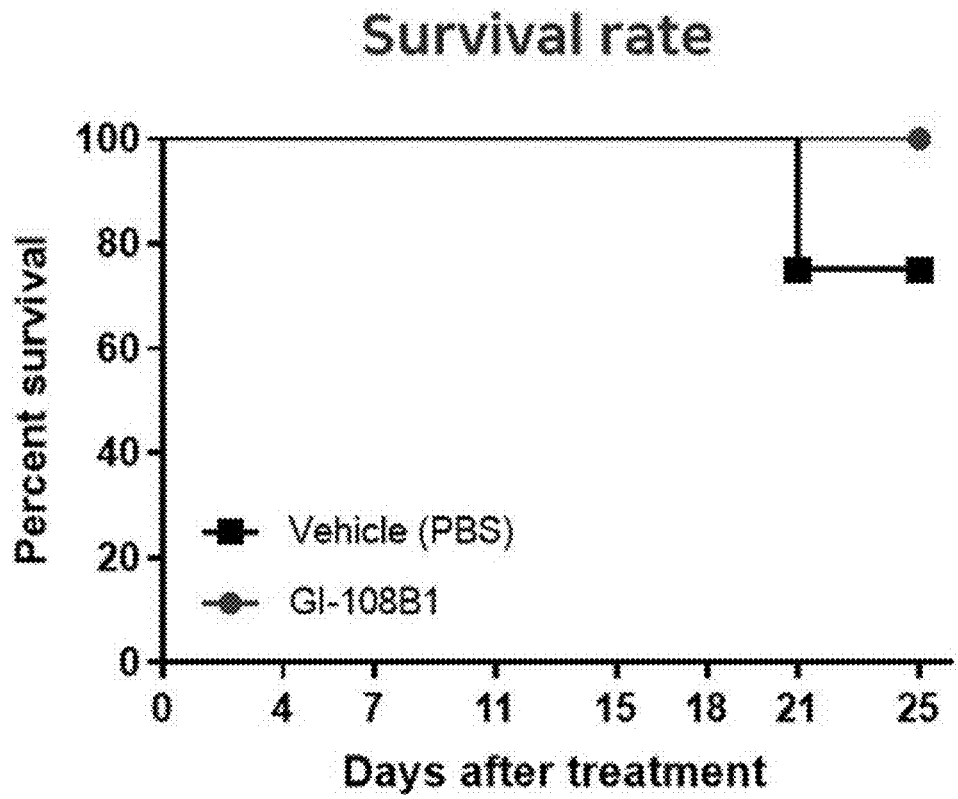
FIG. 22 is a graph showing the survival rate up to day 25 after administering vehicle (PBS) or GI-108B1 to mice transplanted with murine colon cancer cells (MC38).

Ti: tumor volume in the test substance-administered group at the end of the test
T0: tumor volume in the test substance-administration group at the time of first administration
Vi: tumor volume in the negative control group at the end of the test
V0: tumor volume in the negative control group at the time of first administration The tumor volume in each animal before administration was set as the value measured at the time of grouping, and the antitumor efficacy was evaluated by comparison with the control group (vehicle (PBS), G1). As a result, the tumor volume in the GI-108B1-administered group was reduced compared to the control group (vehicle (PBS)) (FIG. 20). In addition, regarding the tumor growth inhibition rate, only one mouse in the control group (vehicle (PBS)) showed a tumor growth inhibition rate of over 50%, and none showed over 80%. On the other hand, in the GI-108B1-administered group, 5 mice showed a tumor growth inhibition rate of over 30%, and 3 mice over 50% (FIG. 21). Furthermore, when checking the survival rate of mice in each group, 2 mice in the control group (vehicle (PBS)) died on day 25, whereas all mice in the GI-108B1-administered group survived on day 25 (FIG. 22).

Example 16. Evaluation of Anticancer Effect of GI-108 Administration in Mice Transplanted with Human Breast Cancer Cells In a tumor model obtained by transplanting MDA-MB-231 cells (human breast cancer cells) into mice into which the human immune system has been introduced, each of test substances GI-108A1 (AHP04167), GI-108B1, and Pembrolizumab (product name: Keytruda, MSD), an anti-PD-1 antibody, was administered, and then the tumor growth inhibitory effect was evaluated. First, in order to produce a mouse model into which the human immune system has been introduced, a suspension of human peripheral blood cells (Stemexpress, USA) was filled into a disposable syringe (31G, cat. 328820, BD, USA) and administered to NOG-B2m (NOD.Cg-B2mtm1UncPrkdcscidIl2rgtm1Wjl/SzJ) female mice (7-week-old, The Jackson Laboratory, USA) through the caudal vein at 1×10⁷ cells/200 μL per animal. After cell transplantation, general symptoms were observed once daily.

NOG-B2m female mice were purchased from The Jackson Laboratory, and NOG-B2m female mice were maintained in individually ventilated cages housed in an animal biosafety level-3 facility at 19 to 25° C. and 30 to 70% humidity.

The MDA-MB-231 human triple-negative breast cancer (TNBC) cell line was purchased from ATCC and cultured in DMEM medium (Thermo Fisher Scientific) containing 10% FBS (Thermo Fisher Scientific) and 1% antibiotic/antimycotic (GIBCO™). The cultured MDA-MB-231 cells were harvested using trypsin (GIBCO™) and then suspended in PBS. To establish a xenograft mouse tumor model, healthy mice 5 days after transplantation with human peripheral blood cells were used, and a solution prepared by mixing a MDA-MB-231 cell suspension (5×10⁶ cells/0.025 mL) and 0.025 mL Matrigel matrix phenol red-free (cat. 356237, BD, USA) was filled into a disposable syringe (31G, cat. 328820, BD, USA) and administered to subcutaneously to the right back of each of the animals at 0.05 mL per animal. After MDA-MB-231 cell transplantation, general symptoms were observed once daily during the engraftment and growth period.

Figure 23:
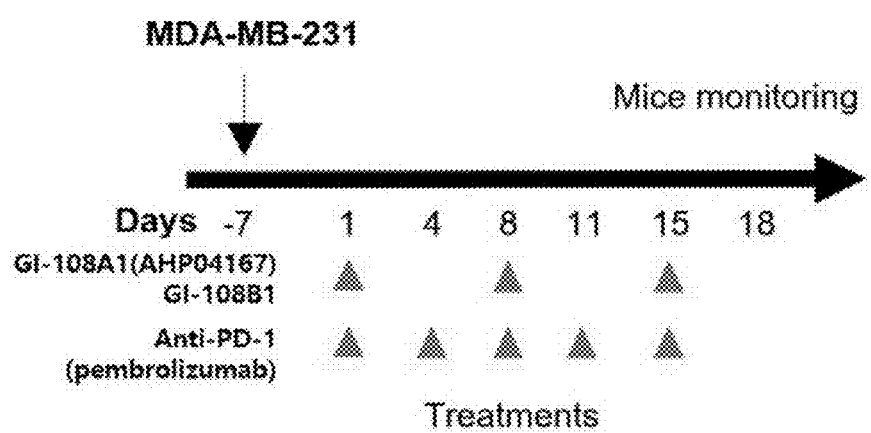
FIG. 23 schematically shows an experimental plan conducted using mice transplanted with human breast cancer cells (MDA-MB-231) in order to evaluate the anticancer effects of GI-108A1 and GI-108B1.

About 20 days after transplanting the MDA-MB-231 cells, the tumor volume was measured in mice with no abnormalities in health, and 32 mice were selected so that the average tumor volume of each group reached 80 to 100 mm³. The animals were selected considering their physiological state (respiration, fur, behavior, tail, posture, body fluids, diet, morphological deformation, metabolism, etc.), weight change, FACS analysis results, and tumor growth rate. The selected animals were divided into groups (n=8) as evenly as possible based on the tumor volume and body weight. It was confirmed that the proportion of human CD45+ cells in the total lymphocytes in the mouse peripheral blood before grouping was over 80%. The test groups were formed as shown in Table 11 below and the test substances were administered thereto (FIG. 23).

TABLE 11

| Group | Substance administered | Route of administration | Dosing cycle | Dose | Animal number |
|---|---|---|---|---|---|
| G1 | Vehicle (hIgG4) | i.v. | QW (three times/2.5 weeks) | 6 mg/kg | 8 |
| G2 | GI-108A1 (AHP04167) | i.v. | QW (three times/2.5 weeks) | 6 mg/kg | 8 |
| G3 | GI-108B1 | i.v. | QW (three times/2.5 weeks) | 6 mg/kg | 8 |
| G4 | Anti-PD-1 (pembrolizumab) | i.v. | BIW (5 times/2.5 weeks) | 5 mg/kg | 8 |

During the test period, general symptoms such as appearance, behavior, and excrement were observed once a day and recorded for each mouse, and dead animals were checked. For body weight measurement and tumor volume measurement, the maximum length (L) and perpendicular width (W) of the tumor were measured twice a week during the observation period using a digital caliper. Tumor volume (TV) and tumor growth inhibition (TGI) were measured by substituting the measured values into Equation I described in Example 15. The tumor volume in each animal before administration was set as the value measured at the time of grouping, and the antitumor efficacy was evaluated by comparison with the control group (vehicle, G1).

All statistical calculations were performed using Prism 8.0 (Graph Pad Software Inc, USA). Comparison of tumor volume measurements was done using unpaired t-test. A p value of less than 0.05 was considered significant.

Figure 24:
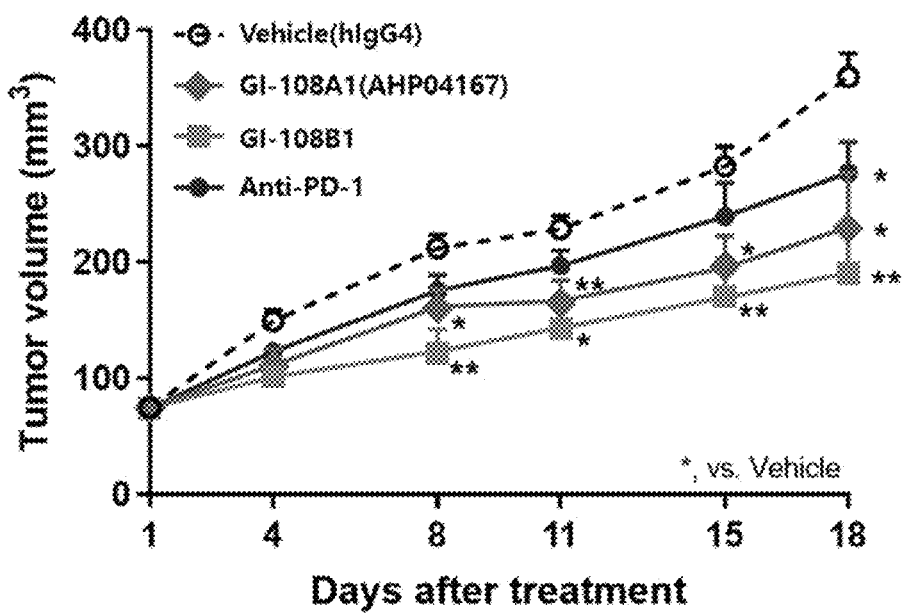
FIG. 24 is a graph showing the results of measuring the tumor volume up to day 18 after administering vehicle (hIgG4), GI-108A1 (AHP04167), GI-108B1, or anti-PD-1 antibody to mice transplanted with human breast cancer cells (MDA-MB-231).
Figure 25:
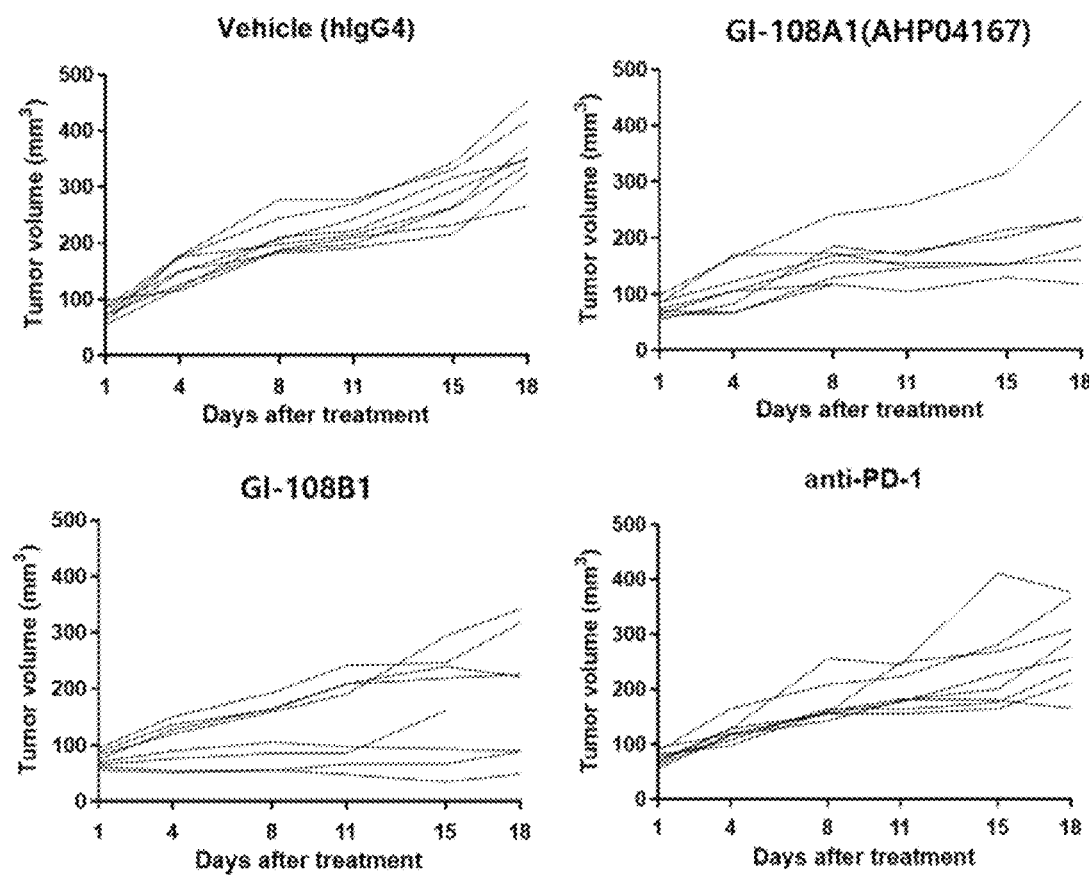
FIG. 25 is a graph showing the results of measuring the tumor volumes in individual experimental animals of each treated group after administering vehicle (hIgG4), GI-108A1 (AHP04167), GI-108B1, or anti-PD-1 antibody to mice transplanted with human breast cancer cells (MDA-MB-231).
Figure 26:
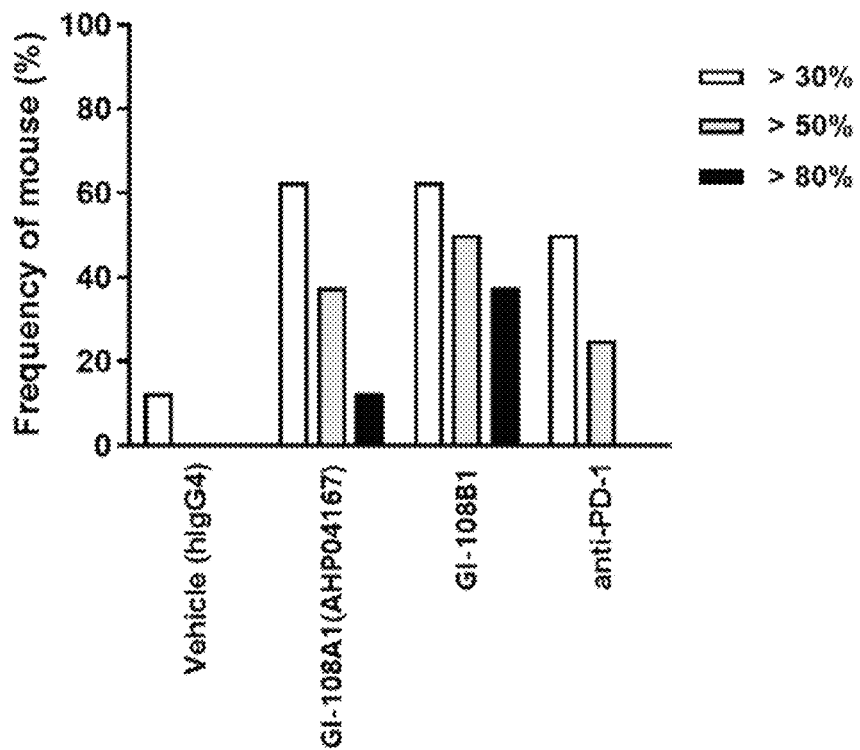
FIG. 26 is a graph showing the results of measuring the tumor growth inhibition rate on day 18 after administering vehicle (hIgG4), GI-108A1 (AHP04167), GI-108B1, or anti-PD-1 antibody to mice transplanted with human breast cancer cells (MDA-MB-231).

As a result, it was confirmed that tumor growth was inhibited in the groups treated with GI-108A1 (AHP04167), GI-108B1, and anti-PD-1 antibody compared to the control group (vehicle). In particular, the GI-108B1-administered group showed significantly more suppressed tumor growth than the GI-108A1 (AHP04167) or anti-PD-1 antibody-administered group (FIGS. 24 and 25). In addition, when the tumor growth inhibition rate was measured on day 18, only one mouse in the control group showed a tumor growth inhibition rate of over 30%, with none showing over 50% or 80%. In the anti-PD-1 antibody-administered group, 4 mice showed a tumor growth inhibition rate of over 30%, 2 mice over 50%, with none over 80%. On the other hand, in the GI-108A1-administered group, 5 mice showed a tumor growth inhibition rate of over 30%, 3 mice over 50%, and 1 mouse over 80%. In the GI-108B1-administered group, 5 mice showed a tumor growth inhibition rate of over 30%, 4 mice over 50%, and 3 mice over 80% (FIG. 26).

Figure 27:
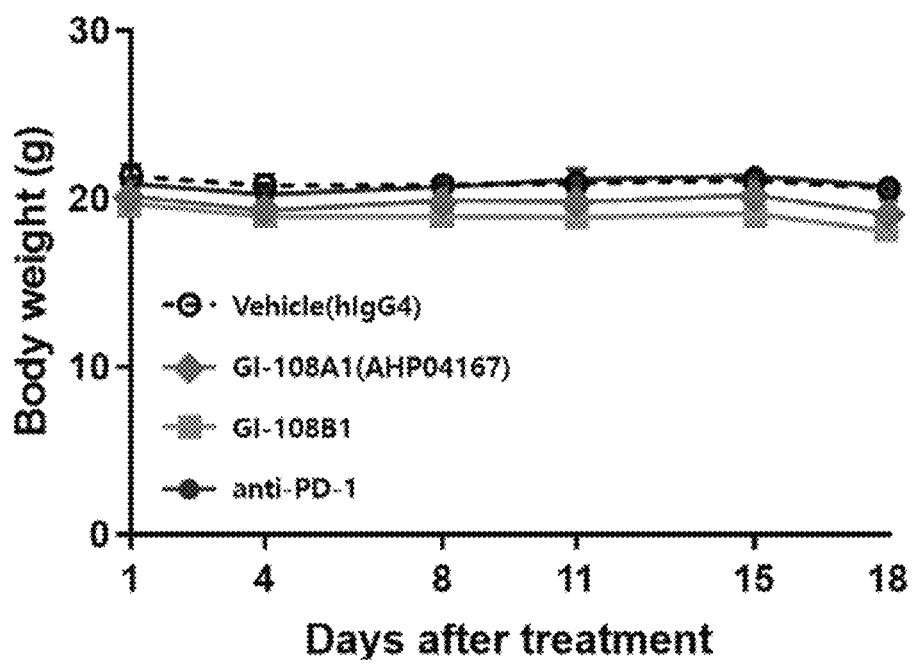
FIG. 27 is a graph showing the results of measuring the body weight of each mouse group up to day 18 after administering vehicle (hIgG4), GI-108A1 (AHP04167), GI-108B1, or anti-PD-1 antibody to mice transplanted with human breast cancer cells (MDA-MB-231).

Meanwhile, no weight loss appeared in both the control and test groups, and there was no significant difference between the groups (FIG. 27).

Example 17. Analysis of Vascular Permeability of GI-108B1

To analyze the vascular permeability of GI-108B1, $1 \times 10^5$ HUVEC cells (Lonza) were placed in a collagen-coated trans-well using a trans-well insert (9321012, CELLQART®), and cultured for 3 days to form a confluent monolayer. $1 \times 10^5$ PBMCs were dispensed into a 96-well plate, and then treated with PROLEUKIN® (5 nM) or GI-108B1 (5 nM) and cultured for 24 hours at 37° C. under 5% $CO_2$.

The HUVEC cells cultured in the trans-well were treated with the drug and the culture supernatant of the PBMCs and cultured for 24 hours at 37° C. under 5% $CO_2$. As a positive control, 100 ng/ml of TNF-α (PeproTech) was used. Thereafter, the upper chamber was treated with dextran-FITC (70 kDa) and incubated for 1 hour and 30 minutes. The fluorescence of dextran-FITC that moved to the lower chamber was measured at wavelengths of 485 nm/500-550 nm (Ex/Em) using GLOMAX® Discover (Promega). Statistical calculations were analyzed by one-way ANOVA using Prism 8.0 (Graph Pad Software Inc.), and Dunnett's test was performed based on the negative control.

Figure 28:
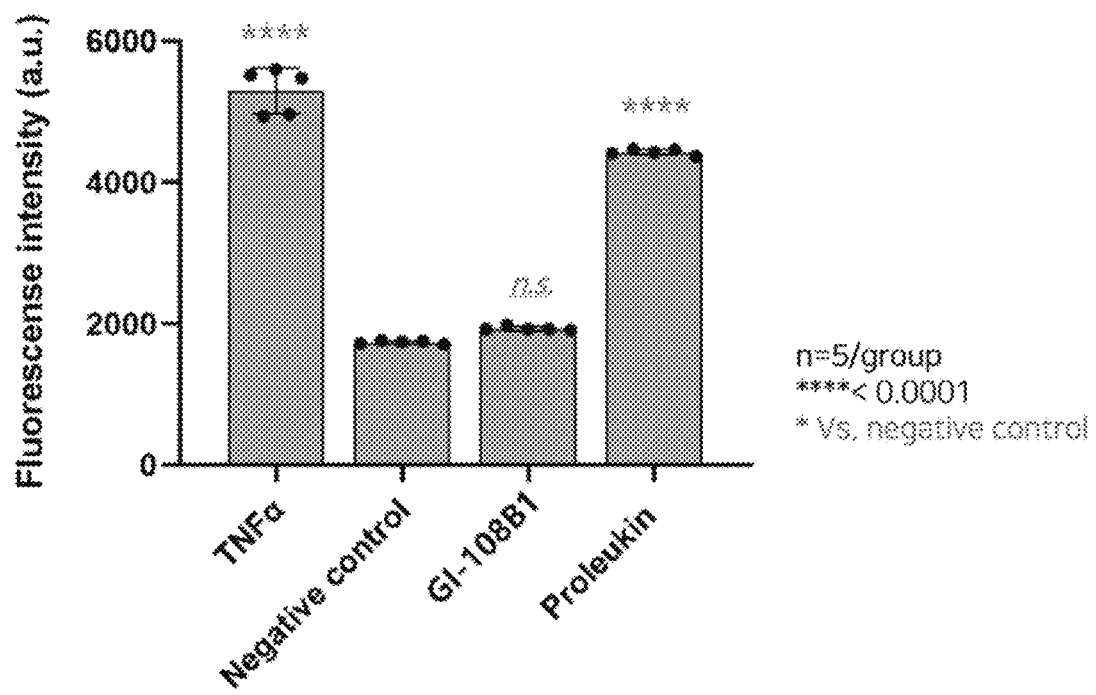
FIG. 28 is a graph showing the results of measuring the vascular permeability of each drug after treating and culturing HUVEC cells, cultured in a trans-well system, with a culture supernatant of PBMCs and TNF-α, PROLEUKIN® or GI-108B1.

As a result, increased vascular permeability was observed in the positive control group treated with TNF-α. On the other hand, the group treated with GI-108B1 showed a level of vascular permeability similar to that of the untreated negative control group (FIG. 28).

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereto.

---

The invention claimed is:

1. A fusion protein comprising: an antigen-binding fragment of an antibody that specifically binds to CD73; and an IL-2 variant,
wherein the fusion protein comprises the following structural formula (I):

$$\text{N'—X-[1}^{st}\text{ linker]}o\text{-Fc region-[2}^{nd}\text{ linker]}p\text{-Y—C'} \quad \text{(I)},$$

wherein
N' is the N-terminus,
C' is the C-terminus,
X is the antigen-binding fragment of an antibody that specifically binds to CD73,
Y is the IL-2 variant that comprises the sequence of SEQ ID NO: 40 with a modification, wherein the modification is one or more substitutions selected from the group consisting of R38A, F42A, and E61R with regard to the amino acid sequence of SEQ ID NO: 40,
$1^{st}$ linker and $2^{nd}$ linker are each a peptide linker, and
o and p are each independently 0 or 1,
wherein the antigen-binding fragment comprises a single-domain antibody comprising a CDR1 region comprising the amino acid sequence of SEQ ID NOs: 15, 18, or 21; a CDR2 region comprising the amino acid sequence of SEQ ID NOs: 16, 19, or 22; and a CDR3 region comprising the amino acid sequence of SEQ ID NOs: 17, 20, or 23, respectively.

2. The fusion protein of claim 1, wherein the antigen-binding fragment comprises any one amino acid sequence selected from the group consisting of SEQ ID NO: 2, SEQ ID NO: 3, and SEQ ID NO: 4.

3. The fusion protein of claim 1, wherein the $1^{st}$ linker comprises the amino acid sequence of SEQ ID NO: 5.

4. The fusion protein of claim 1, wherein the $2^{nd}$ linker comprises the amino acid sequence of SEQ ID NO: 7.

5. A fusion protein comprising: an antigen-binding fragment of an antibody that specifically binds to CD73; and an IL-2 variant,
wherein the fusion protein comprises a polypeptide chain of the following structural formula (II) and a polypeptide chain of the following structural formula (III):

$$\text{N'—X-[3}^{rd}\text{ linker]}q\text{-Fc region-[4}^{th}\text{ linker]}r\text{-Y—C''} \quad \text{(II); and}$$

$$\text{N'—X'—C'} \quad \text{(III)}$$

wherein, in the structural formulas (II) and (III),
N' is the N-terminus,
C' is the C-terminus, X is the antigen-binding fragment comprising a heavy chain variable region (VH) and a heavy chain constant region 1 (CH1), X' is the antigen-binding fragment comprising a light chain variable region (VL) and a light chain constant region (CL), Y is the IL-2 variant that comprises the sequence of SEQ ID NO: 40 with a modification, wherein the modification is one or more substitutions selected from the group consisting of R38A, F42A, and E61R with regard to the amino acid sequence of SEQ ID NO: 40, $3^{rd}$ linker and $4^{th}$ linker are each a peptide linker, and q and r are each independently 0 or 1, wherein the heavy chain variable region (VH) comprises an HCDR1 comprising the amino acid sequence of SEQ ID NO: 24, an HCDR2 comprising the amino acid sequence of SEQ ID NO: 25, and an HCDR3 comprising the amino acid sequence of SEQ ID NO: 26; and the light chain variable region (LH) comprises an LCDR1 comprising the amino acid sequence of SEQ ID NO: 27, an LCDR2 comprising the amino acid DAS, and an LCDR3 comprising the amino acid sequence of SEQ ID NO: 29, and wherein the polypeptide chain of the structural formula (II) and the polypeptide chain of the structural formula (III) form a polypeptide heterodimer.

6. The fusion protein of claim 5, wherein the heavy chain variable region comprises the amino acid sequence of SEQ ID NO: 9, and the light chain variable region comprises the amino acid sequence of SEQ ID NO: 13.

7. The fusion protein of claim 5, wherein the linker $3^{rd}$ linker comprises the amino acid sequence of SEQ ID NO: 11.

8. The fusion protein of claim 5, wherein the $4^{th}$ linker comprises the amino acid sequence of SEQ ID NO: 12.

9. The fusion protein of claim 1, wherein the Fc region comprises the amino acid sequence of SEQ ID NO: 6.

10. A fusion protein dimer comprising two of the fusion protein of claim 1, wherein the two fusion proteins are linked to each other.

11. The fusion protein of claim 5, wherein the Fc region comprises the amino acid sequence of SEQ ID NO: 6.

12. A method for treating cancer comprising administering a pharmaceutical composition comprising, as an active ingredient, the fusion protein of claim 1 or a dimer thereof to a subject in need thereof.

* * * * *